US009536369B2

(12) United States Patent
Wagner

(10) Patent No.: US 9,536,369 B2
(45) Date of Patent: *Jan. 3, 2017

(54) PHARMACY MEDICATION VERIFICATION SYSTEM

(75) Inventor: David J. Wagner, Alliance, OH (US)

(73) Assignee: MICRO DATASTAT, LTD., Alliance, OH (US)

( * ) Notice: Subject to any disclaimer, the term of this patent is extended or adjusted under 35 U.S.C. 154(b) by 1265 days.

This patent is subject to a terminal disclaimer.

(21) Appl. No.: 13/451,098

(22) Filed: Apr. 19, 2012

(65) Prior Publication Data

US 2012/0209422 A1     Aug. 16, 2012

Related U.S. Application Data

(63) Continuation of application No. 12/277,387, filed on Nov. 25, 2008, now Pat. No. 8,914,148.

(60) Provisional application No. 61/004,239, filed on Nov. 26, 2007.

(51) Int. Cl.
| | |
|---|---|
| *G06F 7/00* | (2006.01) |
| *B65G 59/00* | (2006.01) |
| *G07F 17/00* | (2006.01) |
| *G06F 19/00* | (2011.01) |
| *G07F 11/62* | (2006.01) |
| *A61G 12/00* | (2006.01) |

(52) U.S. Cl.
CPC ......... *G07F 17/0092* (2013.01); *G06F 19/327* (2013.01); *G06F 19/3406* (2013.01); *G06F 19/3462* (2013.01); *G07F 11/62* (2013.01); *A61G 12/001* (2013.01)

(58) Field of Classification Search
CPC ............. B65B 5/00; A61G 12/001; A61J 7/02
USPC ......................... 700/231, 236, 240, 244, 237
See application file for complete search history.

(56) References Cited

U.S. PATENT DOCUMENTS

| | | |
|---|---|---|
| 5,713,485 A | 2/1998 | Liff et al. |
| 5,992,742 A | 11/1999 | Sullivan et al. |
| 6,176,392 B1 | 1/2001 | William et al. |
| 6,289,656 B1 | 9/2001 | Wangu et al. |
| 6,464,142 B1 | 10/2002 | Denenberg et al. |
| 6,497,342 B2 | 12/2002 | Zhang et al. |
| 6,510,962 B1 | 1/2003 | Lim |
| 6,522,945 B2 | 2/2003 | Sleep et al. |
| 6,611,733 B1 * | 8/2003 | De La Huerga ...... A61J 1/1437 700/235 |

(Continued)

*Primary Examiner* — Michael K Collins
(74) *Attorney, Agent, or Firm* — Cooper Legal Group LLC

(57) ABSTRACT

A pharmacy medication verification system is particularly useful for verifying medications to be dispensed to hospital patients while minimizing or eliminating verification by a pharmacist. Typically, a technician or robot picks the medications from storage bins in accordance with a medical prescription or stocking order and uses various sensors to ensure that the correct medication was picked and enters a medication container. The system typically provides correct and incorrect medication indicators as well as correct and incorrect entry indicators. Error reports may be generated when appropriate to communicate any relevant errors to the pharmacist, who can then verify that the correct medications are in the container. In one aspect, the containers are in the form of patient drawers which fit within a cart for delivery to hospital rooms. A containment device may be used to secure the drawer or other container during the verification process.

18 Claims, 32 Drawing Sheets

(56) References Cited

U.S. PATENT DOCUMENTS

| | | |
|---|---|---|
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,732,884 B2 | 5/2004 | Topliffe et al. |
| 6,757,898 B1 | 6/2004 | Ilsen et al. |
| 6,776,341 B1 | 8/2004 | Sullivan et al. |
| 6,785,589 B2 | 8/2004 | Eggenberger et al. |
| 6,799,725 B1 | 10/2004 | Hess et al. |
| 6,847,861 B2 | 1/2005 | Lunak et al. |
| 6,874,684 B1 | 4/2005 | Denenberg et al. |
| 6,895,304 B2 | 5/2005 | Spano, Jr. et al. |
| 6,985,797 B2 | 1/2006 | Spano, Jr. et al. |
| 6,996,455 B2 | 2/2006 | Eggenberger et al. |
| 7,006,214 B2 | 2/2006 | Rzasa et al. |
| 7,010,389 B2 | 3/2006 | Lunak et al. |
| 7,014,063 B2 | 3/2006 | Shows et al. |
| 7,016,766 B2 | 3/2006 | William et al. |
| 7,059,526 B1 | 6/2006 | Sullivan et al. |
| 7,072,737 B2 | 7/2006 | Lunak et al. |
| 7,077,286 B2 * | 7/2006 | Shows ............... G06F 19/3462 221/130 |
| 7,085,621 B2 | 8/2006 | Spano, Jr. et al. |
| 7,093,755 B2 | 8/2006 | Jordan et al. |
| 7,111,780 B2 | 9/2006 | Broussard et al. |
| 7,123,989 B2 | 10/2006 | Pinney et al. |
| 7,139,639 B2 | 11/2006 | Broussard et al. |
| 7,146,247 B2 | 12/2006 | Kirsch et al. |
| 7,228,198 B2 | 6/2007 | Vollm et al. |
| 7,263,411 B2 | 8/2007 | Shows et al. |
| 7,289,879 B2 | 10/2007 | William et al. |
| 7,370,797 B1 | 5/2008 | Sullivan et al. |
| 7,532,948 B2 | 5/2009 | Vollm et al. |
| 7,624,894 B2 | 12/2009 | Gerold et al. |
| 7,787,986 B2 * | 8/2010 | Pinney ............... G06F 19/3462 221/9 |
| 7,856,794 B2 * | 12/2010 | Zieher ................ B65B 5/103 53/246 |
| 7,971,414 B1 * | 7/2011 | McGonagle ............ A61J 1/035 53/246 |
| 8,914,148 B2 * | 12/2014 | Wagner ............... G06F 19/327 700/236 |
| 2005/0021175 A1 * | 1/2005 | Bain .................. G06F 19/3462 700/236 |
| 2005/0098626 A1 | 5/2005 | Jordan et al. |
| 2005/0113969 A1 | 5/2005 | Spano, Jr. et al. |
| 2005/0125097 A1 | 6/2005 | Chudy et al. |
| 2005/0263537 A1 | 12/2005 | Gerold et al. |
| 2006/0053036 A1 | 3/2006 | Coffman et al. |
| 2006/0125356 A1 | 6/2006 | Meek, Jr. et al. |
| 2006/0157492 A1 | 7/2006 | Shows et al. |
| 2006/0161293 A1 | 7/2006 | William et al. |
| 2006/0224274 A1 | 10/2006 | Broussard et al. |
| 2006/0226167 A1 | 10/2006 | Broadfield et al. |
| 2007/0023512 A1 | 2/2007 | Miller et al. |
| 2007/0027577 A1 | 2/2007 | Lunak et al. |
| 2007/0078562 A1 | 4/2007 | Park, IV |
| 2007/0208457 A1 | 9/2007 | Vollm et al. |
| 2008/0067190 A1 | 3/2008 | Daniels et al. |

* cited by examiner

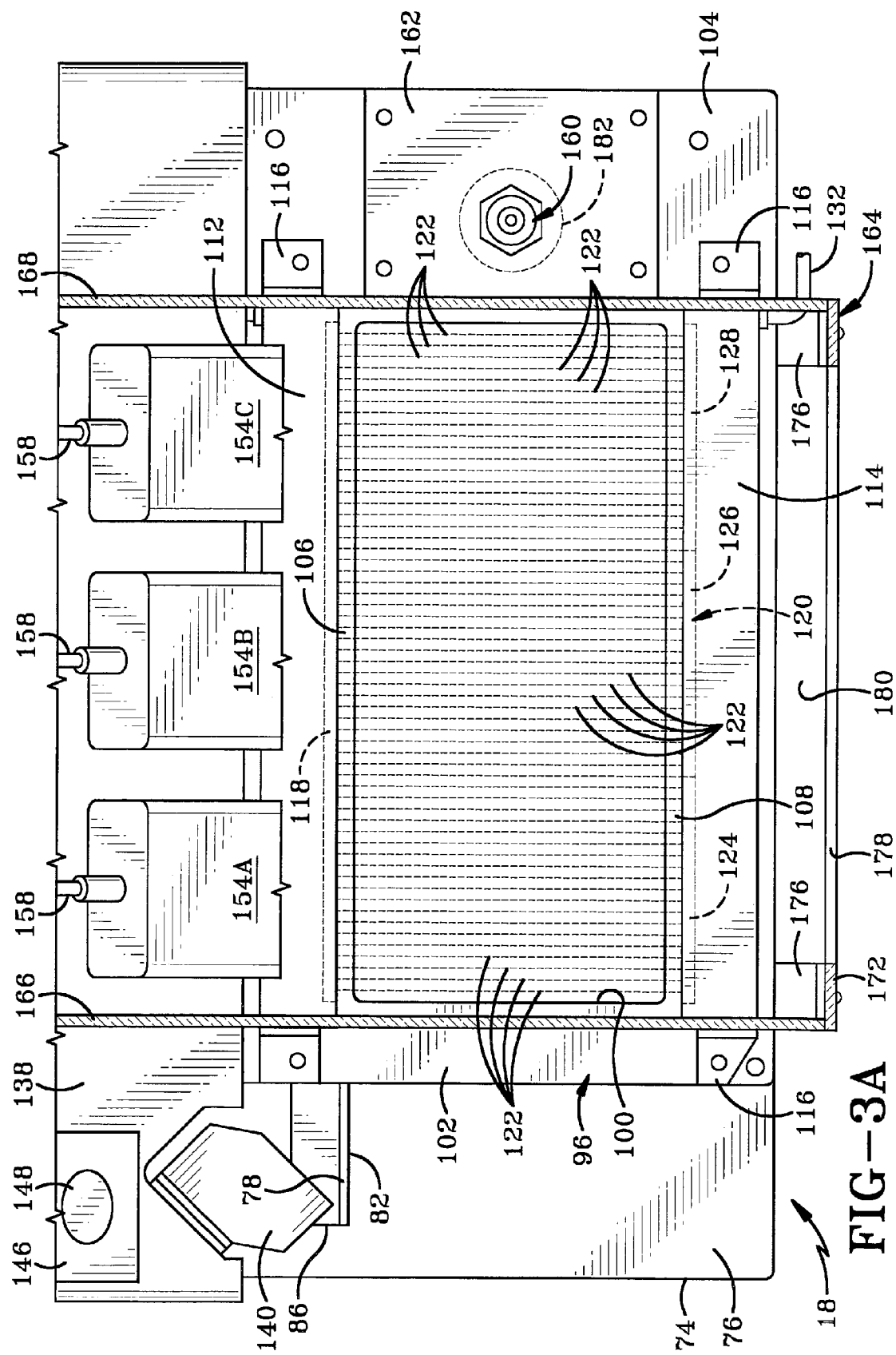

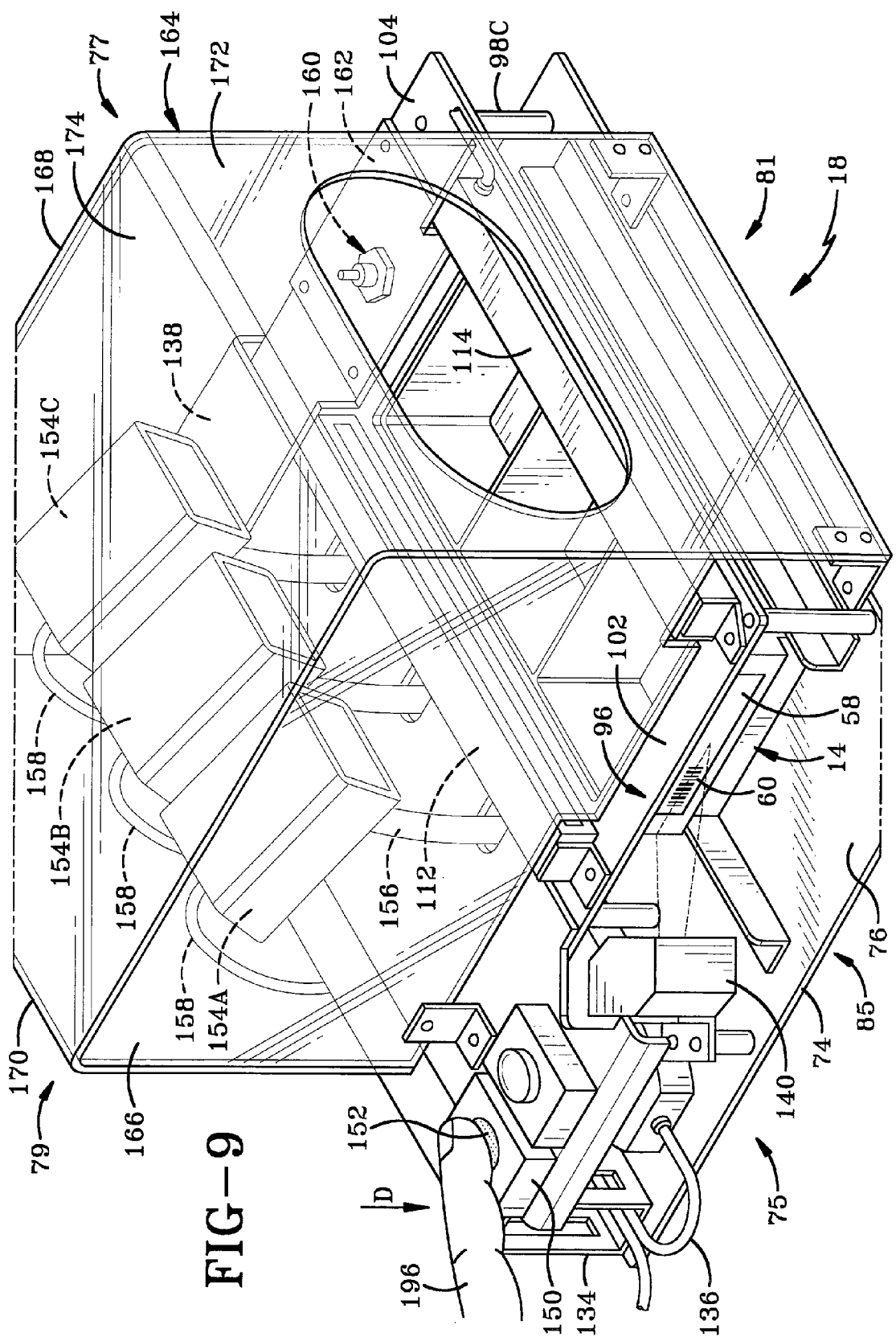

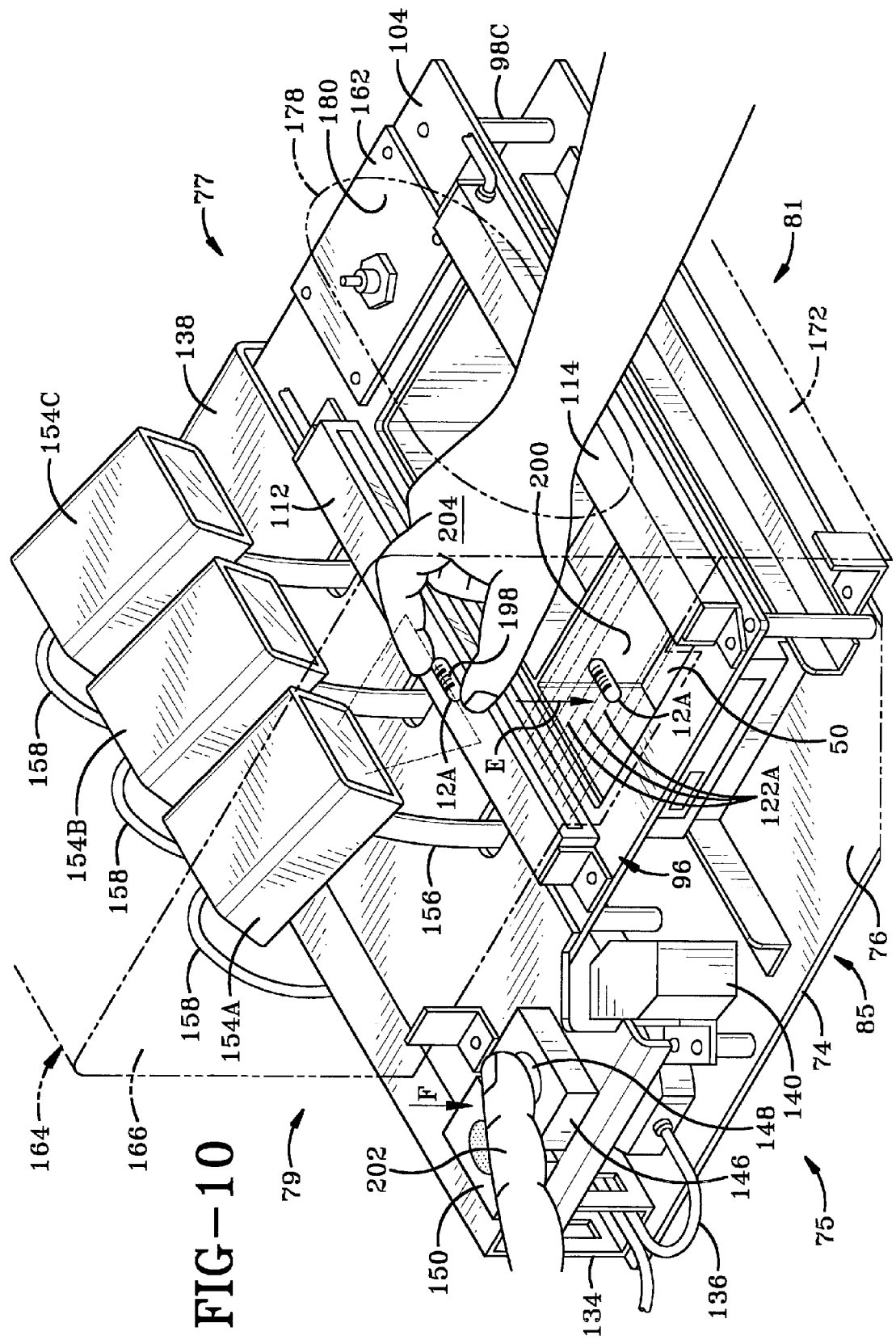

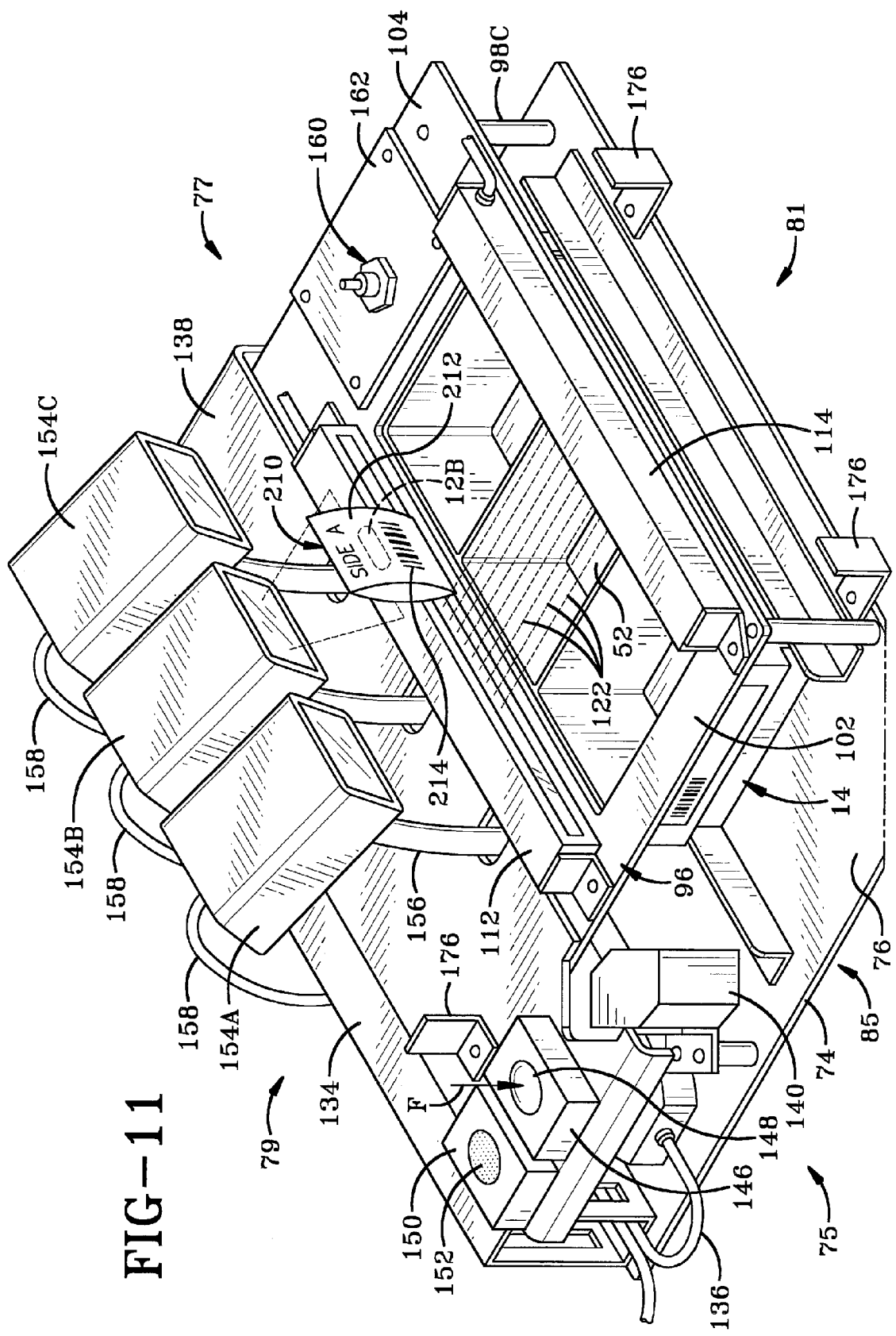

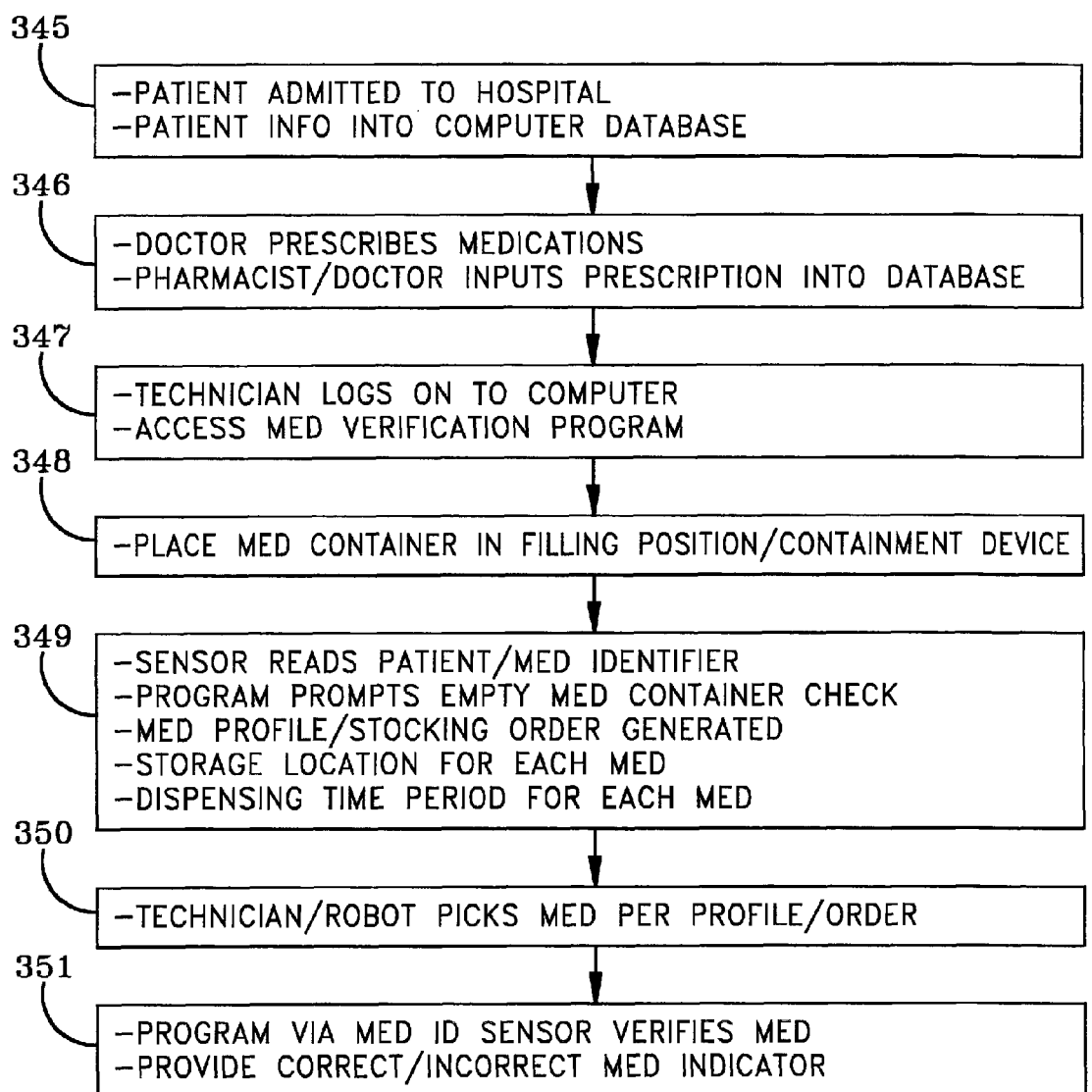

PHARMACY MEDICATION VERIFICATION SYSTEM

CROSS REFERENCE TO RELATED APPLICATIONS

This application is a continuation of U.S. patent application Ser. No. 12/277,387 filed Nov. 25, 2008, which claimed priority from U.S. Provisional Application Ser. No. 61/004,239 filed Nov. 26, 2007; the disclosures of which are incorporated herein by reference.

BACKGROUND OF THE INVENTION

1. Technical Field

The present invention relates generally to a system and method for controlling the dispensing of pharmaceutical and other medically related items. More particularly, the invention relates to a system which is particularly useful for verifying the accuracy of medicines and other items which are to be delivered from a hospital pharmacy to patients in the hospital.

2. Background Information

The dispensing of the proper medications to patients within a hospital is a very important aspect of heath care delivery. For several decades, rolling carts have been used to transport medications from a hospital's pharmacy to hospital patients. These carts have multiple drawers each assigned to an individual patient so that a given patient's medications are disposed in a single drawer within one of the carts. As a practical matter, there are two sets of drawers one of which is generally kept at a nurses station in the hospital and the other of which is generally kept within the pharmacy to be refilled in preparation for dispensing the next day's medications. In short, a technician picks or pulls the pertinent medications for given patients in accordance with a patient-specific list of medications and places them in the patient drawers of the pharmacy carts, which are taken to the nurses station where the drawers of the pharmacy cart are exchanged with those of the nurses cart in preparation for subsequent delivery to hospital patients. The carts thus allow for prescriptions to be filled at the centralized location represented by the pharmacy and transported to decentralized locations such as nurses' stations and patient rooms. A pharmacist verifies that the medications within each drawer are the proper medications.

Dispensing cabinets are also commonly used in the medication delivery system, including automated dispensing cabinets (commonly known as ADCs) which are configured to help control the proper dispensing and tracking of medications. Dispensing cabinets are typically positioned at or near a nurses station and may, like the carts noted above, be configured for transport between the centralized pharmacy and decentralized nurses station for stocking and dispensing, respectively. Such dispensing cabinets have various configurations, but typically include a number of drawers each of which are divided into or contain numerous compartments each of which serves to hold a specific medication in bulk. These compartments may or may not be removable from the drawer. Some of these compartments are configured as open top containers while others include lids which may be opened and closed. One example of such a compartment having a lid is disclosed in U.S. Application Publication 2006/0226167 of Broadfield et al., wherein the lidded compartment is commonly referred to as a "cubie". The number of such compartments within a drawer may easily be 20, 30, 40 or more. These compartments are stocked or re-stocked respectively in accordance with an initial stocking order or re-stocking order which is typically created by a pharmacist or a company which manufactures or sells the dispensing cabinet. As with the patient drawers discussed above, a pharmacist will verify that the proper medications are used to fill these compartments during the stocking or re-stocking process. Although this process of verifying that the proper medications reach a patient's drawer or the compartments of a dispensing cabinet is important, it is also very time consuming.

While there have been a variety of improvements in the verification systems for these medications, there is still a need in the art to provide a more reliable verification system.

BRIEF SUMMARY OF THE INVENTION

The present invention provides a method comprising steps of: determining with a medication identification sensor whether a first medication is a correct or incorrect medication; producing a correct or incorrect medication indicator respectively depending on whether the first medication is the correct or incorrect medication in accordance with the step of determining; causing entry of the first medication into a medication container after the step of producing; and sensing the entry with an entry sensor to verify that the first medication has entered the container.

BRIEF DESCRIPTION OF THE SEVERAL VIEWS OF THE DRAWINGS

FIG. 2A is a top plan view of the rear section of the patient drawer.

FIG. 3A is an enlarged top plan view of most of the containment device with the transparent box shown in section and showing the plane of detection formed by the light beams shown in parallel dashed lines above the access opening of the containment device.

FIG. 9 is a perspective view of the containment device showing the patient drawer inserted therein, the patient identification/information reader reading the patient identification/information label on the patient drawer and the fingerprint reader reading the fingerprint of the technician or other user of the system.

FIG. 10 is similar to FIG. 9 with the box shown partially in phantom for clarity and shows the right hand of a technician scanning a pill and the pill being dropped through the light curtain toward the patient drawer while the left hand of the technician is pushing the button of the sensor enablement device outside the box.

FIG. 11 is similar to FIG. 10 and shows one of the medication identifier scanners scanning a first label on a medication package.

FIG. 25 is a perspective view showing a medication in the form of a pill with a caution label adhered directly thereto.

DETAILED DESCRIPTION OF THE INVENTION

Figure 1:
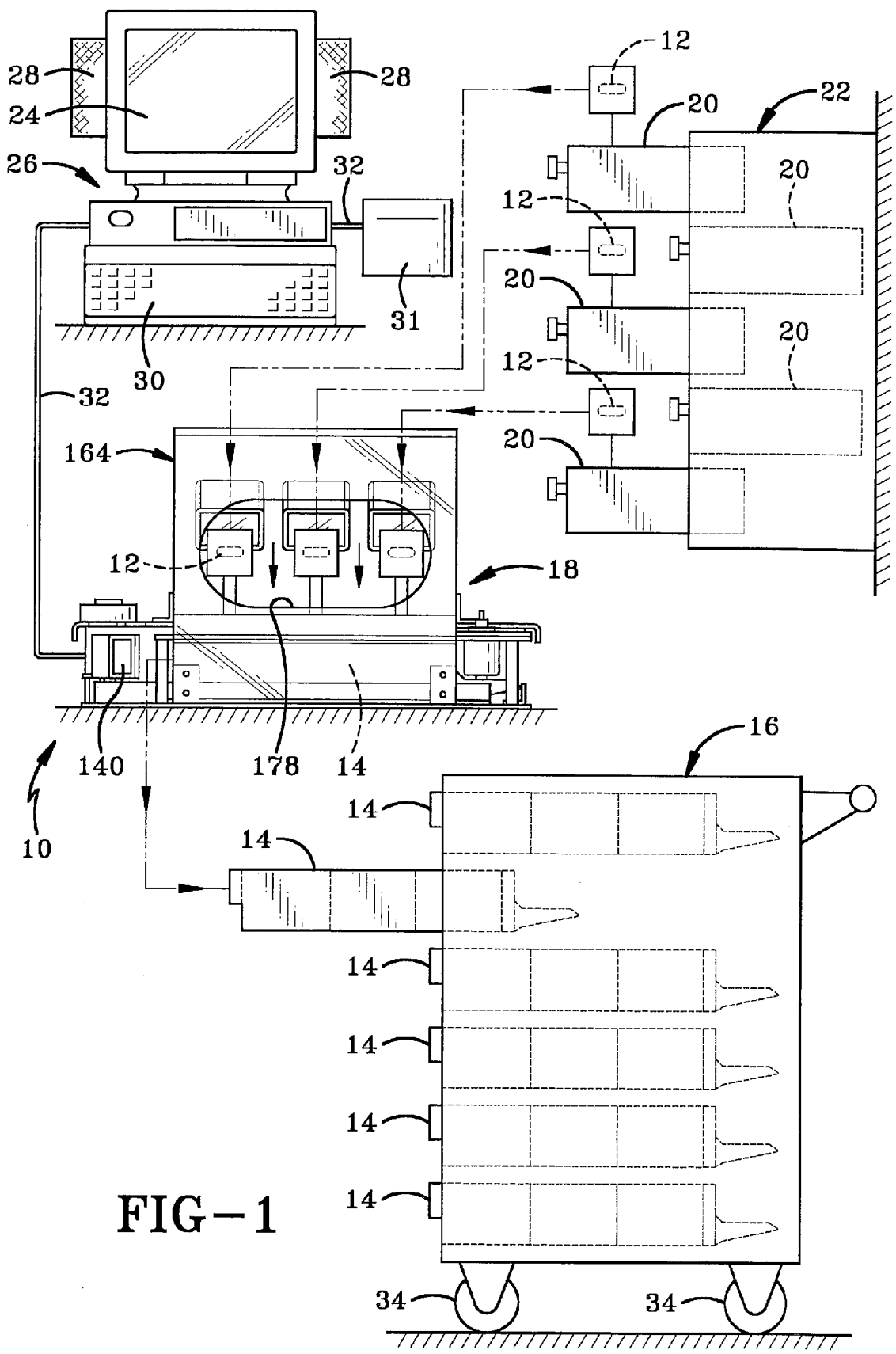
FIG. 1 is diagrammatic view of the pharmacy medication verification system of the present invention.

The pharmacy medication verification system of the present invention is shown generally at 10 in FIG. 1. System 10 may be used to verify the accuracy of patient cart fill, that is, to verify the accuracy of the medications 12 which are ultimately placed in a given patient-specific container such as a patient drawer 14, which is subsequently inserted into a rolling patient cart 16. System 10 may also be used to verify the accuracy of stocking or re-stocking storage or dispensing cabinets, that is, to verify that the proper medications are placed in a given medication-specific container such as the multiple compartments typically found within a given drawer of a medication dispensing cabinet. System 10 is used primarily with prescription or controlled medications although certain aspects of system 10 are more particularly intended for use with non-prescription or non-controlled medications, as discussed further below. While cart 16 is illustrated here as a standard hospital cart, it is also represents for the purposes of the present application a storage or dispensing cabinet, including an automated dispensing cabinet which may be substantially more complex in various aspects of its configuration including computer controlled operation for the purpose of dispensing and tracking medications. Cart 16 is in essence a cabinet having drawers 14 each of which serves as a medication container and which includes a plurality of compartments as discussed below which are analogous to those of a dispensing cabinet.

While a medication container such as patient drawer 14 is disposed in a patient drawer containment device 18, medications 12 are chosen from various storage bins 20 of a storage unit 22 in accordance with a computer-generated list typically displayed on a screen 24 of a computer 26 so that medications 12 may be placed in the drawer 14 within containment device 18 with verification of the medications provided by various sensors and other control devices which are in electrical communication with computer 26. Storage bins 20 may be, for example, drawers which slide in and out, stationary bins or bins which are revolved on a carrousel in order to access medications 12 therefrom. System 10 includes software or a computer program which is run by a central processing unit (CPU) of computer 26 for controlling various aspects of the invention as described further below. Computer 26 includes a pair of speakers 28 and an input mechanism such as a keyboard 30. It may also include a mouse or various other standard accessories usable with the invention. A printer 31 is provided which may be used for printing any of the labels, reports and the like which are described further below including any human readable information and any machine readable data or codes. Printer 31 represents a device which may be used to print bar codes, and also a device for creating or writing other types of machine readable labels. For instance, printer 31 may write to or on a radio frequency identification (RFID) tag or transponder to create an RFID tag. Computer 26 is in electrical communication with printer 31 and various other components of system 10 via electrical wires 32, as described further below.

Once a given patient drawer 14 or other medication container is filled with the medications 12 which are typically listed on display screen 24, drawer 14 is removed from containment device 18 and replaced in cart 16. The process is then repeated for all of the drawers 14 within cart 16 so that cart 16 is ready to be removed from the pharmacy to dispense the various medications to patients throughout the hospital. To that effect, cart 16 includes a plurality of wheels 34 so that a single person pushing or pulling cart 16 may easily roll it from place to place within the hospital. Drawer 14 is usually disposed in cart 16 and is movable in a standard fashion between open and closed positions. Cart 16 includes a locking mechanism which may be locked to secure each drawer 14 in its closed position and unlocked to allow the drawer to move between the open and closed positions, as well as be removed from cart 16 and replaced therein.

Figure 2:
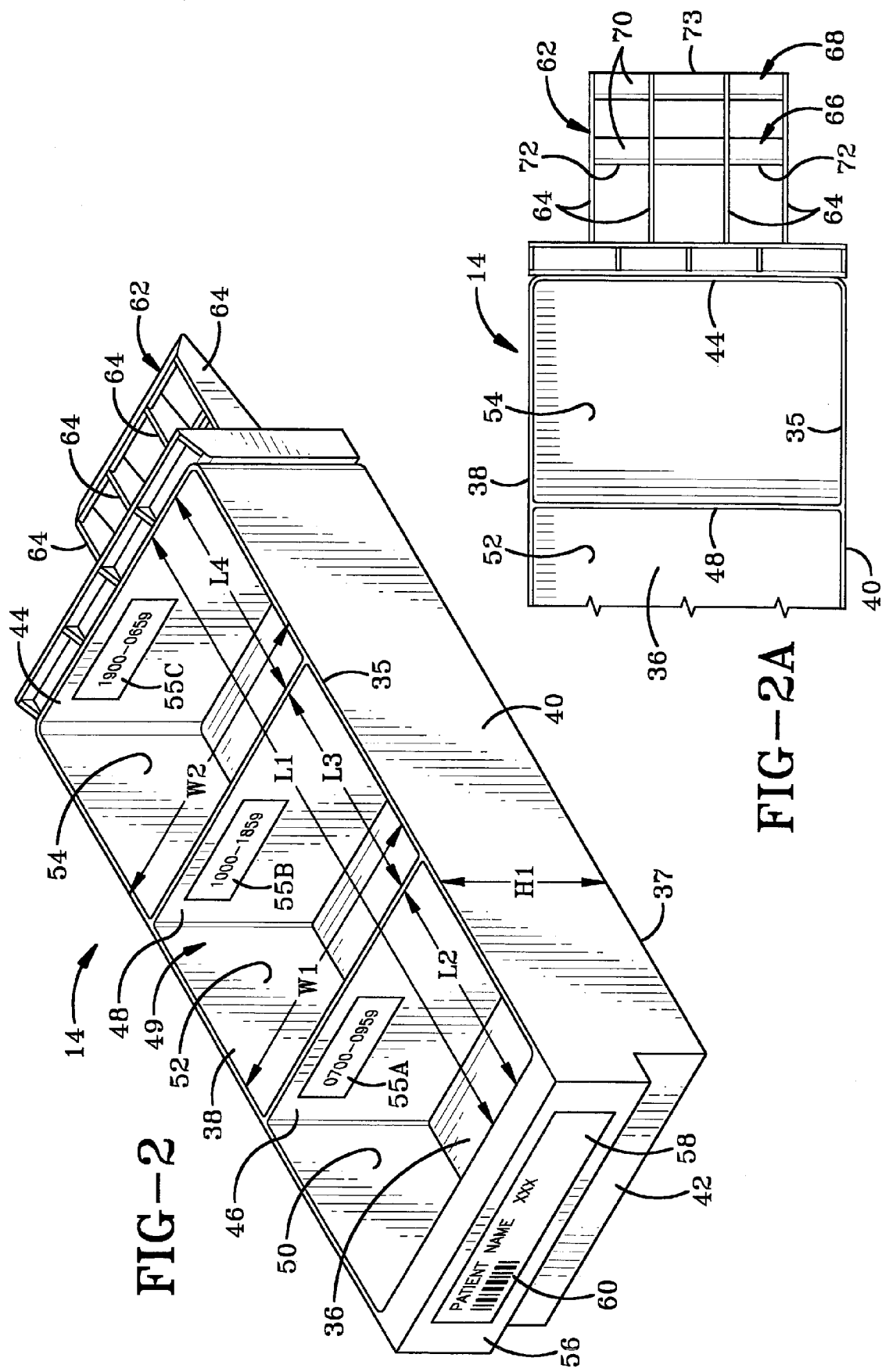
FIG. 2 is a perspective view of the patient drawer.

FIG. 2 shows the standard patient drawer 14 in greater detail. Drawer 14 is sufficiently small so that a single individual can easily support drawer 14 with one or two hands and thus manually transport and otherwise manipulate it to position it as desired. Drawer 14 is generally rectangular and thus includes a rectangular bottom wall 36, first and second rectangular sidewalls 38 and 40 connected to and extending upwardly from bottom wall 36, and front and back rectangular walls 42 and 44 connected to and extending upwardly from bottom wall 36 and extending respectively from first wall 38 to second wall 40. Drawer 14 has a top 35 which represents the uppermost edge of the various walls 38, 40, 42 and 44. Drawer 14 also has a bottom 37 which is the bottom surface of bottom wall 36 and/or walls 38, 40, 42 and 44. Top and bottom 35 and 37 define therebetween a height H1 of drawer 14.

First and second dividers 46 and 48 are typically disposed within drawer 14 parallel to front and rear walls 42 and 44 so that front wall 42 and first divider 46 define therebetween a first or front upwardly opening compartment 50, first and second dividers 46 and 48 define therebetween a second or intermediate upwardly opening compartment 52, and second divider 48 and back wall 44 define therebetween a third or rear upwardly opening compartment 54. Drawer 14 defines a medication compartment 49 extending from front wall 42 to rear wall 44, from sidewall 38 to sidewall 40 and from bottom wall 36 upwardly to the top 35 of each of walls 38, 40, 42 and 44. Thus, compartment 49 has a length L1 extending from front wall 42 to rear wall 44 and a substantially constant inner width W1 extending from the inner surface of sidewall 38 to the inner surface of sidewall 40. The outer surfaces of side walls 38 and 40 define therebetween and width W2 representing the widest portion of drawer 14 extending in the axial direction and wherein width W2 is substantially constant from front wall 42 to rear wall 44. Front compartment 50 has a length L2 extending from front wall 42 to first divider 46. Likewise, compartment 52 has a length L3 extending from first divider 46 to second divider 48 and rear compartment 54 has a length L4 extending from second divider 48 to rear wall 44 so that length L1 of compartment 49 is substantially equal to the total of length L2, length L3 and length L4. Width W1 thus also represents the width of each of compartments 50, 52 and 54.

Figure 6:
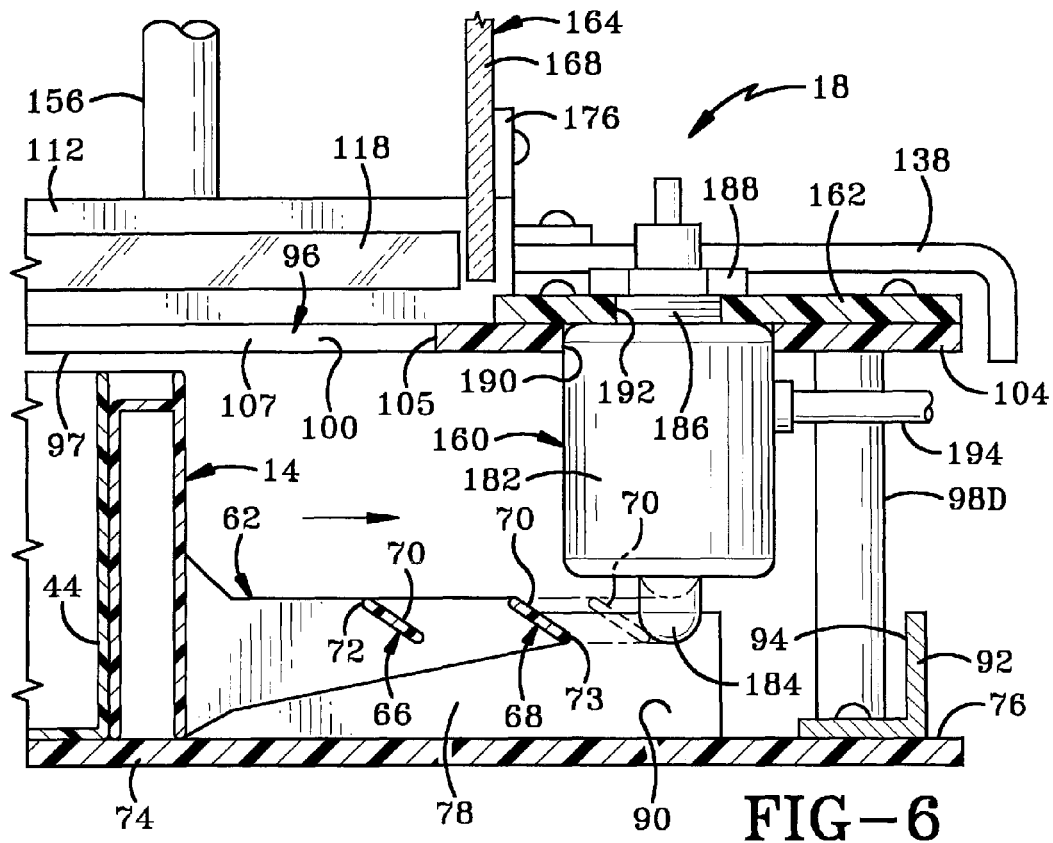
FIG. 6 is a sectional view taken on line 6-6 of FIG. 5.
Figure 8:
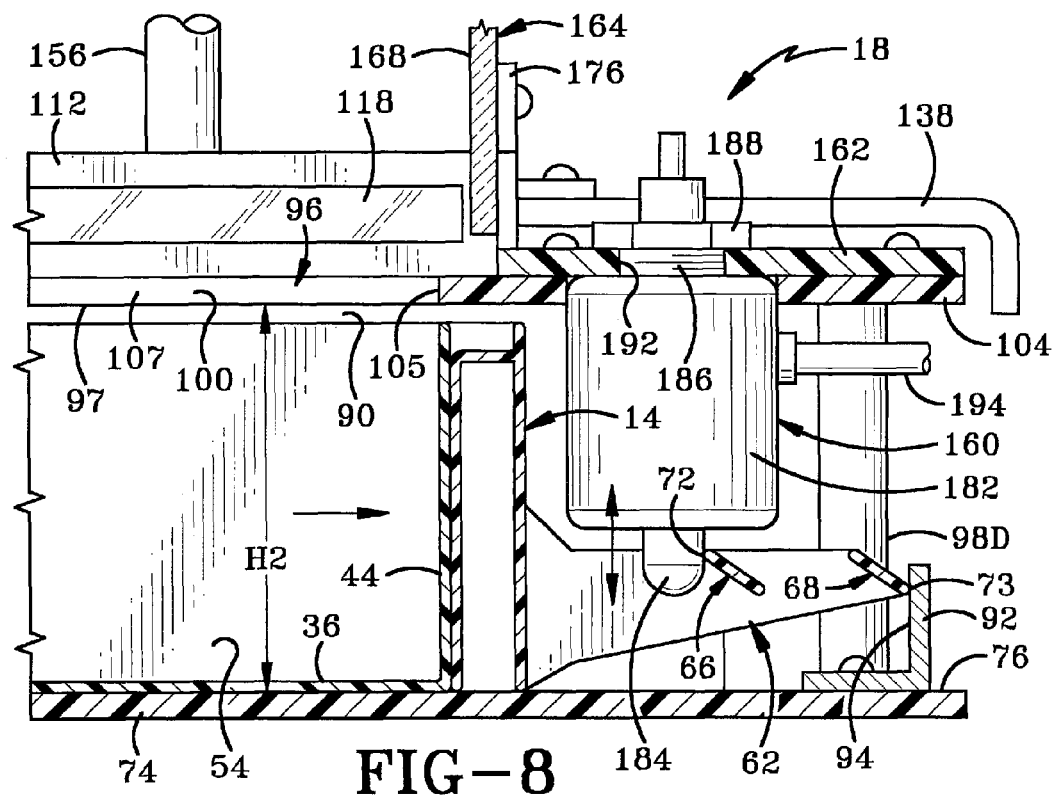
FIG. 8 is a sectional view taken on line 8-8 of FIG. 7.

Compartments 50, 52 and 54 are respectively associated with three medication-dispensing or medication administration time periods within a 24-hour day, as indicated by time period labels 55A-C. Thus, medications 12 which are placed in front compartment 50 are to be dispensed to the patient during a first time period, while medications 12 placed in compartments 52 and 54 are to be dispensed to the patient respectively during subsequent second and third time periods. Labels 55A-C show an example of the respective time periods in military time nomenclature, with the first period being 0700-0959 (7:00 AM-9:59 AM) or about three hours long, the second period being 1000-1859 (10:00 AM-6:59 PM) or about nine hours long, and the third period being 1900-0659 (7:00 PM-6:59 PM) or about twelve hours long, with the three time periods thus totaling a 24-hour duration. Drawer 14 further includes a handle 56 connected to and extending forward from front wall 42 so that drawer 14 may be manually removed from and replaced in cart 16 and containment device 18. A patient identification/information label 58 is mounted on the front of drawer 14 on handle 56 and includes the patient's name in human readable printed text form and a machine readable identifier 60 associated with the patient and/or one or more medications. Identifier 60 may be a bar code, a radio frequency identification (RFID) tag or any other suitable machine readable identifier. Drawer 14 further includes a lock engageable structure 62 which is connected to and extends rearwardly from adjacent back wall 44. Structure 62 includes four flat generally vertical fins 64 and first and second crossbars 66 and 68 which extend between and are connected to each of fins 64. Crossbars 66 and 68 each include a cam surface 70 which tapers downwardly and rearwardly, as shown in FIGS. 6 and 8. Crossbar 66 includes a front or forward facing locking surface 72. Second crossbar 68 includes a rearmost stop engagement surface 73.

Figure 3:
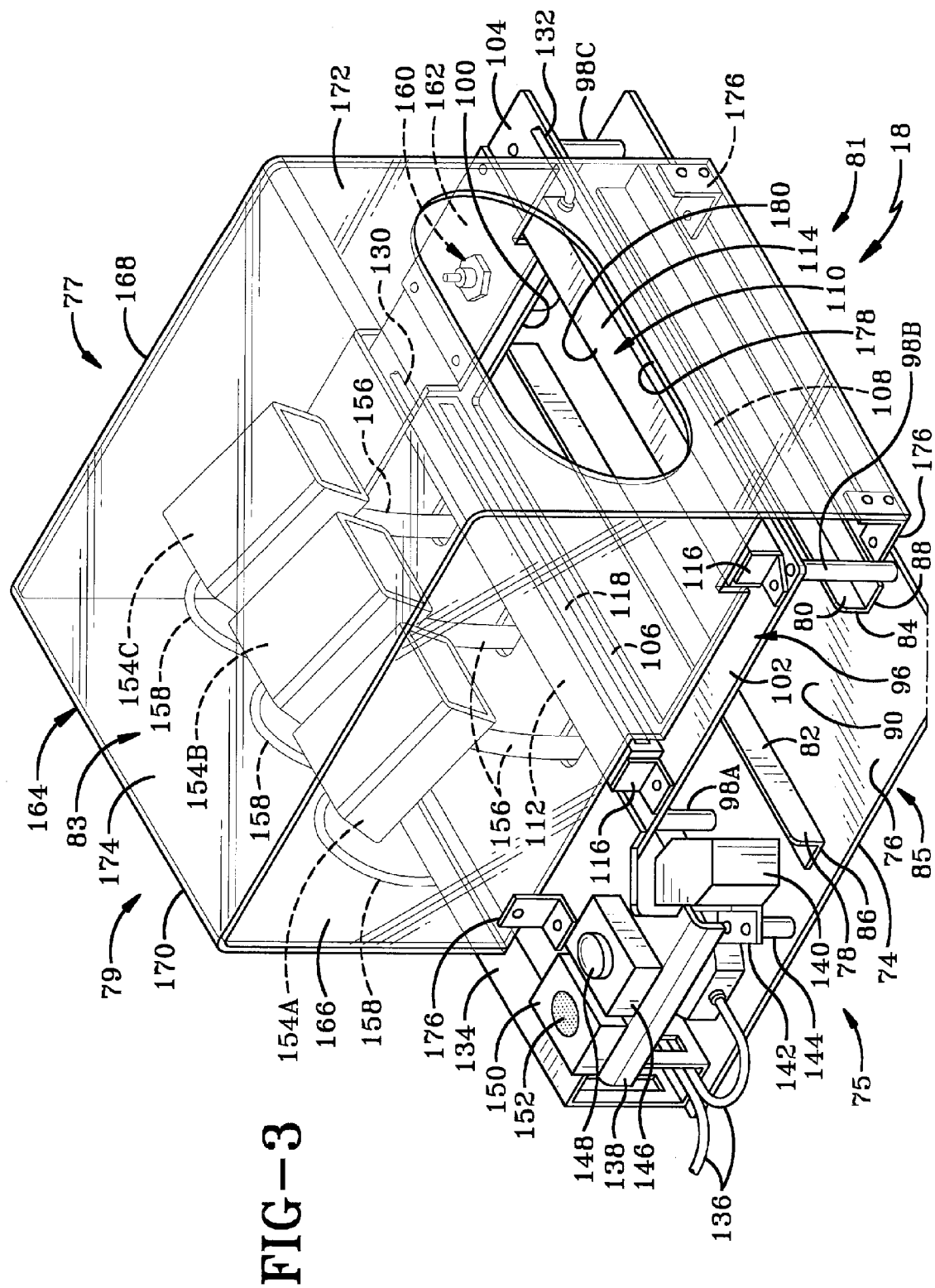
FIG. 3 is a perspective view of the patient drawer containment device and related structure.

With reference to FIG. 3, containment device 18 and the related structure of system 10 is described in greater detail. Containment device 18 and the associated structure thereof have a front 75 and a rear 77 defining therebetween a longitudinal direction of the structure, first and second sides 79 and 81 defining therebetween an axial direction of the structure, a top 83 and a bottom 85. Device 18 includes a rigid bottom wall 74 having a lower surface typically seated on a tabletop or counter at a height suitable for a technician or other operator of system 10, typically while standing, to manually operate device 18 and the related structure. Bottom wall 74 has an upper surface 76 which is substantially horizontal and serves as a sliding surface which drawer 14 slidably engages upon insertion and removal of drawer 14 into and out of device 18. First and second parallel longitudinally extending rigid guide walls 78 and 80 are rigidly connected to bottom wall 74 and extend upwardly therefrom in a vertical manner. Guide walls 78 and 80 are shown in the exemplary embodiment as upwardly extending legs of respective angles. Walls 78 and 80 have respective inner guide surfaces 82 and 84 which face one another and are slidably engaged by drawer 14 upon insertion and removal. Guide wall 78 has a front end 86 which is positioned forward of a front end 88 of second guide wall 80, typically a few inches, to facilitate insertion of drawer 14 into a drawer-receiving space 90 defined between guide walls 78 and 80 and bounded by upper surface 76 of bottom 74. Inner surfaces 82 and 84 of guide walls 78 and 80 define therebetween a width W3 (FIG. 4) which is slightly larger than width W2 of drawer 14 so that drawer 14 may slide along upper surface 76 of bottom wall 74 with inner surfaces 82 and 84 serving as guides which slidably engage the outer surfaces of sidewalls 38 and 40 of drawer 14 and also serve to limit the axial movement of drawer 14 when positioned within drawer-receiving space 90. A rigid rear stop or stop wall 92 (FIGS. 6, 8) having a forward facing stop surface 94 is rigidly connected to and extends upwardly from bottom wall 74 adjacent its rear end and bounds the rear of drawer-receiving space 90. In the exemplary embodiment, stop wall 92 is an upwardly extending leg of an angle with the other leg secured to wall 74.

Containment device 18 (FIG. 3) further includes a rigid transparent elevated wall 96 which is substantially horizontal and spaced upwardly from bottom wall 74 by four supports or posts 98A-D with posts 98A and B serving as axially spaced front posts and posts 98C and D (FIGS. 6, 8) serving as axially spaced rear posts. Elevated wall 96 is substantially horizontal and thus parallel to bottom wall 74. A rectangular medication access opening 100 has been cut into or otherwise formed in flat wall 96 which thus includes a front wall section 102, a rear wall section 104 and first and second sidewall sections 106 and 108 each of which is flat and bounds access opening 100. Elevated wall 96 has a lower surface 97 so that lower surface 97 and upper surface 76 of bottom wall 74 define therebetween a height H2 (FIG. 8) which is only slightly greater than height H1 of drawer 14. Lower surface 97 bounds the top of drawer-receiving space 90 so that height H2 also represents the height of space 90. Thus, the space between the top of drawer 14 and lower surface 97 when drawer 14 is inserted into space 90 is sufficient to allow drawer 14 to easily slide into and out of space 90 while lower surface 97 serves as a stop to upward movement of drawer 14 which typically substantially eliminates such upward movement. While upward movement of drawer 14 within space 90 is permissible to some extent, it is preferred that this is kept to a minimum. In addition, it is preferred that the distance between the top of drawer 14 and lower surface 97 is too small to allow for the passage of medication 12 therethrough, thus eliminating the possibility of medication 12 not entering drawer 14 during the drawer fill procedure due to such passage.

Figure 7:
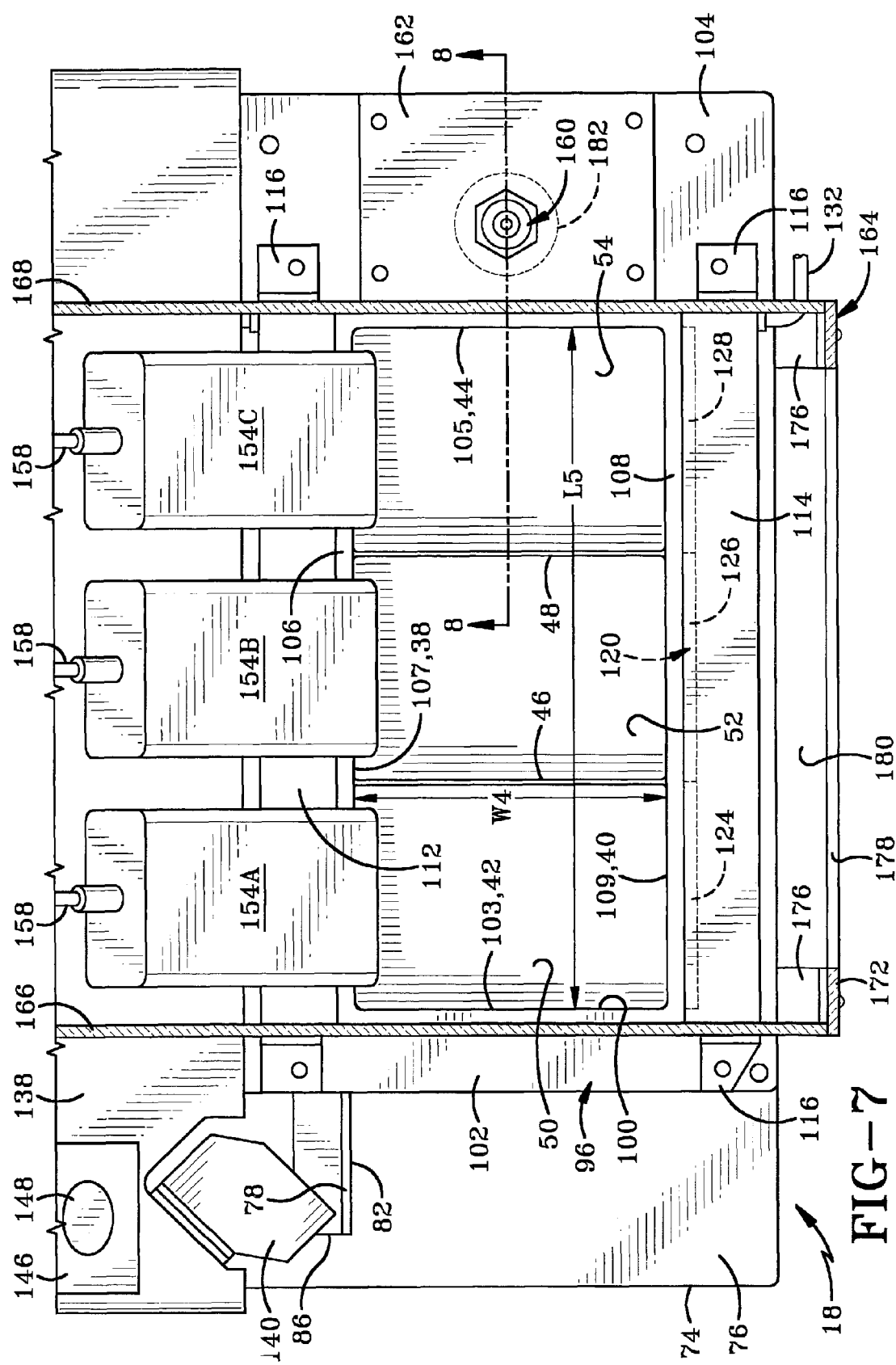
FIG. 7 is similar to FIG. 5 and shows the drawer fully inserted and locked in a secured position.

As shown in FIG. 7, front wall section 102 has a straight axially extending rearward facing surface 103 which bounds access opening 100. Likewise, rear wall section 104 has a straight axially extending forward facing edge or surface 105 which is parallel to surface 103 and also bounds access opening 100. Similarly, side walls sections 106 and 108 respectively have first and second lateral edges or surfaces 107 and 109 which are parallel to one another and extend longitudinally perpendicular to surfaces 103 and 105 and bound access opening 100. Thus, edges or surfaces 103 and 105 face one another, as do edges or surfaces 107 and 109 to define the rectangular shape of opening 100. Surfaces 103 and 105 define therebetween a length L5 of access opening 100 which is approximately the same as length L1 of compartment 49 of drawer 14. Length L5 may be somewhat shorter than length L1 as long as front and rear wall sections 102 and 104 do not interfere with the dropping of medications 12 into compartments 50 and 54 to an objectionable degree. Similarly, length L5 may be somewhat longer than length L1, but should not be longer to the degree that medications 12 may be dropped outside of these compartments between a respective one of edges 103, 105, 107, 109 and a corresponding vertical wall of drawer 14 when drawer 14 is secured within drawer-receiving space 90 in its fill position. Edges or surfaces 107 and 109 define therebetween a width W4 of access opening 100 which is approximately the same as width W1 of compartment 49 of drawer 14. Due to the relatively thin walls of drawer 14, width W2 thereof is only slightly larger than width W1 and thus width W4 is also approximately the same as width W2. As discussed with the possible variation of length L5, width W4 may also be somewhat larger or somewhat less than width W1 or width W2 in accordance with the same rationale.

System 10 further includes a type of medication sensor referred to herein as an entry sensor or drop sensor typically in the form of a presence sensing device such as a light curtain 110 comprising a light-transmitting mechanism 112 and a light receiving mechanism 114 each in the form of an elongated rectangular bar secured at either end to elevated wall 96 by respective mounting brackets 116 in the form of short L-shaped angles. Transmitter 112 is in electrical communication with a source of electric power (not shown) via a wire 130, which also may be in electrical communication with computer 26. Likewise, receiver 114 is in electrical communication with an electric power source and computer 26 via a wire 132. Transmitter 112 includes an array 118 of light-transmitting elements typically in the form of light emitting diodes (LEDs) and an array 120 of light-receiving elements typically in the form of phototransistors or photodiodes. Each of the light-transmitting elements or LEDs of array 118 projects a light beam to corresponding receiving elements of array 120 so that a plurality of parallel light beams 122 (FIG. 3A) is transmitted from array 118 to array 120 to provide a sensing field also commonly referred to as a plane of detection. Each of arrays 118 and 120 has a length approximately the same as length L5 of access opening 100 so that the plane of detection or sensing field produced by light beams 122 substantially covers access opening 100 at a height just above elevated wall 96. Light beams 122 are positioned close enough to one another to ensure that any medication 12 (or other item of equal or greater dimensions) dropped through opening 100 into space 90 and into drawer 14 when disposed in space 90 will interrupt one or more of beams 122 so that the medication is detected as it passes in its entirety through the plane of detection defined by beams 122, from one side of said plane there above to the other side of said plane there below.

Typically, the LEDs emit pulses of invisible infrared light when energized by the timing and logic circuitry of the light curtain so that the light pulses are both sequenced and modulated. Sequenced here means that one LED is energized after another while modulated means that the light is pulsed at a specific frequency. Thus, the phototransistors or photodiodes and supporting circuitry in photoelectric receiver 114 are configured to detect only the specific pulse and frequency designated for the given phototransistor or photodiode, which helps eliminate the interfering acceptance of ambient light or light from other sources. If desired, array 120 may be divided into smaller arrays or sub arrays such as the three sub arrays indicated at 124, 126 and 128 in FIG. 3A, the sub arrays thus serving as three independent entry sensors. Sub arrays 124, 126 and 128 are aligned to respectively correspond to compartments 50, 52 and 54 of drawer 14 when in its secured filling position within space 90 of containment device 18. More particularly, the length of each sub array is typically approximately equal to that of the respective compartment. Thus, any medication 12 or other items which pass through the plane defined by the beams 122 of sub array 124 would produce a signal indicating that medication 12 passed into compartment 50. Likewise, sub arrays 126 and 128 would allow for detection of medications 12 passing into compartments 52 and 54 respectively. Array 120 may also be configured without sub arrays so that the dropping of the medication 12 would simply indicate that the medication passed into drawer 14 without indicating the specific compartment thereof. Thus, the logic circuitry of light curtain 110 and/or the computer program run on computer 26 may be configured for either alternative.

While light curtain 110 has been described as utilizing a light transmitter on one side of access opening 110 and a photoelectric receiver on the other side, typically known as an opposed arrangement, it may also represent alternative arrangements. For instance, a retroreflective arrangement may be utilized in which the receiving elements described in array 120 are located instead within the housing of light transmitter 112 and array 120 is replaced by a reflector or mirror which reflects the light beams emitted from the transmitting elements back to the receiving elements. In the opposed arrangement and the retroreflective arrangement an opaque object is sensed when one or more beams 122 is interrupted and thus fails to reach the receiving element. While the opposed arrangement or retroreflective arrangement are preferred, is it also possible to use a proximity-sensing arrangement in which the transmitted beams must reflect off of the object such as medication 12 in order to reach the receiving elements, which may or may not be positioned adjacent the transmitting elements. In this mode, an object is detected when the receiving elements sense the beam reflected from the object instead of when it fails to sense a light transmission.

With reference to FIG. 3 once again, a cord housing or channel 134 is secured to bottom wall 74 and extends longitudinally along first side 79 to provide a housing through which electrical wires 136 extend. A wall or plate 138 is connected at the top of housing 134 and the top of elevated wall 96 along sidewall section 106 and extends longitudinally from adjacent front 75 to adjacent rear 77. A patient identifier and information access sensor 140 is secured to bottom wall 74 adjacent plate 138 via an L-shaped mounting bracket 142 and a pair of posts 144 (only one shown). Sensor 140 is in electrical communication with computer 26 and may be a bar code scanner, an RFID reader, a camera or other suitable device for reading a patient identifier or information code or label such as identifier 60 or the like. A manually engageable sensor enablement device 146 is mounted on plate 138 and includes a manually depressible button 148. Button 148 is movable between a non-depressed inactivated position and a depressed activated position, and is spring biased to the non-depressed position. Device 146 typically uses an electrical switch so that movement of button 148 between its depressed and non-depressed positions changes the state of an electric circuit from closed to open or vice versa. A fingerprint reader 150 is mounted on plate 138 adjacent device 146 and includes a finger pad 152 capable of reading a fingerprint. Sensor enablement device 146 and fingerprint reader 150 are in electrical communication with computer 26. Three medication identification sensors 154A, 154B and 154C are mounted on bottom wall 74 via respective support legs 156 and represent another type of medication sensor. Each sensor 154 is in electrical communication with computer 26 via a respective wire 158. Sensors 154A, B and C are adjacent and spaced from one another in the longitudinal direction and are spaced upwardly from transmitter 112 to face generally toward the space above access opening 100 and the sensing field of light beams 122 when activated. Sensors 154 and 140 are part of a medication sensor assembly of system 10. A locking mechanism 160 is mounted on rear wall section 104 of elevated wall 96 via a mounting plate 162 and is described in greater detail further below.

A transparent box 164 is provided and includes five substantially flat transparent walls, namely front wall 166, rear wall 168, first and second sidewalls 170 and 172 and top wall 174, the latter of which is substantially horizontal while the remaining walls extend upwardly and are typically substantially vertical. Box 164 is secured to plate 138 and bottom wall 74 via a plurality of mounting brackets 176 which are shown in the form of L-shaped angles (only three shown). Front and rear walls 166 and 168 extend upwardly from adjacent or in abutment with elevated wall 96 and plate 138 to connect to top wall 174. First sidewall 170 extends upwardly from adjacent or in abutment with housing 134 to connect to top wall 174. Second sidewall 172 extends upwardly from adjacent from bottom wall 74 adjacent second sidewall section 108 to connect to top wall 174. A generally oval manual access opening 178 is formed in second sidewall 172 and communicates with an interior chamber 180 defined by the various walls of box 164 to provide manual access between interior chamber 180 and the space external to box 164. Sidewall 172 thus serves as an access wall so that a technician or other user of system 10 may insert his or her hand from outside box 164 into interior chamber 180. Front wall 166 serves as a barricade wall to prevent the technician or other user of the system from inadvertently moving the other hand, namely the hand not inserted through access opening 178, from a position in the external space outside of wall 166 to the interior chamber 180 on the other side of wall 166. Top wall 174 serves as a cover wall which helps prevent various items from accidentally being dropped into interior chamber 180 and into drawer 14 when disposed in containment device 18. The remaining walls of box 164 also help prevent inadvertent insertion of various items into drawer 14. Box 164 is typically formed of Plexiglas® or another transparent material so that the transparency allows users to see what they are doing within box 164 during the process described below, for instance to view a medication, a hand and other items within chamber 180 through one of the walls of box 164.

Figure 13:
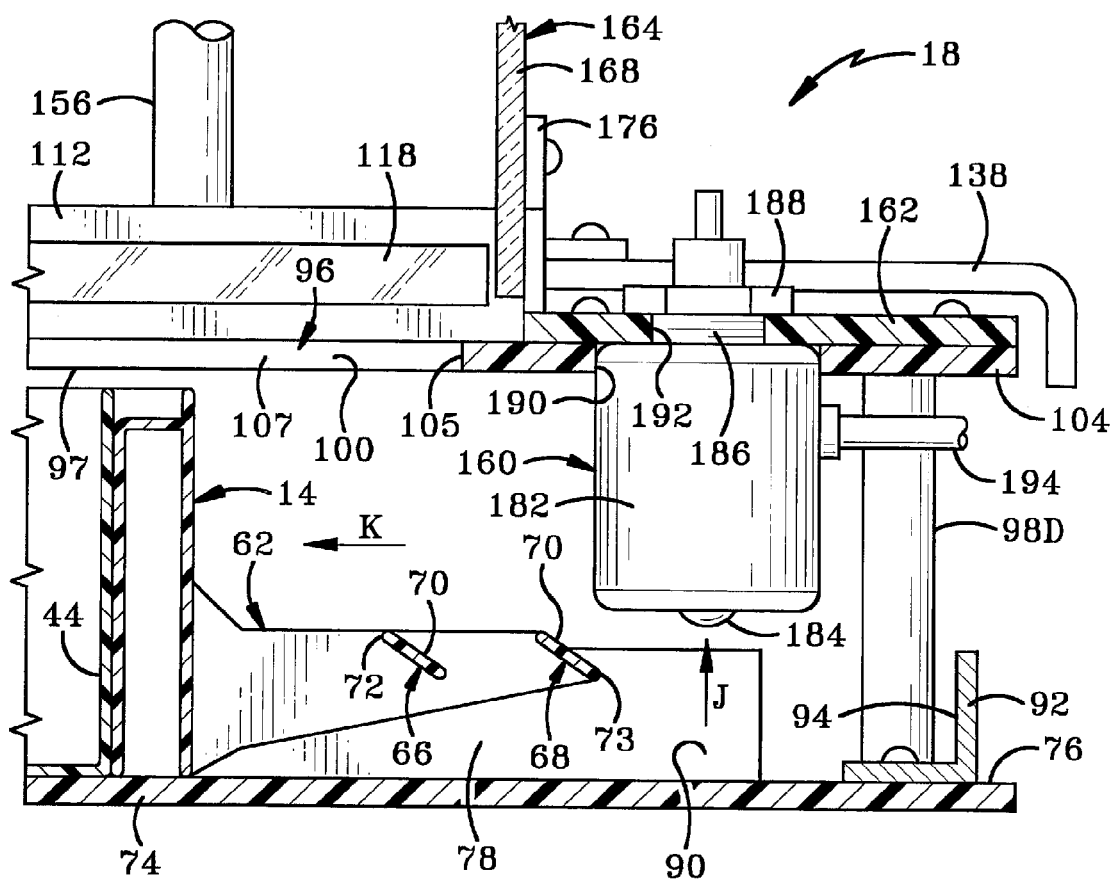
FIG. 13 is a sectional view similar to FIGS. 6 and 8 showing the locking mechanism in its unlocked position and the patient drawer being removed from the containment device.

Locking mechanism 160 is now described in further detail in reference to FIG. 6. Locking mechanism 160 is preferably an electromagnetic locking mechanism and thus includes a solenoid disposed within a housing 182. A plunger 184 is moveably mounted on housing 182 and extends through a bottom opening from partially within the housing to partially outside the housing. Plunger 184 has a rounded or dome shaped bottom which serves as a cam surface to facilitate its upward movement as described further below. A threaded portion 186 is rigidly connected to and extends upwardly from housing 182 and is threadedly engaged by a nut 188 to secure the upper portion of housing 182 within a larger bore 190 formed through rear wall section 104 of elevated wall 96 and to secure threaded portion 186 within a smaller through bore 192 formed in mounting plate 162. The solenoid of locking mechanism 116 is in electrical communication with an electric power source and computer 26 via a wire or wires 194. Plunger 194 is spring biased to its lowered position shown in FIG. 6 and moveable to its raised position shown in FIG. 13 when the solenoid is electrically activated. A manual key (not shown) may be provided to unlock mechanism 160 if there is a power failure or the solenoid fails.

The operation of system 10 is now described with reference to FIGS. 1 and 4-13. Before the technician begins filling the patient drawers 14, the pharmacist will have made or verified an association between each drug or medication 12 and the scan code or identifier 198 which applies to that medication so that the identifier 198 for a given medication 12 is recognized by and accurately specifies the given medication 12 within system 10 and the given pharmacy and hospital computer systems where applicable. To do this, the pharmacist may scan the identifier 198 of a given medication 12, identify the medication and assign the identifier 198 to the given medication 12. The computer program is thus configured for the pharmacist to make this association via an input mechanism of computer 26. System 10 is configured to use a biological identification (bio-ID) mechanism such as fingerprint reader 150 in order to track which pharmacist makes or verifies the association for a given medication 12. Thus, the computer program is configured to require that the pharmacist enter his or her bio-ID when making or verifying the association so that the computer program makes an automatic log of the pharmacist making the association. The record of who made the association may include only the last association made or all associations for a given medication. While system 10 provides fingerprint reader 150 to serve as the bio-ID mechanism, a retina scanner for making a positive identification of the pharmacist by scanning the retina of his or her eye may be used for this purpose amongst other known bio-ID mechanisms.

While the above description illustrates that the pharmacist assigns a specific identifier 198 to a given medication 12, the association between the medication and its identifier may be made otherwise and verified by the pharmacist. For example, a manufacturer or wholesaler of the medications, or another company, may produce a label with a bar code or the like having an identifier which is associated with the specific medication before it ever reaches the pharmacy. This identifier may be the same identifier which is used by system 10 and a given pharmacy such that the pharmacist does not need to make the association between the medication and its identifier, but merely to verify that the association is correct. The computer program of system 10 is thus configured for the pharmacist to scan the identifier and make an input into the system indicating that the medication identifier has been verified as being correct. Alternately, instead of one of the entities noted above producing the label with its identifier which is subsequently delivered to the pharmacy, the entity may provide a data feed of the required information to generate this label. Regardless of the specific process, the association between the medication and its identifier is to be verified by the pharmacist prior to using the given medication for filling a given medication container such as patient drawer 14 which is assigned to a specific patient or a compartment which is part of a storage or dispensing cabinet and thus assigned to a specific medication.

Figure 4:
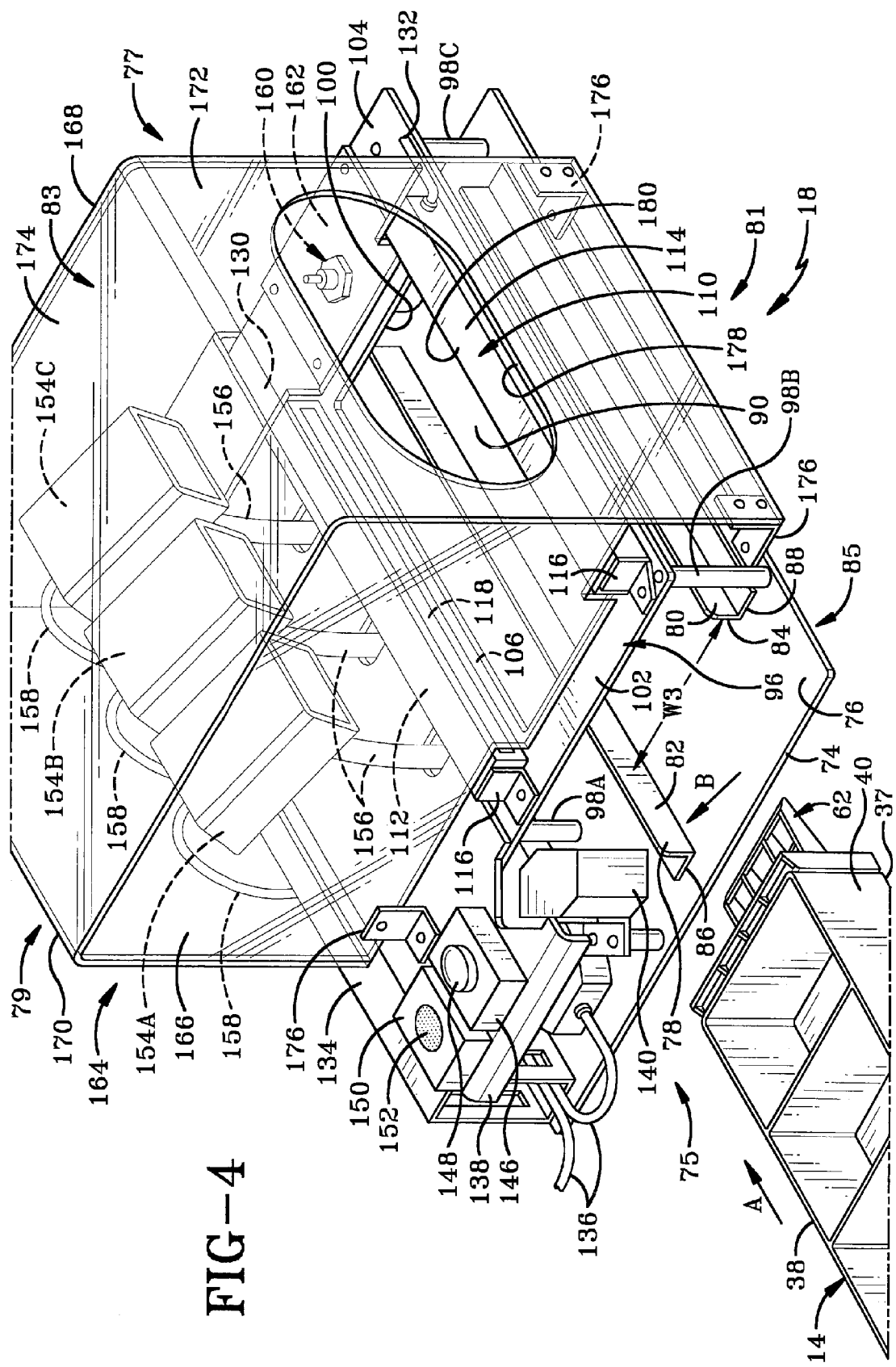
FIG. 4 is similar to FIG. 3 and shows a patient drawer prior to being inserted into the containment device.
Figure 5:
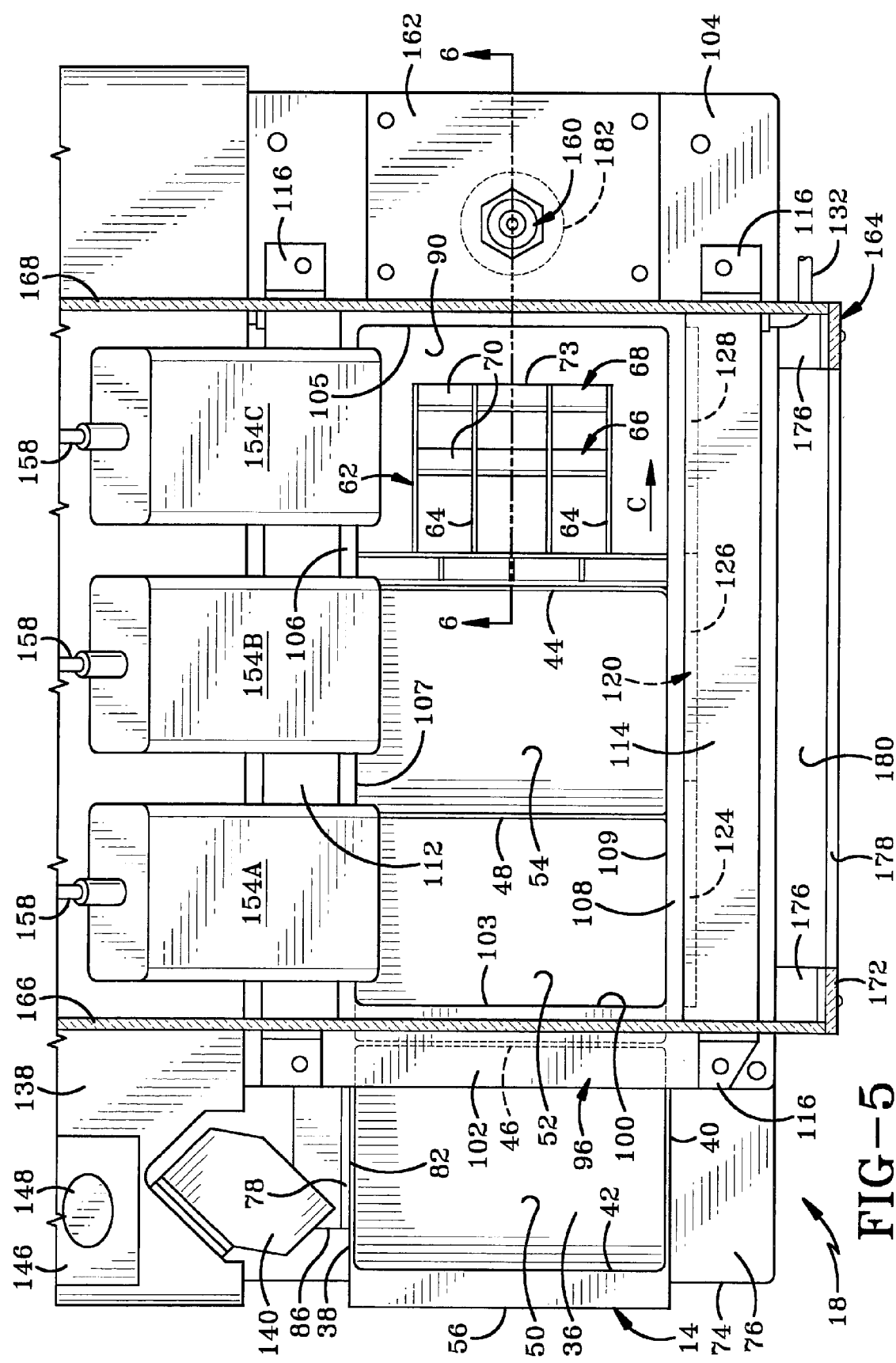
FIG. 5 is a top plan view of the front portion of the containment device with the transparent box shown in section and the drawer being inserted therein in an unsecured position.

The technician or other user of system 10 will remove one of patient drawers 14 from cart 16 in preparation for filling the drawer with a given patient's medications. As shown in FIG. 4, the lock engageable structure 62 at the rear of drawer 14 faces rearwardly as drawer 14 is moved toward the entrance opening of drawer receiving space 90 of containment device 18. FIG. 4 also illustrates the advantage of first guide wall 178 extending forward of second guide wall 80 by illustrating that drawer 14 may be slid on surface 76 of wall 74 or moved axially as indicated at Arrow B in a direction generally away from second wall 80 and toward first wall 78 in order to first engage surface 82 of first guide wall 78 forward of front 88 of second guide wall 80 and thus prior to the insertion of sidewall 40 of drawer 14 past the front of second guide wall 80. This configuration thus allows for drawer 14 to be easily aligned with drawer-receiving space 90 to facilitate insertion of drawer 14 therein. FIG. 5 shows that most of drawer 14 has slid into drawer receiving space 90 as indicated at Arrow C so that bottom 37 (FIG. 4) drawer 14 slidably engages upper surface 76 of bottom wall 74 while sidewalls 38 and 40 of drawer 12 respectively slidably engage inner surfaces 82 and 84 of guide walls 78 and 80. FIG. 6 illustrates a position of drawer 14 which is slid further rearwardly than that shown in FIG. 5 so that cam surface 70 of second crossbar 68 approaches the dome shaped outer surface of plunger 184 prior to being locked into a secured position by locking mechanism 160. FIG. 6 also shows in dashed lines cam surface 70 slidably engaging plunger 184 and forcing it upwardly as drawer 14 continues to move further rearwardly. Once crossbar 68 passes behind plunger 184, plunger 184 automatically moves downward in response to its spring bias. Subsequently, cam surface 70 of first crossbar 66 similarly engages the curved surface of plunger 184 to force it upwardly, then moves behind plunger 184 which once again springs downwardly into the locked positions of FIGS. 7 and 8. As shown in FIG. 8, when drawer 14 is in its secured fill position, the rear surface of plunger 184 engages locking surface 72 of crossbar 66 to provide an interference so that drawer 14 may not be withdrawn forward from within drawer receiving space 90 unless locking mechanism 160 is unlocked. Rearmost surface 73 engages stop surface 94 to provide an interference which prevents rearward movement of drawer 14. Drawer 14 in its secured position is substantially immobilized or stationary.

The movement of plunger 184 in response to the insertion of drawer 14 into its secured position may create a signal from locking mechanism 160 to computer 26 indicating that drawer 14 is in its secured position, which may cause the computer program to respond in various ways. For instance, the computer program at this time may activate the drop sensor, which could mean that light beams 122 are turned on or that the computer program will begin checking for interruption of the sensing field of the drop sensor if the sensing field is already activated. The computer program may also require at this time an empty drawer check and/or a drop area check. The empty drawer check would require that drawer 14 be checked to determine whether it is empty or not prior to its being filled in accordance with the computer generated list for a given patient in accordance with a medical prescription. To that effect, the computer program is typically configured to require the technician to respond with an answer of either "yes" or "no" to an inquiry or prompt (FIG. 9A) displayed on screen 24 as to whether the drawer is empty. The computer program will allow the verified filling of drawer 14 only if the answer is "yes". If the answer is "no", the computer will unlock locking mechanism 160 and will not continue with the verified filling of the drawer until the technician answers "yes". The technician checks the drawer and may manually remove items therefrom to ensure that the drawer is empty before proceeding. Alternately, device 18 may be configured to mechanically turn the drawer over to empty said drawer. The drop area check noted above may similarly require that the technician answer an inquiry or prompt (FIG. 9A) as to whether the drop area is clear of medications or other objects which may interfere with the process. For instance, such medications or objects may have inadvertently been positioned atop elevated wall 96, transmitter 112, and receiver 114 or within space 90. Ensuring that this area is cleared may be accomplished manually by the technician or by an automated mechanical clearing device (not shown).

As shown in FIG. 7, drawer 14 in the secured or locked position is positioned so that compartments 50, 52 and 54 are respectively aligned with and associated with medication identification sensors 154A, B and C. Likewise, sub arrays 124, 126 and 128 when used are respectively aligned with compartments 50, 52 and 54 of drawer 14 with first and second dividers 46 and 48 respectively aligned with the boundary between sub arrays 124 and 126 and the boundary between sub arrays 126 and 128. Thus, when transmitter 112 is activated to produce light beams 122 (FIG. 3A), the receiving elements of sub array 124 and the light beams 122 received thereby are associated with compartment 50, while the receiving elements and the associated light beams of sub array 126 are associated with compartment 52 and the receiving elements and light beams associated with sub array 128 are associated with compartment 54.

As shown in FIG. 9, the technician, pharmacist or other operator of system 10 may place a finger 196 on finger pad 152 (Arrow D) in order to identify whether the person is authorized to use system 10 although the user may log on to computer 26 in a standard manner which may include the use of a password. In addition, fingerprint reader 150 or another bio-ID mechanism provides a positive identification of the particular user of system 10. If the fingerprint reader or other mechanism identifies an authorized user, the computer program run by computer 26 proceeds with the rest of the process and also records the user's identification so that it can be determined subsequently who filled the drawer or was responsible for doing so. FIG. 9 also shows that once drawer 14 is secured within containment device 18, patient identification and information access sensor 140 reads (dashed lines) identifier 60 on label 58 to identify the patient and/or medication associated with the given drawer 14. The patient identification is communicated to computer 26 whereby the logic circuitry of the computer program accesses from the computer database pertinent information about that patient including all the medications 12 that are to be dispensed to the patient during a given day in accordance with a medical prescription. The prescription and thus database may specify only a single unit dose of a medication or multiple unit doses, and may or may not include different medication types. Where system 10 is being used to fill the drawer or other medication container of a storage cabinet or dispensing cabinet for the purpose of stocking or re-stocking, identifier 60 would be associated with a specific medication which does not include a specific patient. In this case, identifier 60 may thus signal the computer program such that it retrieves from the database the specification for a single medication type along with the number which is needed to stock or re-stock the medication container of the cabinet. The reading of identifier 60 may also trigger the response from the computer program described above as having been triggered by movement of plunger 184, that is, activation of the drop sensor and so forth.

Figure 9A:
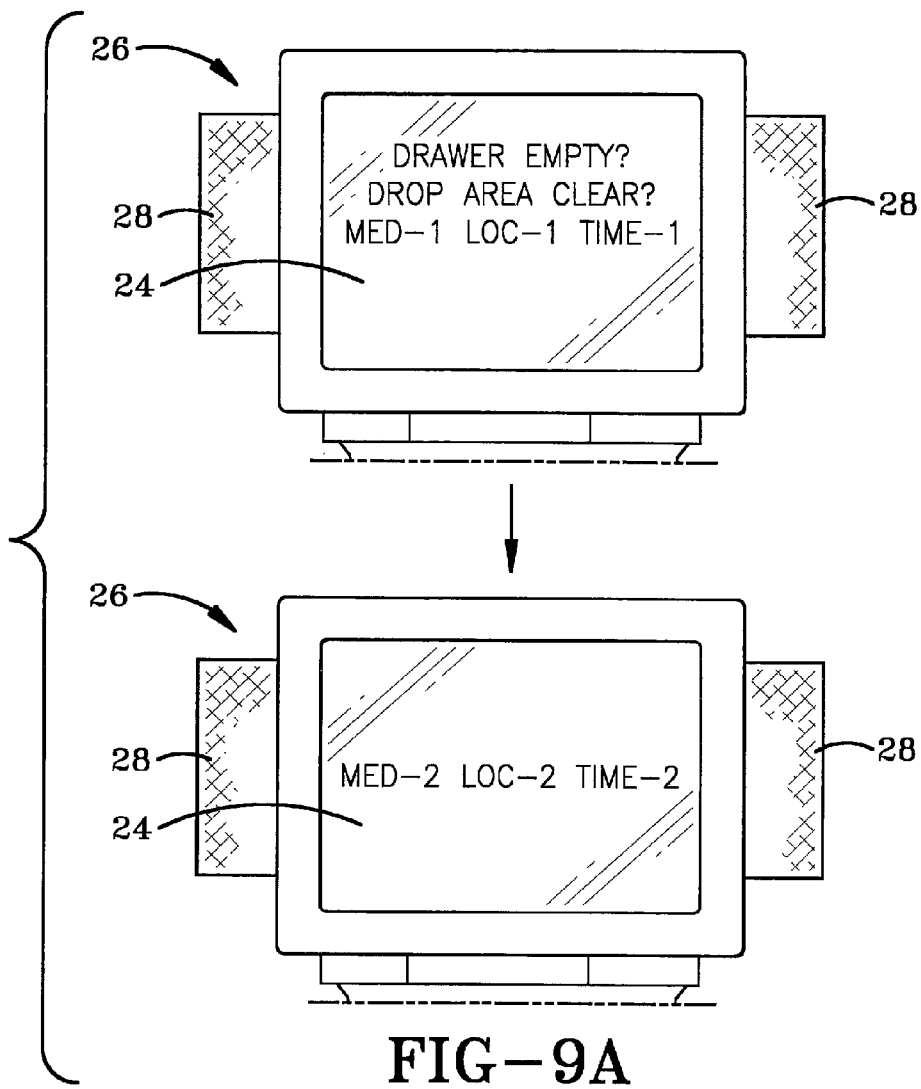
FIGS. 9A and 9B are diagrammic views showing alternate ways of displaying the patient's medication profile on the computer screen.
Figure 9B:
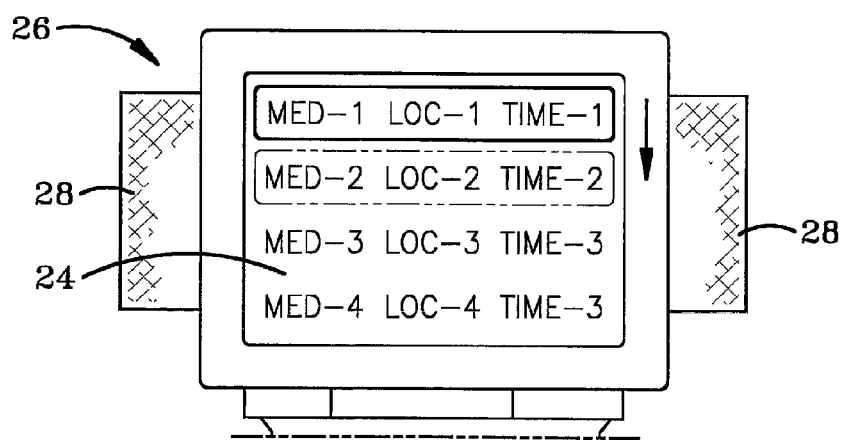

The patient's daily medical prescription or medication profile is typically displayed (FIGS. 9A-9B) on screen 24 so that the technician can read the various medications to fill drawer 14. The medication list may specify one or more medications and may be displayed a single medication at a time or may be displayed with a plurality of medications wherein, for instance, one medication at a time is highlighted. The former scenario is illustrated in FIG. 9A with an upper and lower computer in which the upper computer 26 illustrates the single listing of the first medication MED-1 on display screen 24 and the lower computer 26 illustrates a subsequent display of a second medication MED-2 on display screen 24. The latter scenario is illustrated in FIG. 9B which shows the medication profile including MED-1 through MED-4 with MED-1 being initially highlighted as illustrated by the solid line rectangle around MED-1 and MED-2 subsequently being highlighted by the dashed line rectangle around MED-2. In the highlighting version, only one medication is highlighted at a time. The technician follows the medication list on screen 24 one medication at a time. Thus, the technician will read either a single listed medication on the screen (FIG. 9A) or a medication which is highlighted (FIG. 9B) and then retrieve that medication 12 from one of storage bins 20 (FIG. 1).

The medication profile on screen 24 also indicates the location of the medication to be retrieved and the correct time period during which the medication is to be dispensed to the patient so that the technician knows from which bin to retrieve the medication, which of sensors 154 to use and which of compartments 50, 52, and 54 is to receive the medication. This is illustrated in FIG. 9A wherein the upper computer 26 displays on its screen 24 "MED-1 LOC-1 TIME-1" such that MED-1 is in a first column, LOC-1 is in a second column and TIME-1 is in a third column all aligned on a common line or row and wherein LOC-1 represents the location of MED-1 and TIME-1 represents the time period during which the medication MED-1 is to be dispensed or administered to the patient. The lower computer 26 of FIG. 9A shows a similar setup in which LOC-2 and TIME-2 respectively represent the location of medication MED-2 and the time period during which it is to be dispensed or administered. This is similarly illustrated in FIG. 9B. While TIME-1 and TIME-2 and so forth may specifically spell out the time period for administration of the associated medication, it also may represent in the alternative or in combination one of sensors 154 and/or one of compartments 50, 52 and 54. For example, instead of listing the time on display screen 24, one of sensors 154 may be specified so that the technician knows to use that sensor in scanning the corresponding medication and to drop the medication into the compartment 50, 52 or 54 associated with the given sensor 154. Likewise, one of compartments 50, 52 and 54 may be indicated on display screen 24 instead of or in combination with an indication of which sensor 154 to use and the associated time period. Another option which may be used alternately or in combination with these concepts is to provide an indicator on or adjacent the respective sensors 154 and/or compartments 50, 52 and 54 to indicate to which of these sensors and compartments is to be used. For instance, the computer program may be configured to turn on a light adjacent the appropriate one of sensors 154 and/or one of the compartments of drawer 14 when a given medication is listed on screen 24 in order to direct the technician to use the proper scanner and medication compartment for the displayed or highlighted medication.

In the above illustration, screen 24 provides a visible communication in the form of text or other symbols which may be read by a technician to communicate for example the requirement for an empty drawer check or a drop area check along with the specification of a given medication, its storage location, its dispensing time and/or which sensors are to be used to scan the medication and which compartment the medication is to enter. Alternately or in combination, other prompts or indicators may be provided to communicate the need to perform the given tasks or identify the medication, location and so forth. For instance, the computer program may be configured to cause audible messages to sound through speakers 28 or the like. Such an audible prompt, indicator or communication may simply be in the form of a recorded spoken phrase or sentence such as "Drawer empty?"; "Is the drop area clear?"; "Medication 1, location 1, time 1"; "Retrieve medication 1 from location 1, scan it with scanner 1 and drop it in compartment 1"; or other like messages. As noted above, such audible messages may be used in combination with the visible prompts on the computer screen or may be used without such visible prompts or messages.

Figure 21:
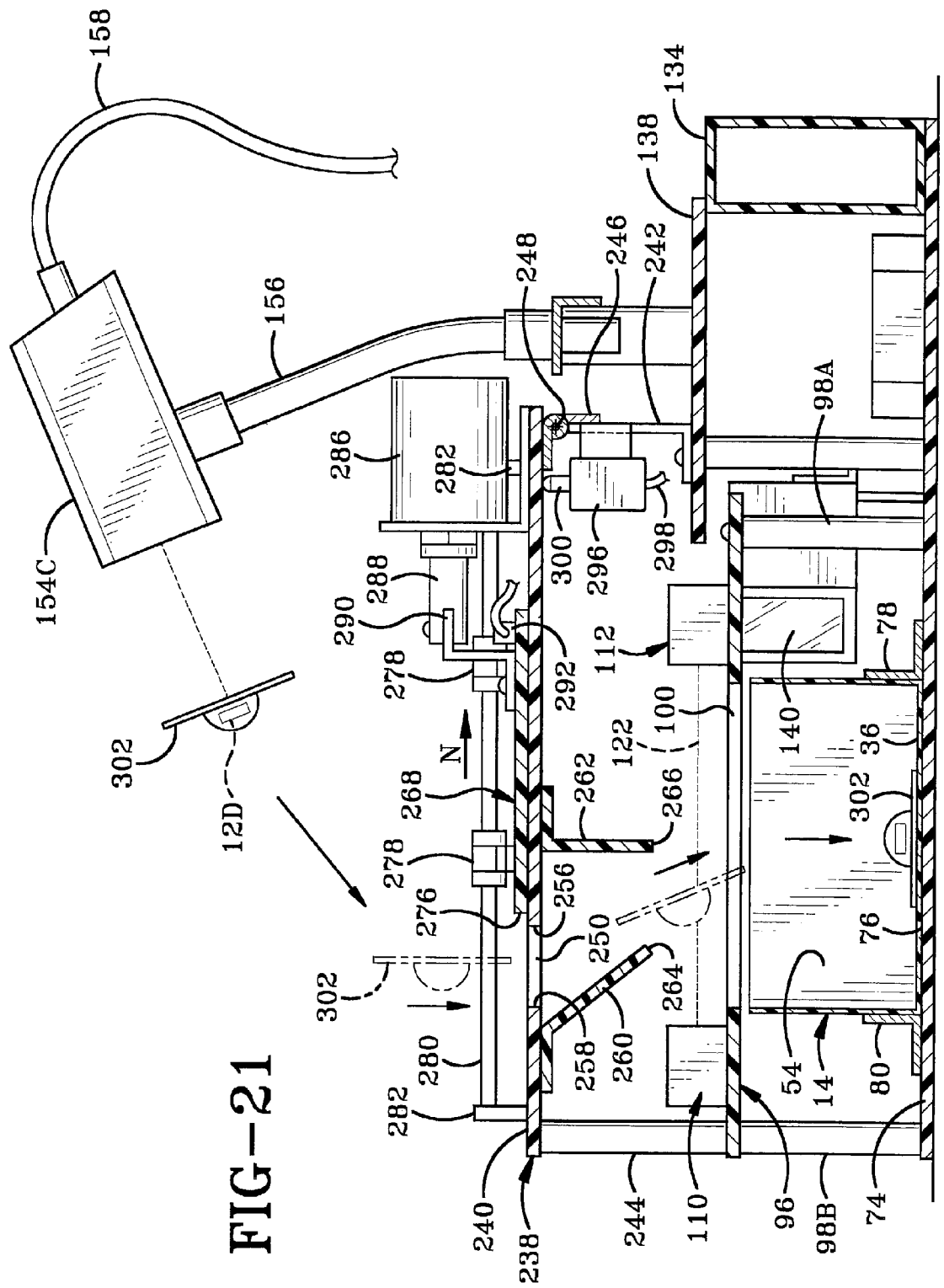
FIG. 21 is a sectional view similar to FIG. 19 and illustrates the process shown in FIG. 20 and further illustrates the travel of the medication through the entry slot past the entry sensor and into the patient drawer.

Once the appropriate medication—most typically as a unit dose—has been retrieved from its storage location, the technician will position the medication such as a pill shown at 12A in FIG. 10 adjacent the medication identification sensor 154 associated with the time period indicated in the patient profile so that a medication identifier 198 on medication 12A may be scanned or read (dashed lines) by the appropriate sensor, shown in FIG. 10 as sensor 154A. Identifier 198 is typically a bar code or another suitable machine readable identifier which may be connected to the medication directly (FIGS. 10, 15) or indirectly on its packaging or the like (FIGS. 11, 21, 25). Sensor 154A sends a signal to the CPU of computer 26 so that the computer program can determine whether the medication 12A is the correct medication in accordance with the patient profile. "Pick sensors", such as light curtains, may also be positioned adjacent respective pick locations like bins 20 to indicate from what location the scanned medication came or was "picked", for instance, which assigned pick location or bin 20, or another location which was not assigned. If medication 12A is the correct medication, a correct or good audible scan tone is sounded via speakers 28 (FIG. 1) to indicate that medication 12A is the correct medication. If not, an incorrect or bad audible scan tone is sounded via speakers 28 to indicate that medication 12A is the incorrect medication. Thus, the good and bad scan tones are distinct from one another so that the technician can easily discern between the two.

The correct and incorrect scan tones are but one form of correct and incorrect medication indicators which may be used in the present invention. Other such indicators may be used alternately or in combination with these audible tones, such as light or another visible indicator. For example, a correct medication scan may be indicated by a green light while a bad medication scan may be indicated by a red light, or a correct scan may be indicated by a flashing light and an incorrect scan may be indicated by a steady light. Similarly, one or more small display screens associated with sensors 154 could be controlled to display correct and incorrect indicators without illuminating a light source. For instance, a liquid crystal display of black lettering or the like may be used wherein the correct indicator might for example be indicated by "Yes" or "Y" while the incorrect indicator might be displayed as "No" or "N". Correct and incorrect indicators might also utilize movement of a pointer or flag, wherein, for example, the pointer can move in one direction to provide a correct indicator and in another direction to provide an incorrect indicator, or wherein two different colors may be used respectively as said indicators. Any suitable indicator may be used for this purpose.

If medication 12A is the correct medication, the technician then drops medication 12A (Arrow E) into the associated compartment 50 of drawer 14. As medication 12A drops downwardly, it interrupts typically for a small fraction of a second one or more of the light beams as indicated at 122A in FIG. 10 so that said light beams momentarily do not pass through the region indicated at 200 to the corresponding photoelectric sensors of receiving unit 114. This interruption of one or more of the light beams causes a signal to be sent from receiving unit 114 to computer 26 indicating that medication 12A has been dropped through the sensing field and into compartment 50. The computer program is set up to require that medication 12A be dropped through the plane of detection of light beams 122 within a relatively short period after being scanned by sensor 154A. Typically, it only takes one or two seconds from the time that the technician scans the medication and hears a good drop tone until the medication passes through the plane of detection of the light beams. Thus, the computer is typically programmed for such a short period although somewhat larger allowance is usually given such as up to 3, 4 or 5 seconds or possibly a little bit more although usually not more than 6-10 seconds and typically not more than 5 seconds. If a proper or good drop of medication 12A occurs, a correct or good drop tone is sounded via speakers 28 to that effect. A good drop tone is normally sounded for a drop which is associated with a good scan via sensor 154, which thus means that medication 12A is the correct medication and that the drop occurred within the predetermined time period subsequent to the scan. As discussed above with regard to the correct and incorrect medication indicators, drop tones are but one type of indicator which may be used with respect to the entry sensor or drop sensor to indicate correct or incorrect drop or entry indicators. Other types of indicators may be used as discussed above with respect to correct and incorrect medication indicators.

In addition, as discussed previously with reference to FIG. 3A, the entry or drop sensor may be set up to ascertain whether the medication was dropped through the appropriate portion of the sensing field associated with the correct time period. According to such a scenario, a correct drop tone would be sounded if medication 12A were dropped through the light beams 122 associated with sub array 124 (FIG. 3A) which is associated with the time period corresponding to compartment 50. However, when the medication is supposed to enter compartment 50, a bad drop may be indicated by a bad drop tone if medication 12A is dropped through the light beams associated with sub arrays 126 or 128 and the time periods associated with compartments 52 and 54. In addition, a bad drop tone may sound for a drop of medication 12A which was indicated to be the incorrect medication when scanned by sensor 154A. Furthermore, a bad drop tone will be sounded when the plane of detection is broken when no scan has been previously performed indicating that a drug or medication should be dropped into drawer 14. Thus, any unauthorized object passing through the plane of detection, whether a medication, part of the technician's hand or otherwise, will be deemed to be a bad drop and the bad drop tone will sound if a corresponding good medication scan has not first occurred.

If a pill or other object is dropped into the drawer or the plane of detection is broken without a good scan, the bad drop is recorded on a pharmacist's error report so that the pharmacist is made aware of the error during review of the report and will subsequently check the entire drawer to verify the accuracy of the medications therein. Similarly, if a bad scan tone is sounded due to a bad scan and the technician nonetheless drops the wrong medication into the drawer (thus producing a bad drop tone), a record of the error is produced on the pharmacist's error report so that pharmacist may check the drawer. However, if a bad scan tone is sounded and the medication is not dropped, the computer program clears the medication (typically within the short period normally allowed for dropping the medication) so that the correct medication can be subsequently scanned without producing a record of any error since the incorrect medication never entered the drawer. The scanning and dropping procedure utilizing sensors 154A-C and the drop sensor is repeated for each dose until all of the doses for a given medication are scanned and dropped. The computer program automatically advances sequentially to the next medication (MED-1, MED-2, MED-3, etc.) for the repeated process of scanning and dropping until all the medications for a given patient have been scanned and dropped into the associated drawer 14 within the appropriate compartments 50, 52 or 54 associated with the time periods indicated by the computer program. Where no error occurs which produce an error report to the pharmacist for a given drawer or container, the prescription may thus be filled without verification by the pharmacist and also administered to the patient without verification by the pharmacist.

With continued reference to FIG. 10, the scanning and dropping process is described with more specific reference to the use of box 164 and sensor enablement device 146. One concept of the invention is to scan and drop various medications with a single hand in order to help reduce errors which may be introduced by a second hand, including the inadvertent dropping of the medication prior to scanning or the inadvertent dropping of another medication or object into the drawer which would produce a bad drop tone. The invention provides two distinct ways of providing for such a same hand scanning and dropping procedure. One way is by providing physical barriers to limit access to the space adjacent drawer 14, sensors 154 and light curtain 110. For instance, box 164 may provide a barricade wall 166 along with the possible use of a manual access opening 178 through an access wall 172. Barricade wall 166 helps to serve this purpose by providing a barricade between the natural position of the right and left hands of the technician which are respectively indicated at the left hand finger 202 and right hand 204 in FIG. 10. When the user or technician faces containment device 18 and positions right hand 204 for the purpose of scanning and/or dropping medication 12A, the left hand 202 is naturally on opposite side of barricade wall 166 from right hand 204. Thus, an inadvertent movement of left hand 202 toward right hand 204 and the space above drawer 14 is generally blocked by barricade wall 166. In addition, access opening 178 allows for the easy insertion of right hand 204 and may also be large enough for the insertion of both hands, but nonetheless discourages the use of both hands within interior chamber 180 of box 164. Another option is to utilize a sensor enablement device 146 which must be activated by left hand 202 to enable the use of sensors 154 which otherwise will not scan the medication. In the exemplary embodiment, the left hand finger 202 must depress button 148 (typically closing an electrical circuit) of device 146 to signal the computer program to enable the use of scanners 154. If button 148 is released at any time, its internal spring biases it automatically to its non-depressed inactivated position whereby scanners 154 will not operate to scan the medication. This configuration thus also keeps the hands separated from one another so that only a single hand is positioned over drawer 14. Although the activation of device 146 may be used to signal the computer program to enable scanners 154 as noted above, it may also control scanners 154 directly without involvement of the computer program by, for instance, turning on the scanning light or the like of the scanner.

Figure 12:
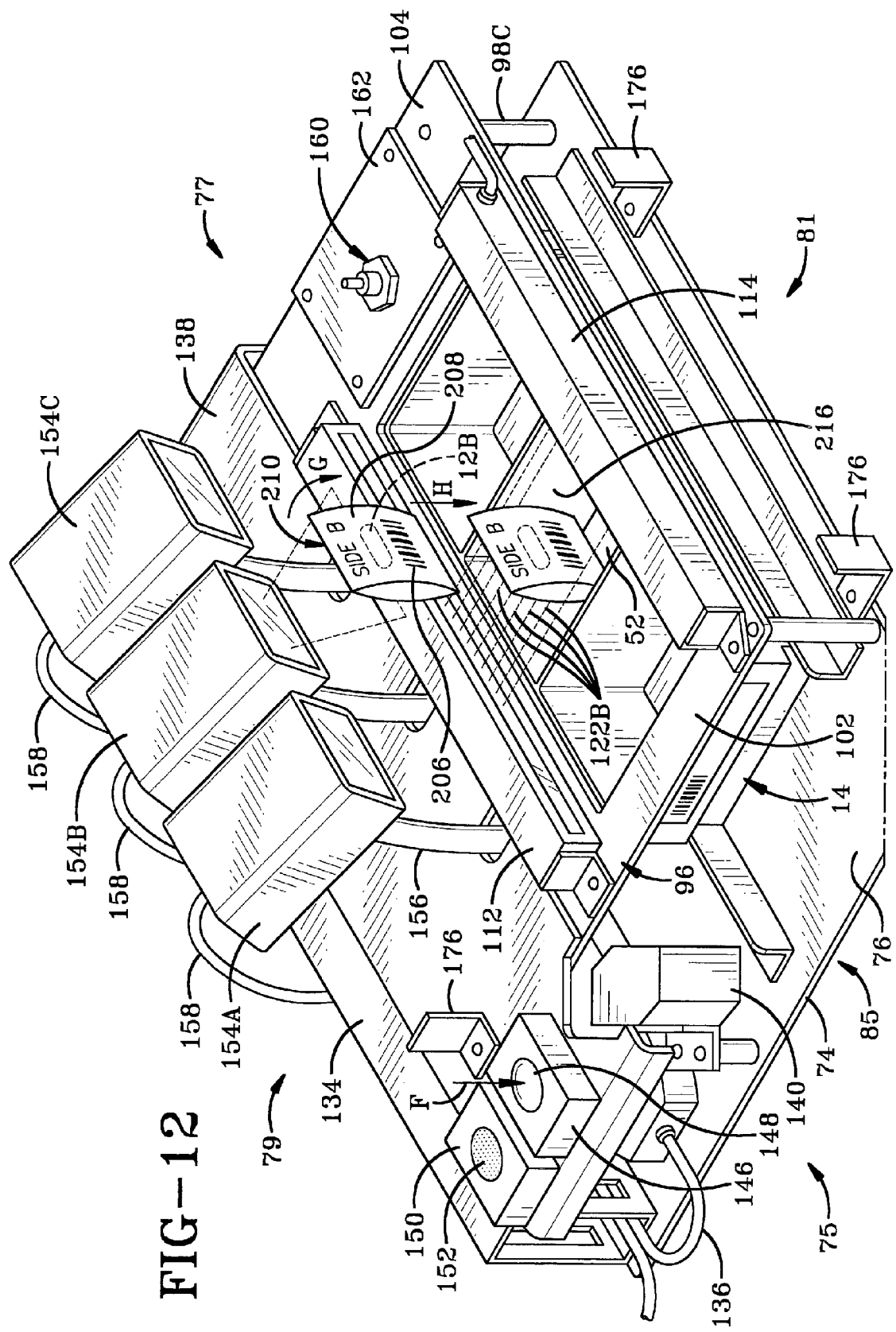
FIG. 12 is similar to FIG. 11 and shows the scanner scanning a second label on the medication package and the package moving through the light curtain into the center compartment of the drawer.

FIGS. 11 and 12 represent the process of using caution labels for partial tablets or pills and also for multiple pills per dose. For instance, computer 26 may display a patient medication profile requiring a dose which utilizes only a part of a pill or tablet or which utilizes multiple pills or tablets. In this case, the computer program signals printer 31 (FIG. 1) to print a caution label to indicate that the dose includes only a part of a pill or tablet or multiple pills. The label also includes a partial dose identifier 206 (FIG. 12) (or multiple pills per dose identifier) such as a bar code or other machine readable identifier. More particularly, identifier 206 of the caution label is shown on one side 208 (Side B) of a bag or package 210 in FIG. 12 which in FIG. 11 faces and is scanned by sensor 154B to be acknowledged by the computer program. FIG. 11 thus shows a second side 212 (Side A) of package 210 which faces away from sensor 154B and on which a medication identifier 214 is displayed which is indicative of the medication 12B within package 210. It is noted that button 148 of sensor enablement device 146 remains depressed as indicated by Arrow F to enable sensor 154B to scan identifier 206. Once partial dose (or multiple pills per dose) identifier 206 has been scanned, package 210 is flipped over as indicated at Arrow G in FIG. 12 so that identifier 206 faces away from sensor 154B and identifier 214 faces and is scanned by sensor 154B, as enabled by the continued depression of button 148. If labels 206 and 214 are properly scanned, good scan tones are sounded respectively by speakers 28 and the technician then drops package 210 through the plane of detection into intermediate compartment 52 of drawer 14. As previously discussed with respect to the dropping of medication 12A in FIG. 10, package 210 interrupts light beams 122B shown in FIG. 12 to produce a region 216 of no light beams. Once again, the lack of reception of these light beams by receiving mechanism 114 signals the computer that a drop has occurred. If the sub arrays of receiver unit 114 are used, the interrupted beams 122B are within sub array 126 indicative of the time period associated with sensor 154B and compartment 52 of drawer 14. As noted above, if such sub arrays are used, a bad drop tone may be sounded if the medication or package is dropped into the wrong compartment of drawer 14. Similarly, a bad scan tone may be sounded if the technician attempts to scan the medication or package identifier with the wrong sensor 154.

Ultimately, the technician will fill drawer 14 with the various medications listed on the patient's medication profile (FIGS. 9A-9B) in accordance with a medical prescription in order to fill the prescription. Typically, this is done unit dose by unit dose of various medications in a serial fashion. Usually a unit dose is signified by a single pill, tablet or capsule although other unit doses such as those in liquid form are also used, as discussed further below. As noted above, a given prescribed dose may involve the use of a partial unit dose or multiple unit doses. Although a partial unit dose may be prescribed, the corresponding medication is typically verified in its unit dose form along with the corresponding caution label discussed above so that the unit dose may be broken or the like just prior to administration to the patient. Where a prescribed dose includes two or more unit doses of a given medication, that prescribed dose of multiple unit doses may be enclosed in a package such as package 210 in FIGS. 11 and 12 whereby the identifiers on the package represent the multi-unit dose in contrast to a single unit dose. Especially where system 10 is used in a hospital setting or within another health care facility having resident patients, the medications entering the patient drawer or other patient specific container typically will contain only medications which have been prescribed for a specific 24-hour period.

Once a given drawer 14 has been filled with the one or more medications indicated in the corresponding patient's profile as displayed on screen 24 of computer 26, the computer program automatically unlocks locking mechanism 160 (FIG. 13) by electromagnetically activating the solenoid thereof to move plunger 184 upwardly (Arrow J) to its unlocked position. It is noted that the computer program typically will not allow locking mechanism 160 to be unlocked until drawer 14 has been properly filled in accordance with the medical prescription or stocking order, which may require that the pharmacist check the drawer if an error is identified during the filling process. When mechanism 160 is unlocked, plunger 184 is disengaged from locking surface 72 of crossbar 66 so that crossbars and 66 and 68 may pass beneath plunger 184 as drawer 14 is manually slid forward (Arrow K) out of drawer-receiving space 90 of containment device 18. As drawer 14 is being removed, the computer program will check to see if the drop sensor is interrupted or broken for too long a period of time, in which case an error tone is played and an error is recorded to that effect to be printed on the pharmacist's error report. It is noted that if the drop sensor is broken for too long a period at any time when drawer 14 is in its secured position in device 18, a similar error tone is sounded and a similar error is recorded on the error report. Once drawer 14 is removed from device 18, it is reinserted in its location within cart 16 (FIG. 1) and the drawer fill process is completed for each of drawers 14 within cart 16.

Locking mechanism 160 is used in part to help ensure that drawer 14 remains in its substantially stationary filling position throughout the filling process. As previously noted, the movement of the plunger locking mechanism 160 may send a signal to the computer program in order to activate sensors 154. It may also send a signal simply indicating that a drawer has been inserted into the receiving space of containment device 18 so that the computer program recognizes this and does not allow the removal of the drawer until the filling process is complete. However, a locking mechanism which secures the drawer within device 18 may be replaced by another type of sensor which recognizes that drawer 14 is in its filling position without locking the drawer into place. For instance, any suitable sensor may be used to signal the computer program that a drawer has been inserted into its filling position and to recognize if the drawer has moved out of the filling position. Under ordinary circumstances, drawer 14 will sit in a stationary position absent a force on the drawer supplied by the technician or otherwise. Thus, the computer program may be configured to go through the entire filling process as long as this alternate sensor indicates that the drawer or the container remains in its filling position. Thus, if the drawer is moved out of the filling position and sensed by the sensor to that effect, the computer program may be configured to produce an error report or to require that the filling of the drawer start over again.

As described above, a technician or other person may perform all the various tasks of the filling process. However, system 10 is also configured to be used with a robot which performs some or all of the tasks of the filling process. When a robot is used, it is in electrical communication with computer 26 whereby it may be controlled in accordance with the computer program. The use of a robot or automated machinery may alter some of the processes discussed above, some of which will be noted below. The robot may be configured to remove patient drawers 14 from cart 16 and to insert them into containment device 18. While the robot may be configured to perform an empty drawer check for instance by turning the drawer upside down to empty it of any items, it may be desired that a technician or other person perform the empty drawer check alternately or in combination with any such function of the robot. This may be true for the drop area check as well. If the system is configured without the need for a person to perform these checks, the inquiry or prompt for these checks which is typically displayed on screen 24 (FIG. 9A) may be eliminated. Similarly, when a robot is used to pick or select the medications from a storage location, scan the medications with sensors 154 and drop the medications into the drawer, the medication profile displayed on screen 24 or prompt or indicator which would otherwise be communicated to the technician can be eliminated if desired. Such visual or audible indicators would not be necessary in order for the robot to operate properly. Instead, the computer program is typically configured to communicate directly to the robot to control its movements in accordance with the medication profile or stocking order. As previously discussed, pick sensors may be used adjacent the storage locations or bins from which a medication is picked to verify whether a given medication was picked from the location specified by the computer program. If the robot or technician picks a medication from the wrong storage location, the computer program may indicate an error. Where the robot is used, it may be controlled to return the medication to the storage location and subsequently pick from the correct location. In the case of a technician or another person, a pick error indicator which is typically visible or audible as previously described may be used to likewise inform the technician of the error so that the medication can be returned to its storage location and the proper medication can be pulled from the correct storage location. As with the technician, the robot will scan the medication using one of sensors 154 to properly identify the medication. If it is the correct medication, then the robot will drop the medication into the drawer through the entry sensor. If not, the computer program is configured to prevent the robot from dropping the medication in order to present an error report due to an incorrect entry into the drawer. In this case, the computer program may be configured to recognize the storage location from which the incorrect medication has been picked, and to control the robot to return this medication to its proper storage location. If a technician has scanned an incorrect medication, the computer program in addition to producing an incorrect medication indicator may also provide a visual or audible indicator instructing the technician where to return the medication. If a robot drops the incorrect medication, the computer will record an error which will be produced typically in a report as previously discussed for the pharmacist. However, the visual or audible incorrect entry indicator which is used with a technician or other person may be eliminated if desired when the robot is performing this task. While the robot may be configured to function with box 164 such that a robotic arm of the robot may be inserted and withdrawn from access opening 178 of access wall 172, certain portions or all of box 164 may also be eliminated with the use of the robot. For instance, there may be no need for barricade walls 166 inasmuch as the use of a robot eliminates the concern of keeping the right and left hands of the technician separated from one another during the filling process. In addition, sensor enablement device 146 may be eliminated with the use of the robot. However, it may be desired to retain cover wall 174 or other walls of box 164 in order to help prevent unauthorized items from accidentally being dropped into drawer 14. Once a given drawer is filled, the robot may be controlled to remove the drawer from containing device 18 and insert it into cart 16.

Figure 13A:
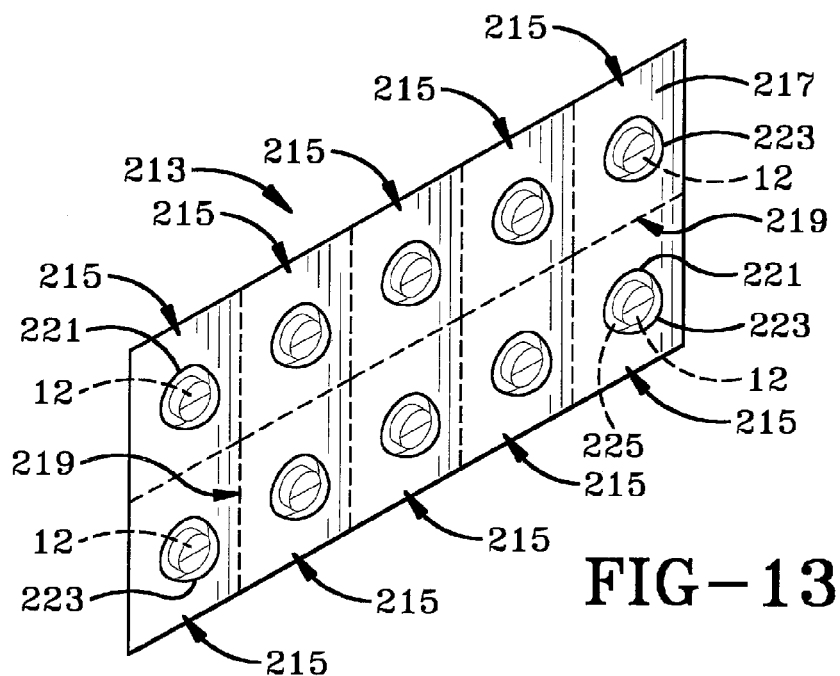
FIG. 13A is a perspective view of one form of a multi-dose package of medications.

The process thus far has been described primarily with reference to the filling of a patient drawer although as previously noted, system 10 may be used for the filling of a storage or dispensing cabinet in order to fill a medication specific container with a specific medication in bulk in accordance with a stocking or re-stocking order. Although the filling of such a bulk compartment may involve placing individual pills or other unit doses of the same type one by one into a given bulk compartment, this process may also involve filling the bulk compartment with various types of packaging which include multiple unit doses. For instance, such packaging may include a package which has individual units which are separably connected to one another whereby the entire package may be used for stocking or re-stocking the medication compartment and the individual units may be subsequently separated from one another prior to administration of the medication. FIG. 13A shows an example of such a multi-dose package 213 which includes 10 unit dose packages 215 which are individually separable from one another. More particularly, package 213 includes a generally rectangular flat sheet 217 typically formed of plastic or another suitable material which has various perforations or perforation lines 219 serving as tear lines such that sheet 217 may be torn along the lines in order to separate each unit dose package 215 from the others. Holes 221 formed in sheet 217 are respectively associated with corresponding unit dose packages 215 and medications or pills 12. A transparent bubble 223 extends outwardly from the sheet 17 in communication with each hole, and a laminate layer 225 of foil, paper or other similar material is laminated on the opposite side of sheet 217 so that pill 12 is contained within the space defined by transparent bubble 223 and the portion of layer 225 which covers the respective hole 221. Pill 12 may be accessed by pushing on transparent bubble 223 to force pill 12 through the portion of layer 225 covering hole 221. Where a multi-dose package such as package 213 is used to fill a medication compartment, the computer program in response to reading identifier 198 on package 213 may be configured to recognize that the package contains multiple doses or pills 12, which in the exemplary embodiment is ten as previously noted. Alternately, the medication may be scanned and the technician may make an entry recognized by the computer program to indicate that a given number of pills or unit doses are associated with the package 213. In any case, once the medication has been identified by the appropriate sensor 154, package 213 is moved into patient drawer 14 or other medication container whereby its entry is sensed by the entry sensor so that the computer program verifies the entry. The computer program may be configured to specify the number of multi-dose packages needed to stock or re-stock a medication compartment or for the filling of a patient drawer. Thus, the computer program may be configured to cause the medication profile displayed on screen 24 to indicate, for example, "three multi dose packages of Med-1" similar to the displays shown in FIGS. 9A and 9B.

Once cart 16 has been filled, several computer generated reports are typically produced which are to be reviewed by the pharmacist. Amongst these is an "Orders Not Filled" report which indicates any medication that was missed during the fill of a given drawer 14. A "Fill List Errors Report" is also produced to inform the pharmacist which drawers the pharmacist needs to check by hand (visually) to ensure the accuracy of the medications therein. A "Fill List Detail" report is produced for review by the pharmacist and lists every medication which was scanned for each patient along with any errors. In addition, an "Orders Without Drug Location" report provides a list of all the drugs or medications that were pulled or retrieved from the main pharmacy of the hospital instead of from the assigned pick areas which are represented by storage bins 20 in FIG. 1. Further, a "Pick Exception List" may be produced to indicate whether a given medication was picked from the correct picking area or storage bin 20.

The computer program is also configured to provide patient billing for the various medications once all the drawers 14 on a cart 16 are filled by a one button click. Thus, the computer program is configured to interface with the billing program of the pharmacy and/or hospital to charge the patient for the medications. Any medications which were placed in the various patient drawers 14 and were not used may be returned. These returned medications may be scanned by sensors 154 or the like to determine the appropriate storage bin to which they should be returned and also to update the billing by a single click to provide credit to the associated patient. In one embodiment, the medication which is scanned for return is displayed on the computer screen for a specific limited duration, at which time the program automatically clears the screen. The technician thus has sufficient time to read the display in order to determine where the medication should be returned, but does not have to touch the computer in order to clear the screen. Thus, the technician can simply scan the medication, read the screen and put the medication away without further action whereby the computer program not only indicates where the medication is to be returned but also automatically credits the patient's account. In the exemplary embodiment, the return location is displayed on the screen for about three seconds, although this duration may vary and is typically not more than about ten seconds long. If the technician is returning several medications, the computer program may also be programmed such that if the return location for a first scanned medication is still on the screen, the scanning of a second return medication may signal the computer program to clear the first return location from the screen and display the second return location.

Figure 14:
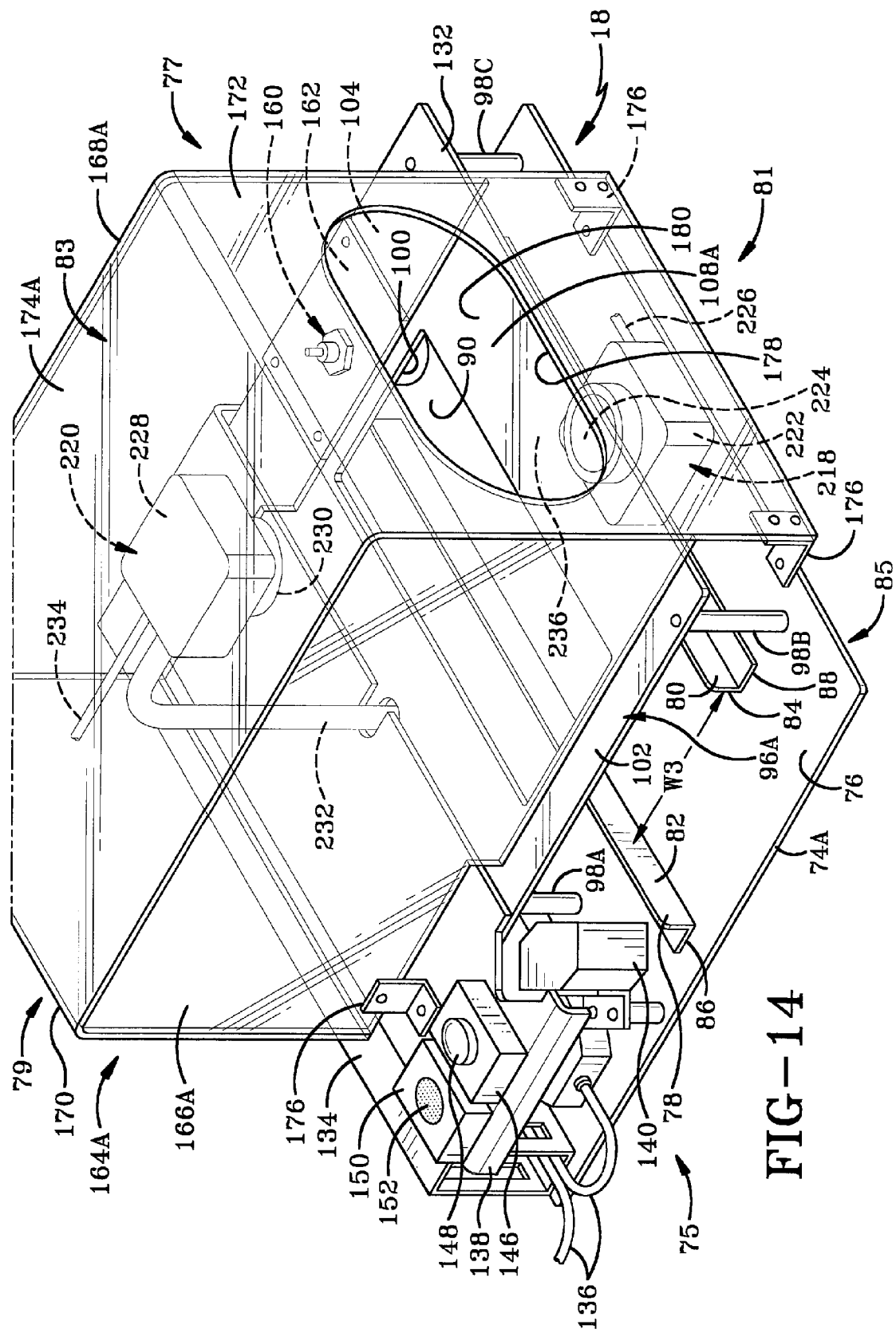
FIG. 14 is a perspective view similar to FIGS. 3 and 4 and shows an alternate sensor assembly for identifying medications and verifying their entry into the patient drawer.
Figure 15:
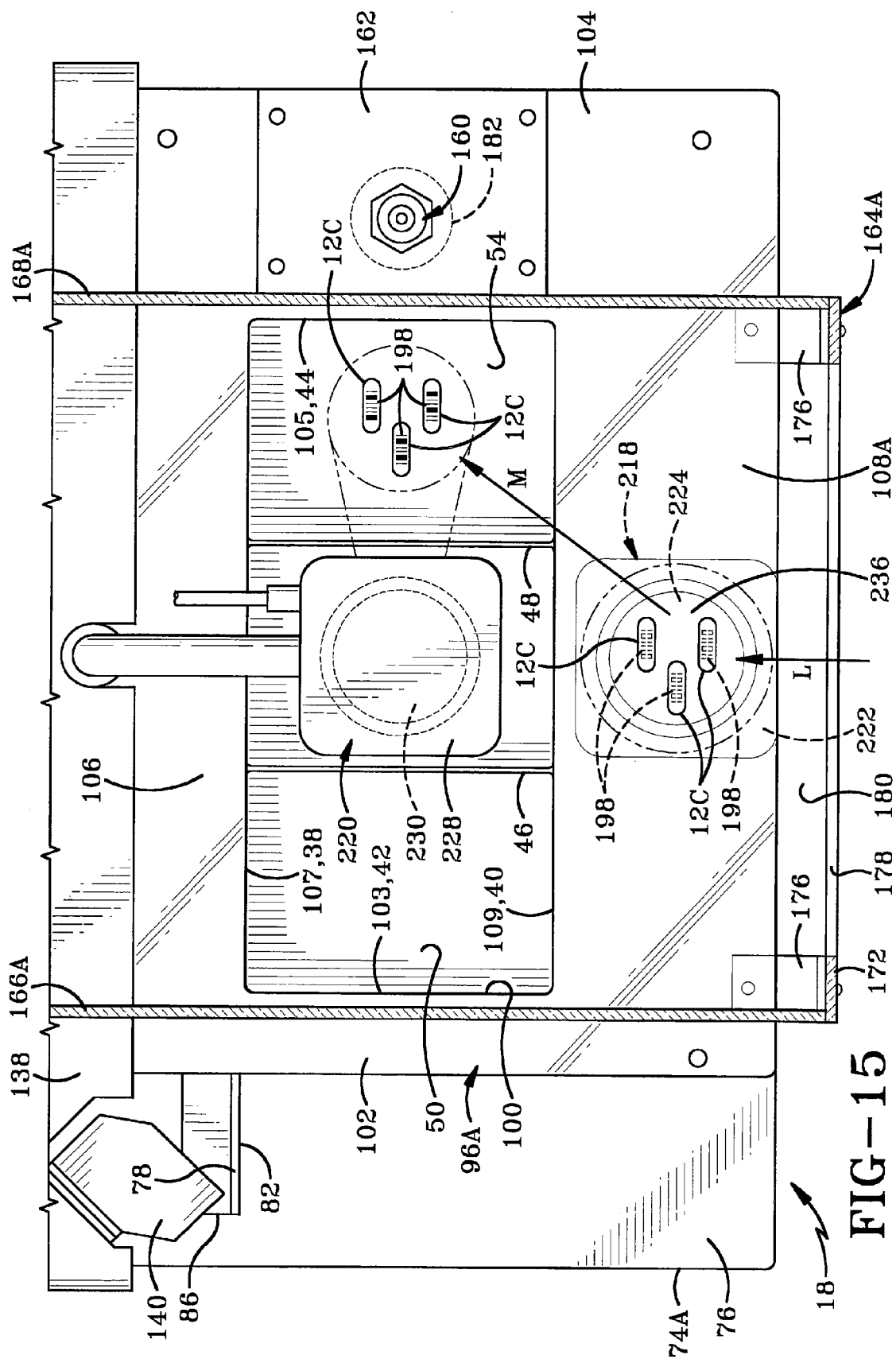
FIG. 15 is a top plan view similar to FIG. 7 and shows drawer 14 in the secured position and the operation of the alternate sensor assembly.

Referring now to FIGS. 14 and 15, an alternate sensor assembly is described. This alternate sensor assembly includes medication sensors in the form of a medication identifier camera 218 and an entry sensing or drop sensing camera 220 which serves in part as an entry sensor or drop sensor. The embodiment shown in FIGS. 14 and 15 does not include the light curtain or the like although the various options described with regard to the entry sensor or drop sensor of the previous embodiment may also be used in conjunction with the alternate sensor assembly. Some of the structure related to containment device 18 has been altered somewhat to accommodate the use of cameras 218 and 220. For instance, a bottom wall 74A is included which is analogous to wall 74 and is somewhat longer in the axial direction, extending further toward second side 81 away from drawer-receiving space 90. In keeping with this alteration, a transparent box 164A analogous to box 164 is included and is likewise axially longer than box 164. Thus, box 164 includes walls 166A, 168A and 174A which are elongated in the axial direction to a greater degree than their counterparts of box 164. In addition, an elevated transparent wall 96A includes a sidewall 108A which is axially longer than its counterpart. These dimension changes accommodate camera 218, which includes a housing 222 which is mounted on the extended portion of bottom wall 74A directly below sidewall 108A adjacent guide wall 80 toward second side 81 of the device. Camera 218 further includes an aperture or lens 224 which faces upwardly toward sidewall 108A of elevated wall 96A. Camera 218 is in electrical communication with computer 26 and an electric power source via an electrical wire 226. Sidewall 108A of elevated wall 96A includes a horizontal upper surface including a scanning location 236 which is typically directly above lens 224 of camera 218. Camera 220 likewise includes a housing 228 and a lens or aperture 230 which faces downwardly and is typically positioned directly over the center of medication access opening 100. A support arm 232 is connected to bottom wall 74A and housing 228 to support camera 220 in this position. Camera 220 is in electrical communication with computer 26 and an electrical power source via an electrical wire 234. As shown in FIG. 15, lens 230 of camera 220 is substantially centered above the center compartment 52 of drawer 14 when drawer 14 is in its secured position within containment device 18.

The operation of the alternate sensor assembly is described with reference to FIG. 15. Camera 220 is configured to perform the empty drawer check and the drop area check to ensure that drawer 14 is empty prior to the filling procedure and to ensure that the area around the drawer is also free of medications or other loose objects. Thus, instead of the technician providing this information, the computer program is configured to receive a signal from camera 220 indicating whether the drawer is empty and whether the drop area is clear. If not, the computer program will not allow the filling procedure to proceed. Once it is determined that the drawer is empty and that the drop area is clear, the technician (or robot) will proceed with filling the drawer in a manner similar to that previously described. However, the technician or robot will retrieve medications 12C from the appropriate storage bins and place them at the scanning location 236 (Arrow L) with respective medication identifiers 198 facing downwardly. Camera 218 is focused upwardly and is capable of sensing (dot-dash circle around location 236) the medication identifiers 198 through transparent wall 108A in order to identify whether medications 12C are the correct ones. Good or bad scan tones or other indicators are respectively produced in accordance with the process previously described. Camera 218 is capable of scanning a plurality of medications simultaneously so that a given set of medications (typically making up a single prescribed dose) may be moved into drawer 14 via a single motion of a technician's hand or robotic arm. Once medications 12C are identified as being the correct medications, the technician or robot moves the medications into drawer 14, for example into compartment 54 as shown at Arrow M by sliding the pills or medications along the upper surface of wall 108A or otherwise. Camera 220 senses that medications 12C have entered or been dropped into compartment 54 as indicated at the dot-dash lines in compartment 54 and extending from camera 220. Camera 220 is thus not only capable of determining whether the medications enter the drawer, but is also capable of determining whether the medications enter the proper compartment of the drawer. Good and bad entry tones or drop tones are sounded in accordance with the previous discussion.

Figure 16:
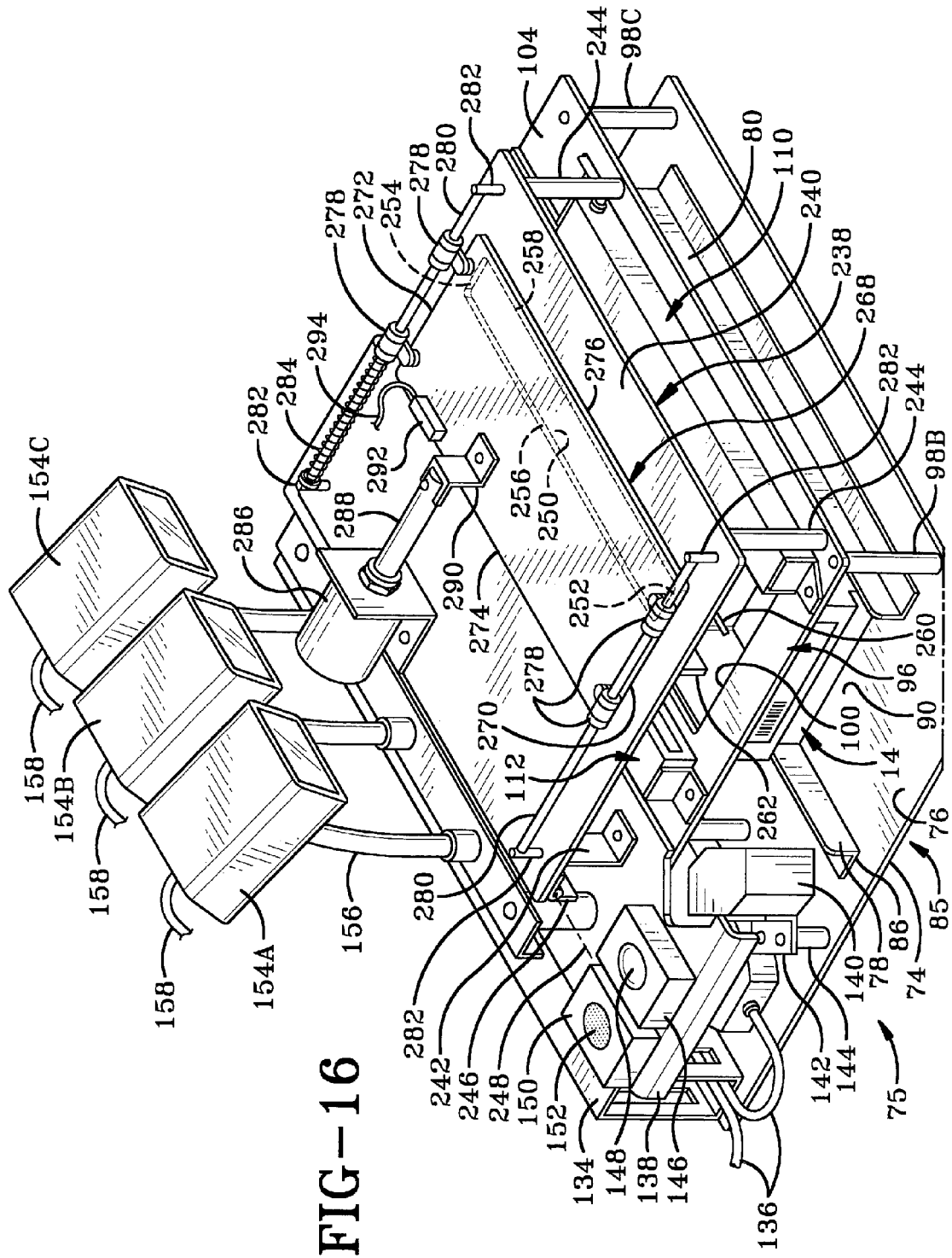
FIG. 16 is a perspective view similar to FIG. 3 shown without the transparent box or enclosure for clarity and shows the patient drawer containment device with an openable and closeable lid having a medication entry slot which may be covered and uncovered with a motorized cover.

Turning now to FIGS. 16-24, an additional modification to system 10 is described. As will be readily understood by review of the figures, the structure shown in FIG. 16 is substantially the same as that shown in FIG. 3 except for additional structure above elevated wall 96 which is used in further controlling the entry of medication or other objects into the patient drawer and thus helps to ensure 100 percent accuracy in filling the drawer so that a pharmacist need not verify the medications within a given patient's drawer or other medication container. FIG. 16 shows that light curtain 110 is used as the entry sensor or drop sensor, which was described in greater detail above. Presence sensing devices such as light curtain 110 vary in their ability to sense small objects which move quickly therethrough. The presence sensing devices which are capable of ensuring 100 percent verification of such small objects passing into the patient drawer are rather expensive. In an effort to minimize the cost of the present verification system, a less expensive light curtain may be utilized. While the accuracy of such a light curtain for verifying objects entering the patient drawer is fairly impressive, it has been determined that some small stray objects have been able to pass through the light curtain without being detected. Although this may occur less than one in a thousand times, the object of the present invention is to ensure 100 percent verification of the medications entering the patient drawer or other container. To that effect, the structure above elevated wall 96 has been added.

Figure 23:
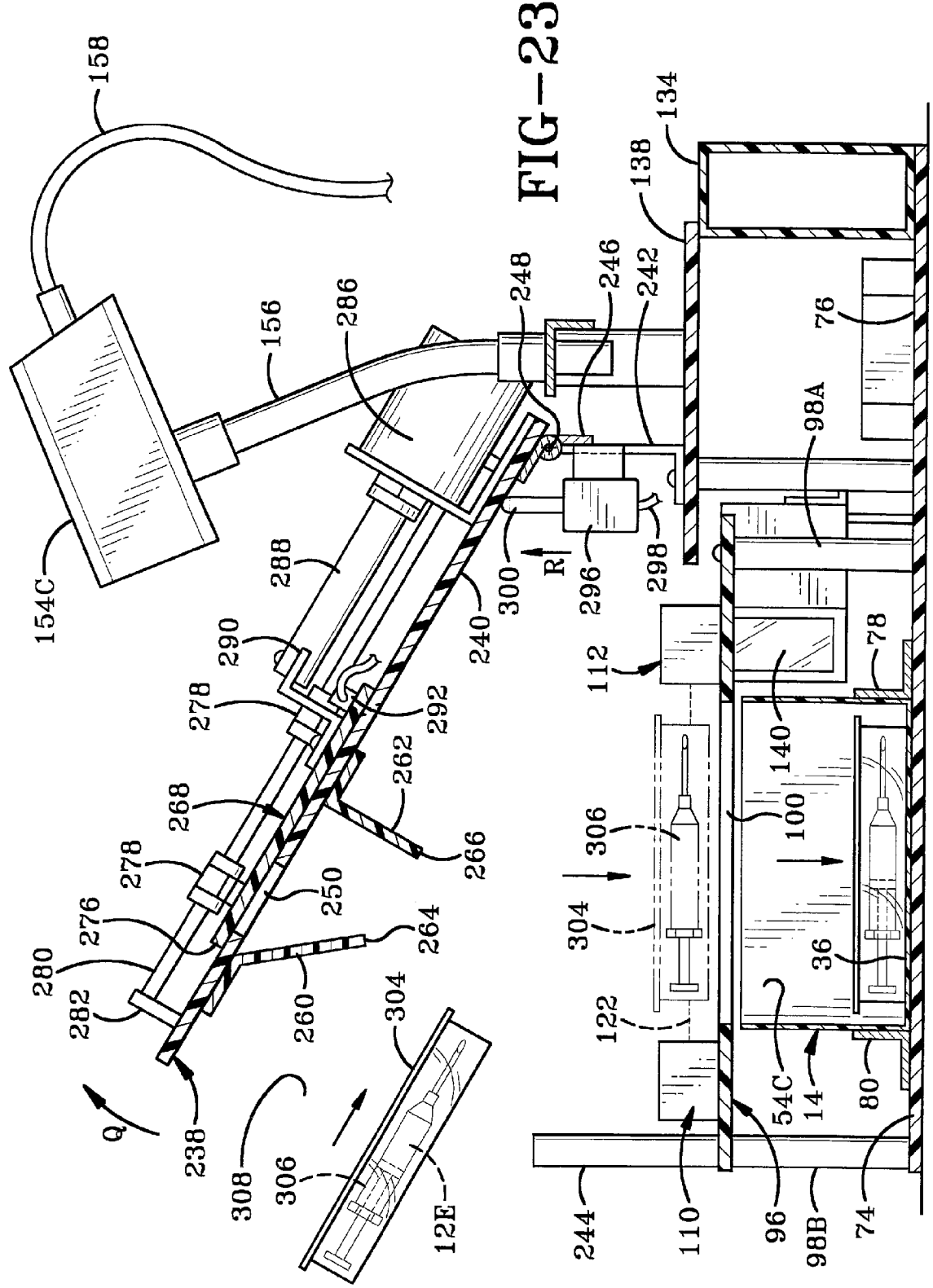
FIG. 23 is a sectional view similar to FIG. 21 and shows the lid being opened and the medication package with the syringe being placed into the patient drawer.

More particularly, this additional structure includes an openable and closeable lid 238 which includes a transparent, rectangular, flat and horizontal wall 240 which is spaced upwardly of wall 96 and supported in this elevated position by a set of first legs 242 and a set of second legs 244 each of which is rigidly secured to and extends upwardly from wall 96. First legs 242 are positioned on one side of access opening 100 while second legs 244 are on the opposite side thereof. A hinge 246 is mounted the upper ends of first legs 242 with wall 240 adjacent its left side attached to hinge 246 so that it is openable and closeable about a horizontal axis 248 which extends rearwardly. A closed position of lid 238 is shown in FIG. 16 and its open position is shown in FIG. 23. An access opening or slot 250 is formed through wall 240 and is elongated from adjacent the front end of wall 240 to adjacent its rear end. Slot 250 has front and rear ends 252 and 254 defining therebetween a length which is substantially the same as that of access opening 100 and the three compartments of drawer 14. Slot 250 also has left and right sides 256 and 258 defining therebetween a width which is substantially less than that of access opening 100 and of the compartments of patient drawer 14. In the exemplary embodiment, the width of slot 250 is substantially less than half that of opening 100, typically less than one third the width of opening 100 and typically on the order of about one quarter the width of opening 100. Slot 250 is positioned directly above and along the right side of opening 100 and drawer 14.

A medication guide wall 260 and a medication barrier wall 262 are secured to and extend in a cantilevered fashion downwardly from the bottom of wall 240 respectively to the right and left of slot 250. The upper end of guide wall 260 is secured to the bottom of wall 240 to the right of slot 250 and angles downwardly and to the left to a lower terminal edge or end 264 whereby wall 260 provides a tapered upper surface which angles downwardly and to the left directly below slot 250. Terminal end 264 is positioned to the left of the right side of access opening 100 and the right side of drawer 14 although end 264 is substantially closer to the right sides of opening 100 and drawer 14 than to the respective left sides thereof. Barrier wall 262 is secured at its upper end to the bottom of wall 240 and extends vertically downwardly therefrom to a lower terminal end 266 which is at a approximately the same height as lower end 264. Barrier wall 262 is approximately midway between the right and left of opening 100 and drawer 14. Each of walls 260 and 262 extend continuously the full length of slot 250 and may extend beyond either end 252 and 254 thereof.

Figure 17:
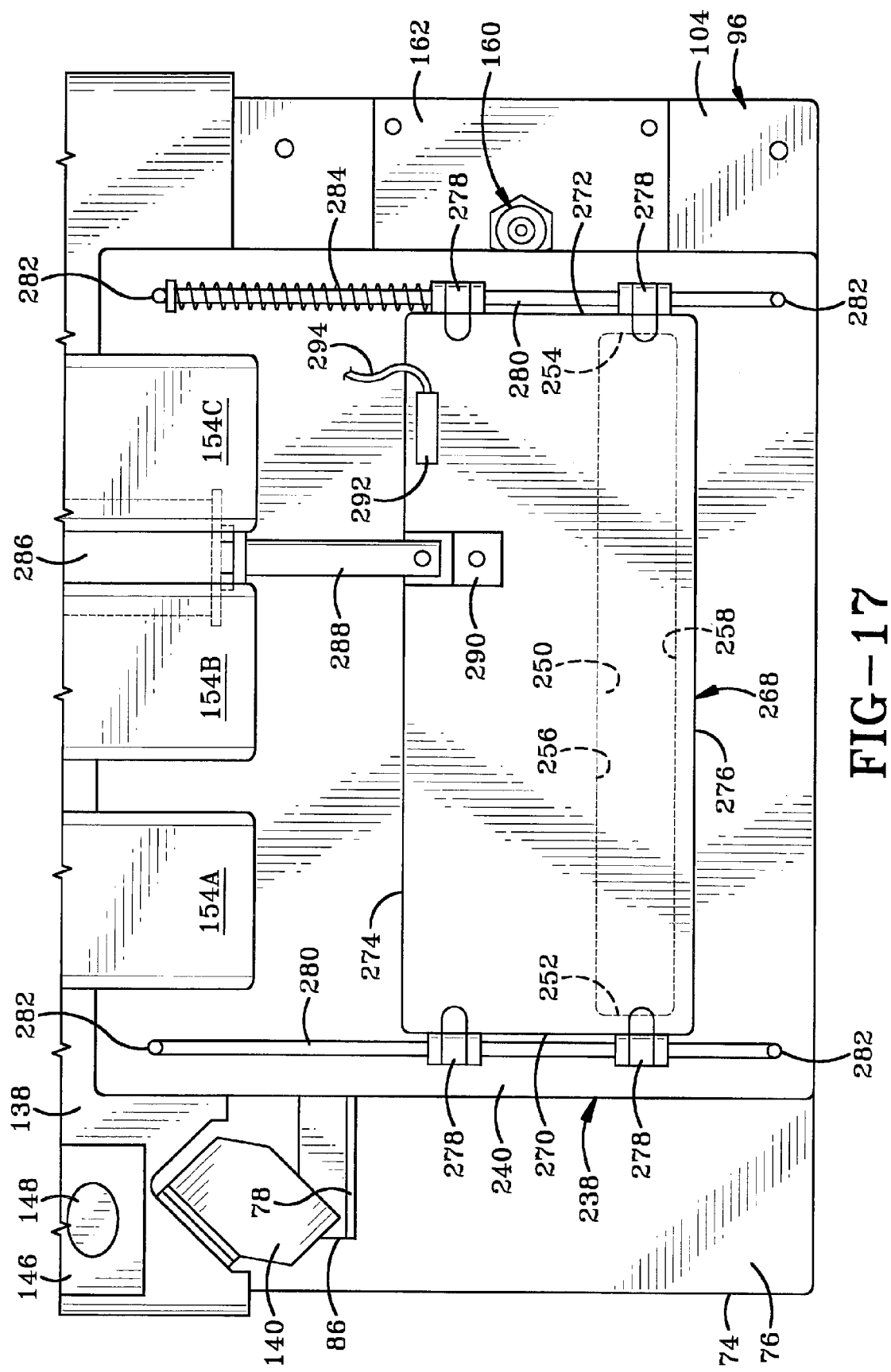
FIG. 17 is an enlarged top plan view primarily illustrating the lid, cover and associated structure.
Figure 19:
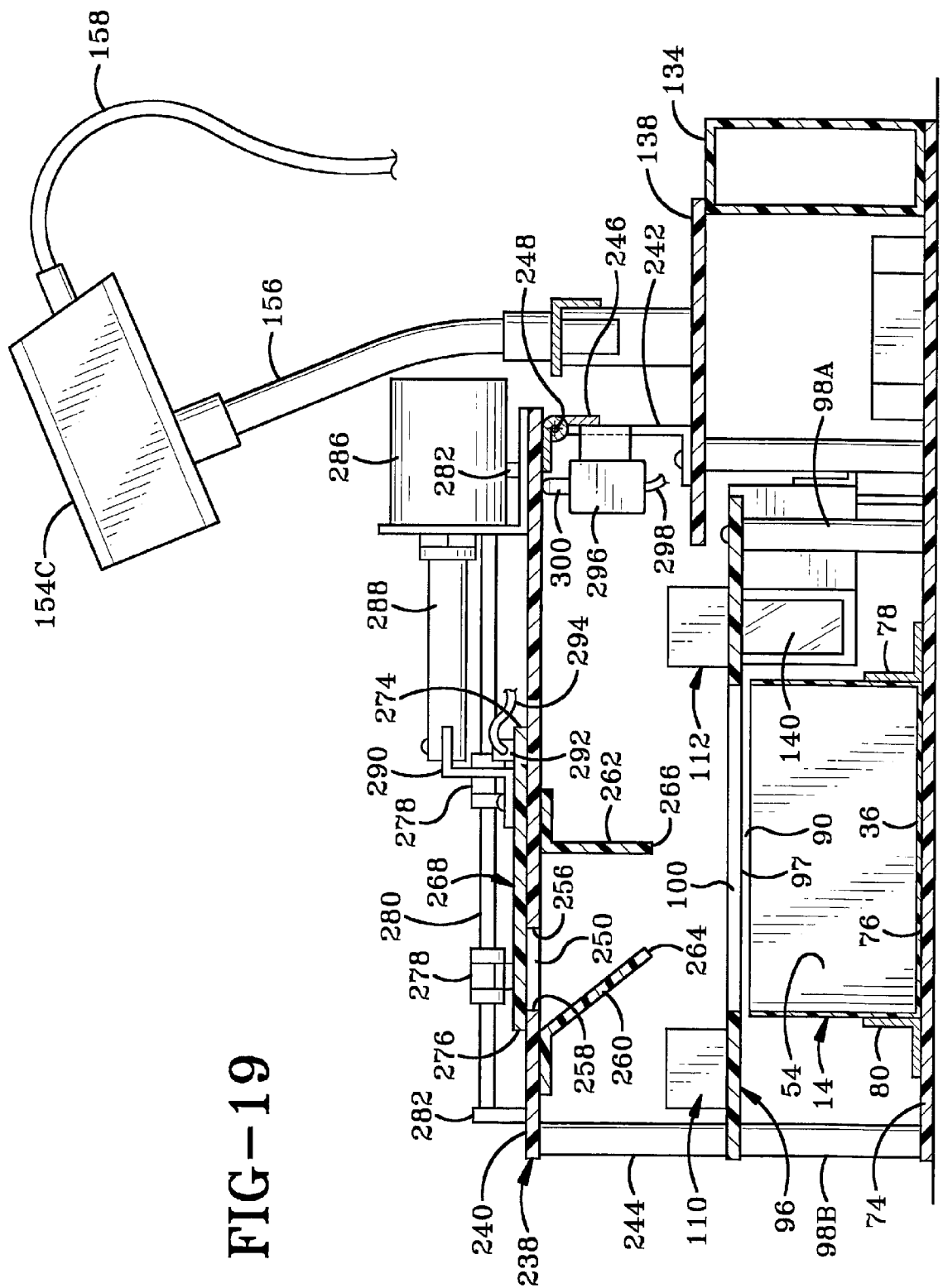
FIG. 19 is a sectional view of the device of FIGS. 16-18 looking forward.
Figure 20:
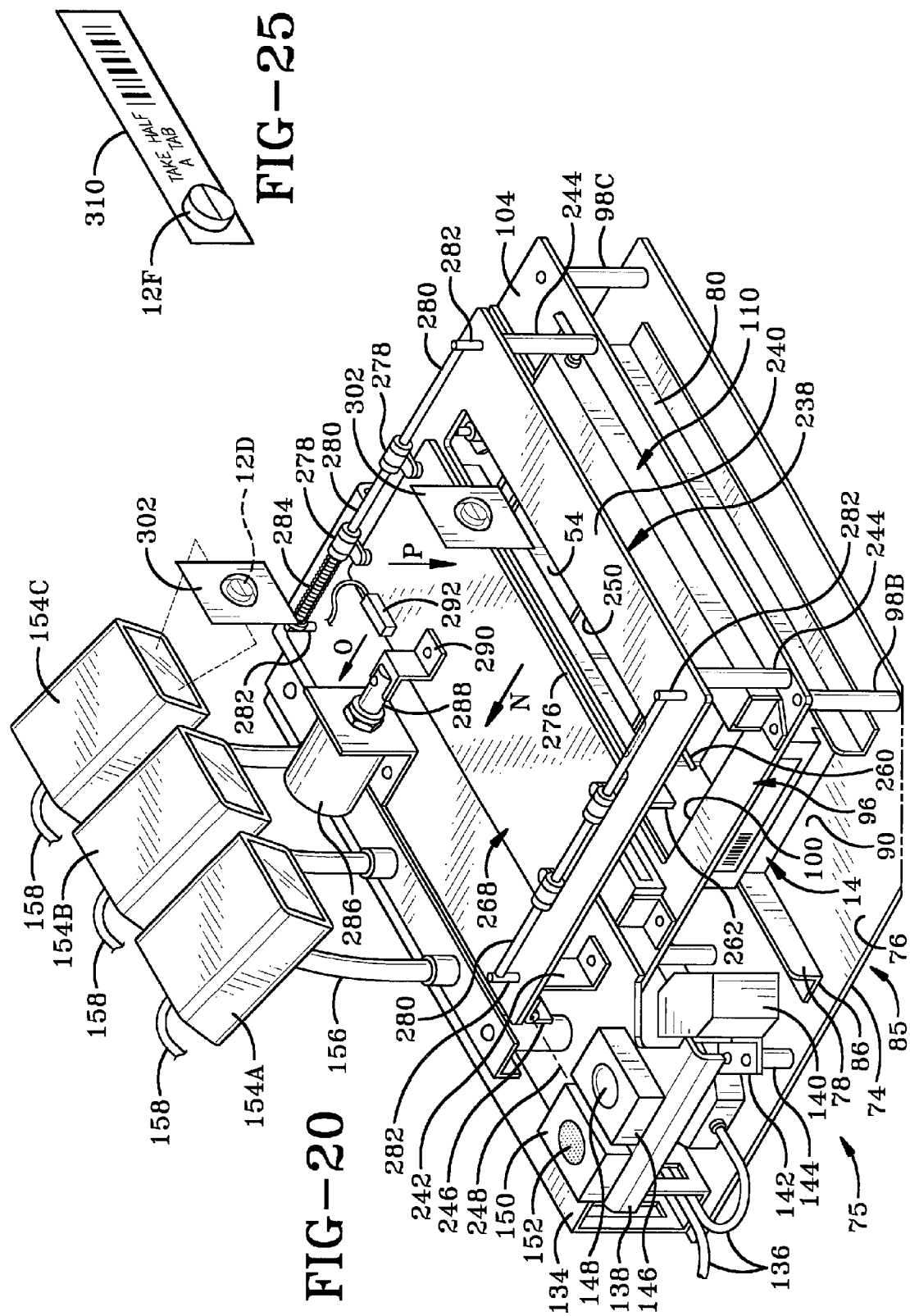
FIG. 20 is a perspective view similar to FIG. 16 showing a medication being identified by one of the medication identifier sensors, the cover being automatically opened and the medication being dropped toward the medication entry slot.

A cover 268 is provided which is slidable back and forth in order to respectively open and close slot 250. Although cover 268 is configured for sliding movement, it may pivot or move in any other suitable manner between open and closed positions. In the exemplary embodiment, cover 260 is transparent, rectangular, flat and horizontal, and is disposed immediately above wall 240. The bottom of cover 268 is either closely adjacent or slidably engages the top of wall 240 during its opening and closing movement. Cover 268 has front and back edges 270 and 272 which define therebetween a length which is preferably at least as long as and typically longer than the length of slot 250. Cover 268 further includes left and right edges defining therebetween a width which is at least as wide as and typically wider than the width of slot 250. The closed position of cover 268 is shown in FIGS. 16, 17 and 19 while its closed position is shown in FIGS. 20 and 21. In its closed or covered position, cover 268 preferably completely covers slot 250 with its right edge 276 adjacent and to the right of right edge 258 of slot 250. Cover 268 may be configured so that it does not completely cover slot 250 in the closed position, but it should nonetheless prevent the passage of medications through slot 250 in the closed position. In the open or uncovered position of cover 268, slot 250 is completely uncovered to provide access for medications to pass therethrough. In the exemplary embodiment, cover 268 in its open position is disposed so that its right edge 276 is to the left of left edge 256 of slot 250 whereby no portion of cover 268 is disposed directly above slot 250. Although slot 250 is completely uncovered when cover 268 is in the open position, this need not be true as long as the opening provided via slot 250 is sufficient for various medications to pass therethrough when the cover is in its open position.

Cover 268 further includes a pair of sleeves 278 adjacent its front end 270 and a pair of sleeves 278 adjacent its rear end 272. Sleeves 278 are tubular members which receive therethrough parallel guide bars 280 of lid 238. Each guide bar 280 is spaced a short distance upwardly of the top surface of horizontal wall 240 and supported at either end by respective support posts 282 which are rigidly secured to and extend upwardly from wall 240. The cylindrical inner surfaces of sleeves 278 slidably engage guide bars in order to guide the sliding movement of cover 268 back and forth in a linear direction. Cover 268 is spring biased to its closed position by a spring member in the form of a coil spring 284 which circumscribes one of guide bars 280 between the left rear post 282 and left rear sleeve 278. As shown in FIG. 16, spring 284 is in a fully extended position with its left end abutting the left rear post 282 and its right end abutting the left rear sleeve 278.

A powered cover drive mechanism or opening mechanism 286 is provided for powering or driving the opening of cover 268. Mechanism 286 is in electrical communication with computer 26 and under the control of the computer program of the verification system. In the exemplary embodiment, drive mechanism 286 is electrically powered and typically includes a solenoid. Mechanism 286 includes a drive arm 288 which is secured to cover 268 by a mounting bracket 290. In the exemplary embodiment, drive mechanism 286 when electrically powered retracts drive arm 288 to move cover 268 from its closed position to its open position, thus overcoming the spring bias of spring 284. Although drive mechanism 286 may be in the form of a motor which drives arm 288 in both directions, it may also drive only in one direction whereby spring 284 serves as the drive mechanism for closing cover 268.

A cover open/closed sensor 292 is mounted on cover 268 in electrical communication with computer 26 via electrical wire 294. Sensor 292 is configured to sense whether cover 268 is open or closed and send a corresponding signal via wire 294 to the computer program run on computer 26. Any suitable sensor may be used. For example, sensor 292 may be a sensor which senses a magnet or uses a magnet in order to move a switch such as a reed switch to open or close an electric circuit when the magnet is near the switch and whereby a signal is sent to the computer program indicating that the lid is either open or closed. Sensor 292 may also be a push-type or plunger-type switch in which a plunger, button or the like, is depressed when the lid is either open or closed and not depressed when the lid is in the opposite position. A lid open/closed sensor 296 (FIGS. 18-19) is mounted on elevated wall 96 via one of first legs 242 and is in electrical communication with computer 26 via electrical wire 298. Sensor 296 is in form of a plunger switch which includes a depressible plunger 300. Sensor 296 is thus configured to sense whether lid 238 is in its open or closed position and to send a signal to computer 26 to that effect. As noted above with regard to sensor 292, lid sensor 296 may be any suitable sensor capable of detecting whether the lid is open or closed.

Figure 18:
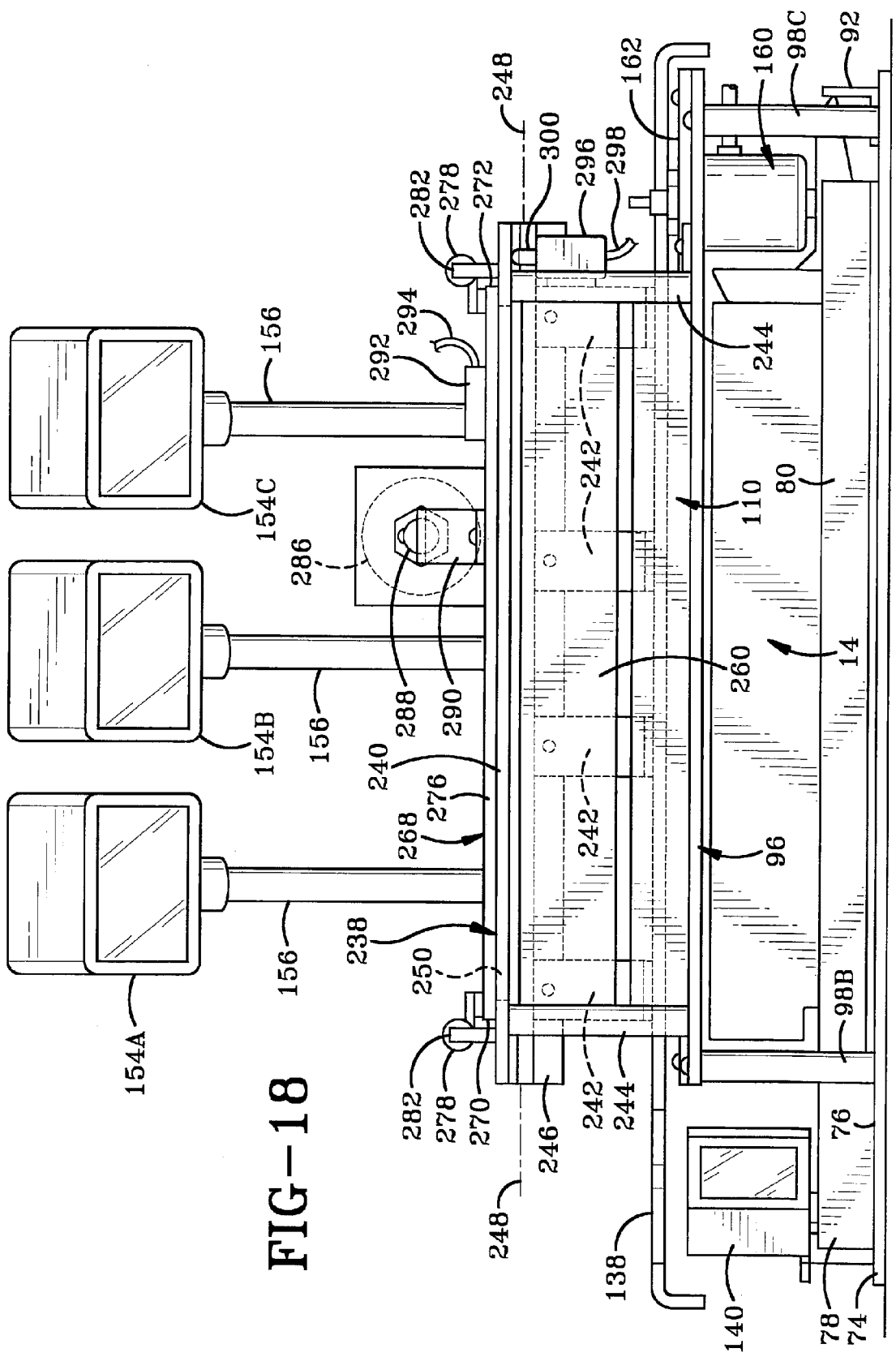
FIG. 18 is a side elevational view of the containment device of FIGS. 16 and 17 taken from the right side.
Figure 18A:
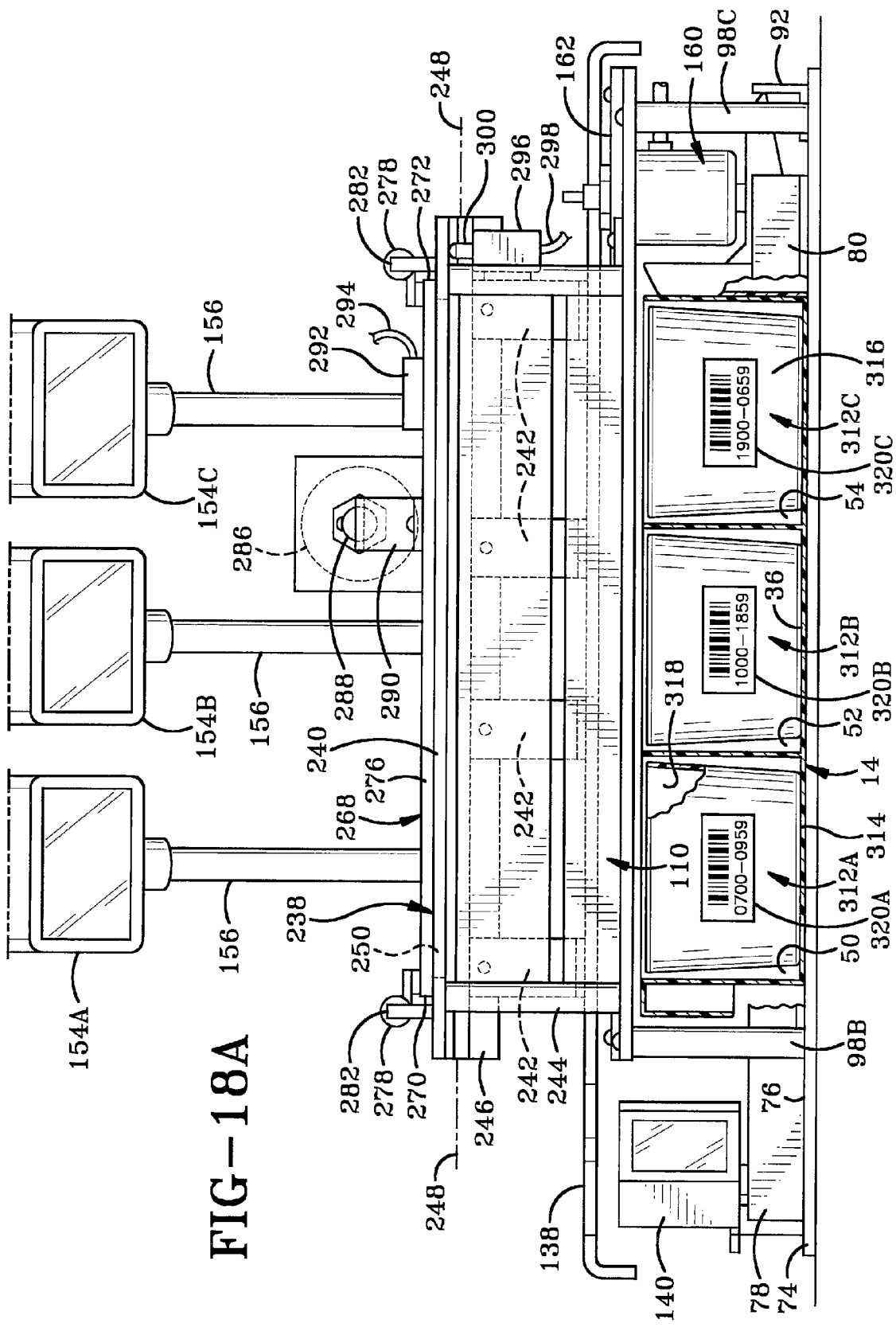
FIG. 18A is similar to FIG. 18 and shows the use of patient-specific time specific containers.

FIG. 18A illustrates a variation in which system 10 includes three patient-specific time-specific containers 312A-C which are removably disposed respectively within compartments 50, 52 and 54 of drawer 14. Each container 312 includes a bottom wall 314 and an annular side wall 316 extending upwardly therefrom whereby walls 314 and 316 define therewithin an interior chamber 318 which opens upwardly at a top entrance opening whereby containers 312 are configured to receive medications. In the exemplary embodiment, side wall 316 includes four substantially flat rectangular walls which are adjacent and respectively parallel to the four side walls or dividers which define the respective compartment in which container 312 is disposed. When the flat walls of containers 312 are thus positioned sufficiently close to the corresponding walls of the compartment of drawer 14 so that medications cannot fall into any space between the outer perimeter of side wall 316 and the inner perimeter of the walls defining the associated compartment of drawer 14. Containers 312 may be formed of substantially rigid material and configured to stand on their own within compartments 50, 52 and 54 or on another support surface such as a table or the like. Thus, for instance, the walls of each container 312 may be formed of metal, plastic or any other suitable material and may be open topped as shown or include lids or closures (as with a standard prescription pill bottle) which may be closed after the filling process to keep medication from falling out and stray medications or other objects from entering the container. Containers 312 may be formed as reusable containers or as the disposable containers. The generally rigid material noted above may be used to form containers within either category. In addition, containers 312 may be formed of paper or the like in order to form cups or bags which will generally tend to be used in a disposable fashion. Time period labels or indicators 320A-C are adhered respectively to containers 312A-C and correspond to the same time periods as previously noted with regard to time period labels 55A-C (FIG. 2) of respective compartments 50, 52 and 54. Each label 320 includes a human readable time period which is the same as that shown on labels 55 respectively. Each label 320 also includes a machine readable code or identifier such as a bar code, an RFID tag or the like which is used for identifying the patient as well as the specific associated time period.

The operation of lid 238, cover 268 and the associated structure is now described with reference to FIGS. 20-24. Although transparent box 164 (FIG. 3) is not shown in FIGS. 20-24, it will be understood that lid 238, cover 268 and all of the associated structure are disposed within transparent box 164 or a similar structure in the exemplary embodiment. FIGS. 20 and 21 show this operation with the use of yet another medication 12D which typically serves as a unit dose within a unit dose package 302. Medication 12D is typically different from medications 12A-C, which are likewise typically different from one another. Unit dose package 302, like package 215 in FIG. 13A, is a typical medication package which often includes a square flat sheet of plastic or other material with a hole formed therethrough, a transparent bubble extending outwardly from the sheet in communication with the hole, and a layer of foil, paper or other similar material laminated on the opposite side of the plastic sheet whereby the user of the medication typically pushes on the transparent bubble to force the pill through the foil, paper or other laminate in order for a patient to access the medication.

In any case, the technician or other person filling the prescription of the various medications which are to be placed into the patient specific drawer 14 typically reads the specified medication on screen 24 of computer 26 (FIG. 9A-9B) in order to determine the next medication listed or specified on the patient's medication profile or medical prescription. Communicating the specified communication to the technician or a robot may be done by an alternate process as previously discussed. The technician or robot then retrieves the medication from the appropriate storage location as previously described. With reference to FIGS. 20 and 21, package 302 is manually or by automation positioned in front of medication identifier 154C, which reads the medication identifier thereon. As previously discussed, sensor 154C is associated with rear compartment 54 of drawer 14 and the associated time period during which the patient is to take medication 12D. As previously described, sensor 154C determines whether medication 12D is the medication which is highlighted or otherwise specified on the computer screen in the same manner as previously discussed. If medication 12D is the correct medication in accordance with the patient profile or prescription, computer 26 controls drive mechanism 286 to automatically open cover 268 (Arrow N) in response to the movement of drive arm 288, whereby slot 250 is open and package 302 is dropped through slot 250 (Arrow P) into rear compartment 54. Sensor 292 moves with cover 268 and senses that cover 268 has moved to the open position. During the opening movement of cover 268, sleeves 278 slidably engage guide bars 280 with left rear sleeve 278 compressing spring 284 against left rear post 282. FIG. 21 further illustrates the movement of package 302 by the downwardly pointing Arrows such that package 302 moves to the right and downwardly away from sensor 154C and toward slot 250, through which it is dropped onto the angled surface of guide wall 260 so that package 302 moves to the left and downwardly and into rear compartment 54. Barrier wall 262 helps prevent medications and unit dose packages from inadvertently being knocked out onto elevated wall 96 and thus not entering drawer 14. As FIG. 21 shows, package 302 moves downwardly below the lower terminal ends 264 and 266 of walls 260 and 262 to pass through the plane of detection of light beams 122 prior to entering compartment 54. The entry sensor in the form of light curtain 110 thus detects the entry of package 302 into drawer 14 as previously discussed. The computer program is typically configured to activate drive mechanism 286 for just a few seconds in order to allow the technician or robot to drop the medication through slot 250 into the drawer therebelow. The computer program either activates drive mechanism 286 to drive cover 268 back to its closed position or deactivates mechanism 286, for instance when it is a solenoid, whereby spring 284 drives cover 268 to its closed position. In the exemplary embodiment, slot 250 typically remains open from about three to five seconds. Although this time period may vary, its duration is usually within the range of two to six seconds and typically no more than six to ten seconds. This relatively short time period thus allows the technician or robot to drop the medication into the proper compartment and also minimizes the possibility that other medications or stray objects may enter the patient drawer through slot 250. Cover 268 thus normally remains closed except during these relatively short time periods of being open in response to sensors 154 identifying the correct medication.

Figure 22:
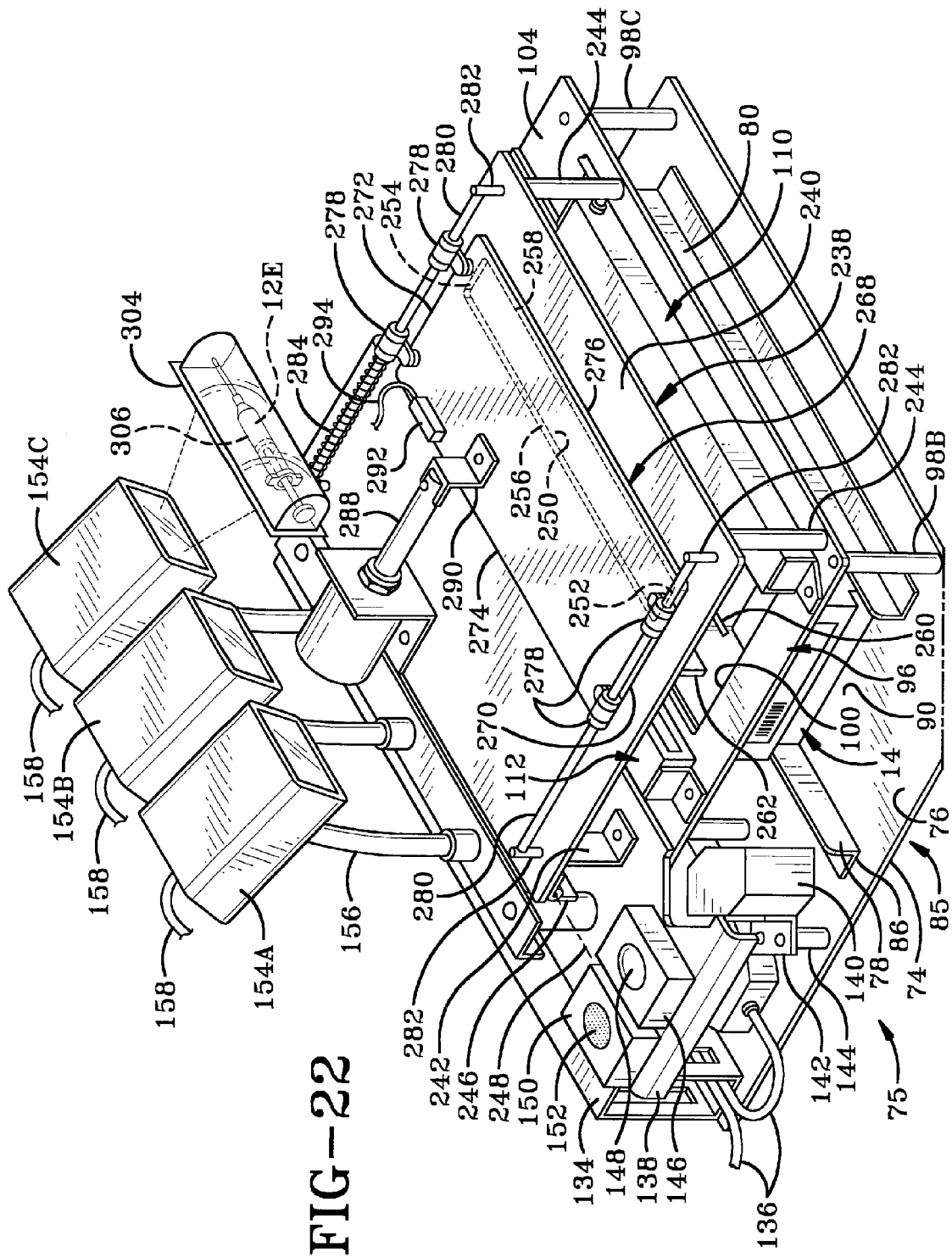
FIG. 22 is a perspective view similar to FIG. 20 and shows a different medication in liquid form which is contained within a syringe in a package which is too large or generally difficult to fit through the slot and in which the medication package is being scanned by one of the medication identifier sensors.
Figure 24:
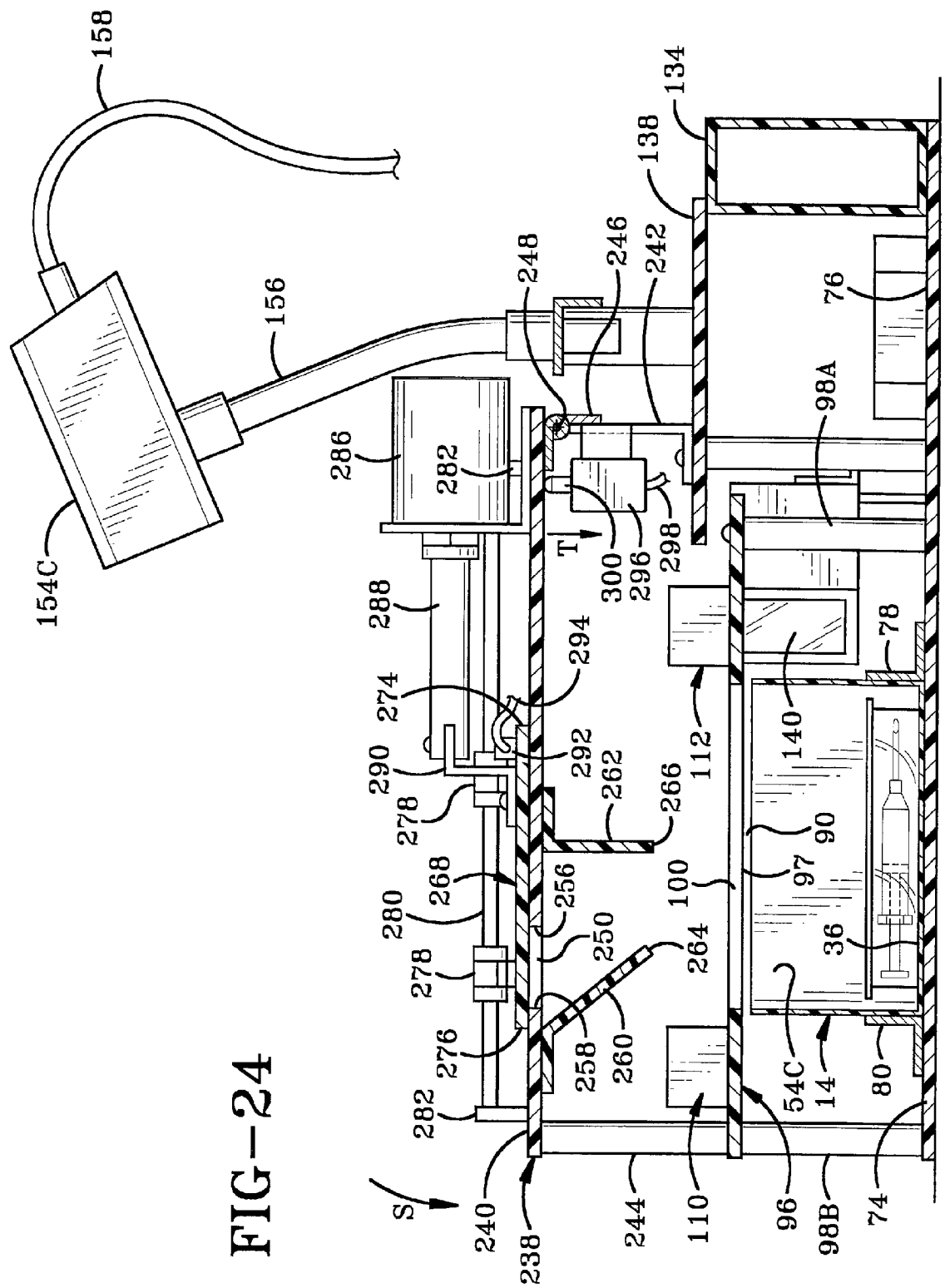
FIG. 24 is similar to FIG. 23 and shows the lid being closed again.

Referring now to FIGS. 22-24, the operation of lid 238 is described in greater detail. Lid 238 is configured primarily to allow for the placement of various medications and their associated packages into drawer 14 without passing through slot 250. More particularly, some packages are difficult to move through slot 250 or are simply too large to move therethrough. The computer program run by computer 26 is thus configured to allow for the opening of lid 238 without creating an error signal or error report to the pharmacist in certain circumstances. FIGS. 22-24 illustrate the use of the verification system with yet another unit dose package 304 which contains a different medication 12E which is in liquid form and in particular is contained within a syringe 306 in a pre-measured amount which makes up the unit dose of the medication. The figures show syringe 306 including a hypodermic needle although a syringe without such a needle may be used for instance to simplify the taking of liquid oral medications. As with the previous medications, the computer program 26 highlights or otherwise specifies the name of the medication 12E on screen 24 of computer 26 to direct the technician to pull the appropriate medication. Package 304 is positioned adjacent sensor 154C as previously discussed so that said sensor checks to see if it is the correct medication. If it is the correct medication, the computer program gives the appropriate good scan tone or other correct medication indicator and may indicate on the computer screen or via an audible or visible signal that lid 238 may be manually opened.

As shown in FIG. 22, the right side of lid 238 is supported atop the upper ends of posts 244. To open lid 238, the technician simply manually lifts lid 238 along its right edge so that wall 240 is lifted upwardly and off of legs 244 as it pivots about axis 248 of hinge 246, (Arrow Q in FIG. 23). As lid 238 is lifted upwardly, plunger 300 is allowed to move upwardly (Arrow R) under the spring bias of an internal spring within sensor 296. The movement of plunger 300 upwardly thus creates a signal which is communicated to computer 26 that lid 238 is open. The lifting of lid 238 is in accordance with the computer program in light of the specific medication and thus does not produce an error report in response to the signal sent from sensor 296. An error report would be produced in response to such a signal if lid 238 were opened at any time during the filling process without first having been authorized by the computer program in response to one of sensors 154 identifying a medication which accorded with a program specified medication of the sort which was intended to be placed in the patient drawer by way of the open lid. Once lid 238 is open, the technician then moves package 306 with medication 12E therein through the entrance or access opening 308 which is created below the raised right side of lid 238 and into compartment 54 of drawer 14. Entrance opening 308 thus provides access to patient drawer 14 which is distinct from and larger than the access provided by access opening or slot 250. As with the previously discussed medications, package 306 passes through the plane of detection of beams 122 whereby the entry sensor senses the entry of package 306 into drawer 14.

Once package 306 is in the proper compartment of drawer 14, lid 238 is then lowered (Arrow S in FIG. 24) so that it is closed. The closing of lid 238 depresses plunger 300 of sensor 296, thereby signaling the computer program to that effect. The computer program may allow a certain limited time for lid 238 to be opened without producing an error report. Again, this is typically several seconds as discussed above in regard to the opening of cover 268. The opening and closing of lid 238 may be automated, but is not necessary. It is further noted that the system may be configured so that cover 268 is simply manually opened and closed instead of being driven in either direction by a drive mechanism such as mechanism 286 or 284. However it is preferred that cover 268 be biased to its closed position. It is further preferred that the system is set up so that the computer program can limit the amount of time that slot 250 is open.

Referring now to FIG. 25, an alternate configuration is shown for marking a medication with a caution label which indicates a partial dose. For example, FIG. 25 shows a caution label 310 which is attached directly to a medication 12F in the form of a pill wherein the caution label 310 includes a bar code or other machine readable medication identifier as well as a human readable textual message which in the present example indicates "take half a tab". It has been found that applying some partial dose caution labels to certain unit dose packages such as certain bags made it difficult to effectively scan the labels. Thus, the method of the present invention includes directly adhering caution label 310 to a pill or the like with a layer of adhesive along one side of label 310. Label 310 is removably attached to the pill and may be simply manually peeled off prior to administration.

Figure 26:
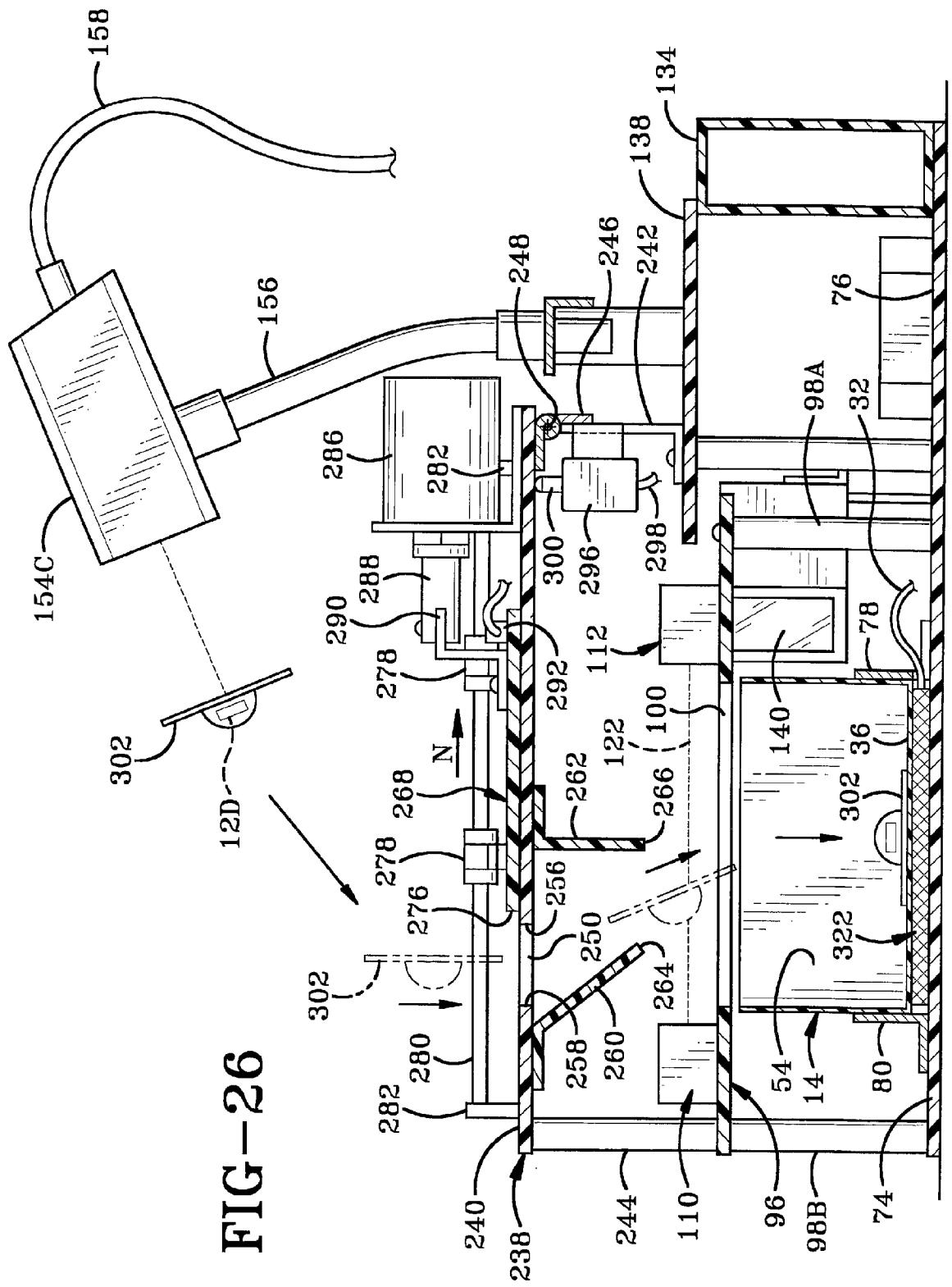
FIG. 26 is a sectional view similar to FIG. 24 showing an alternate entry sensor which uses a scale for weighing medications as they enter the drawer.

FIG. 26 illustrates an alternate entry sensor which comprises a scale 322 which is in electrical communication with computer 26 via one of wires 32. Scale 322 is configured for weighing drawer 14 and the various medications and/or medication packages as they enter drawer 14. Although FIG. 26 shows entry sensor 110 as well, scale 322 may be used without entry sensor 110 in order to provide the sole entry sensor as controlled by the computer program. In order for scale 322 to function effectively as an entry sensor, it needs to be sufficiently sensitive to discern relatively small weight changes when used with unit dose packages as is typically the case with system 10. In operation, the medication package 302 or the medication will be scanned by the medication identifier sensor 154 as previously discussed. The pre-established weight of a given medication or medication package is stored in a database which the computer program accesses in order to determine whether the medication or medication package which enters drawer 14 is in accordance with the pre-established weight of said medicine or medicine package. If the weight as determined by scale 322 is within sufficient tolerance of the established weight, a correct scan indicator will be activated whereas an incorrect indicator may be activated if the determined weight is not within the pre-established tolerance of the pre-established weight within the database. Scale 322 can also be used in conjunction with, for example, another entry sensor such as entry sensor 110 to provide additional verification.

Figure 27:
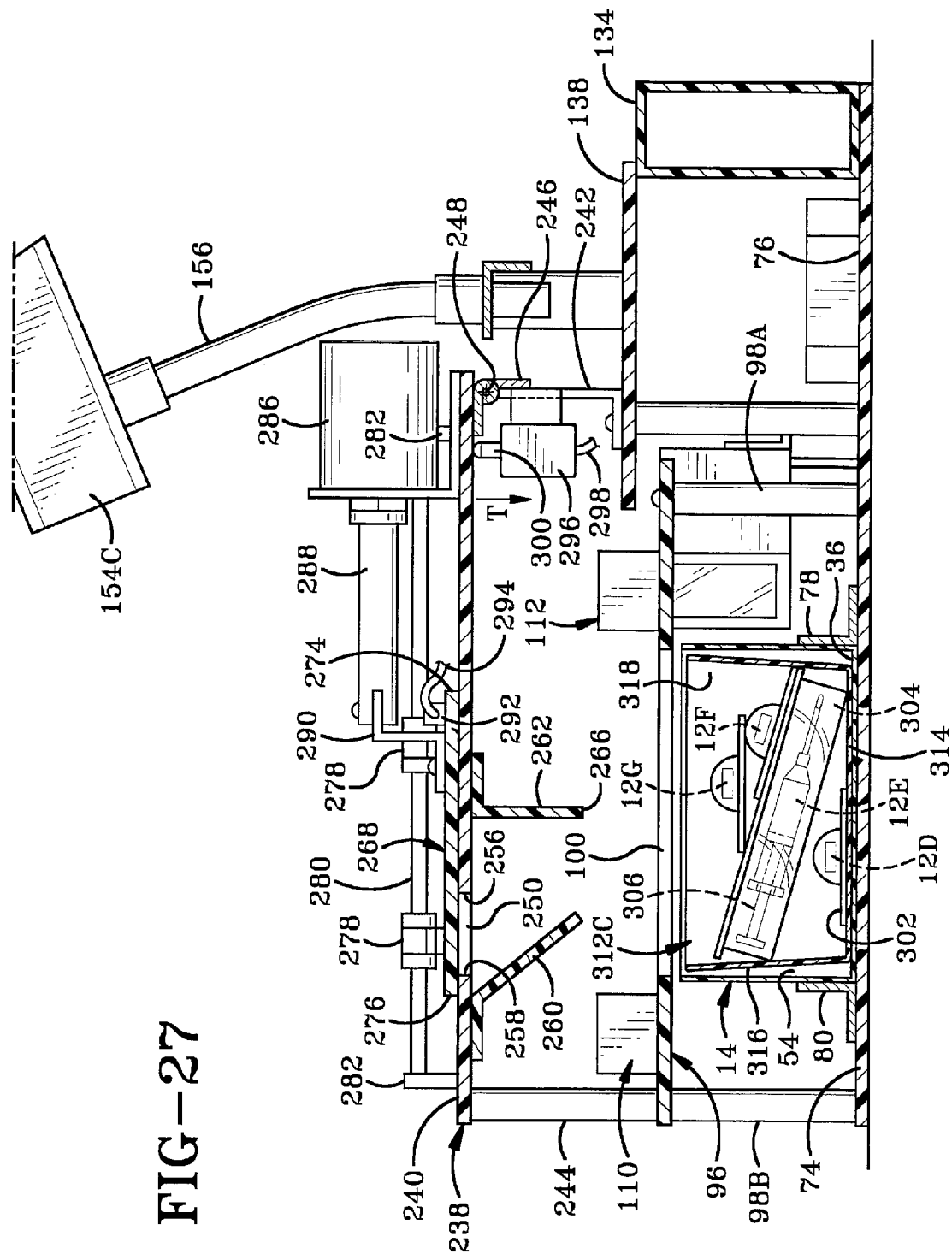
FIG. 27 is similar to FIG. 18 and shows three patient-specific containers removably disposed in the compartments of the patient drawer.
Figure 28:
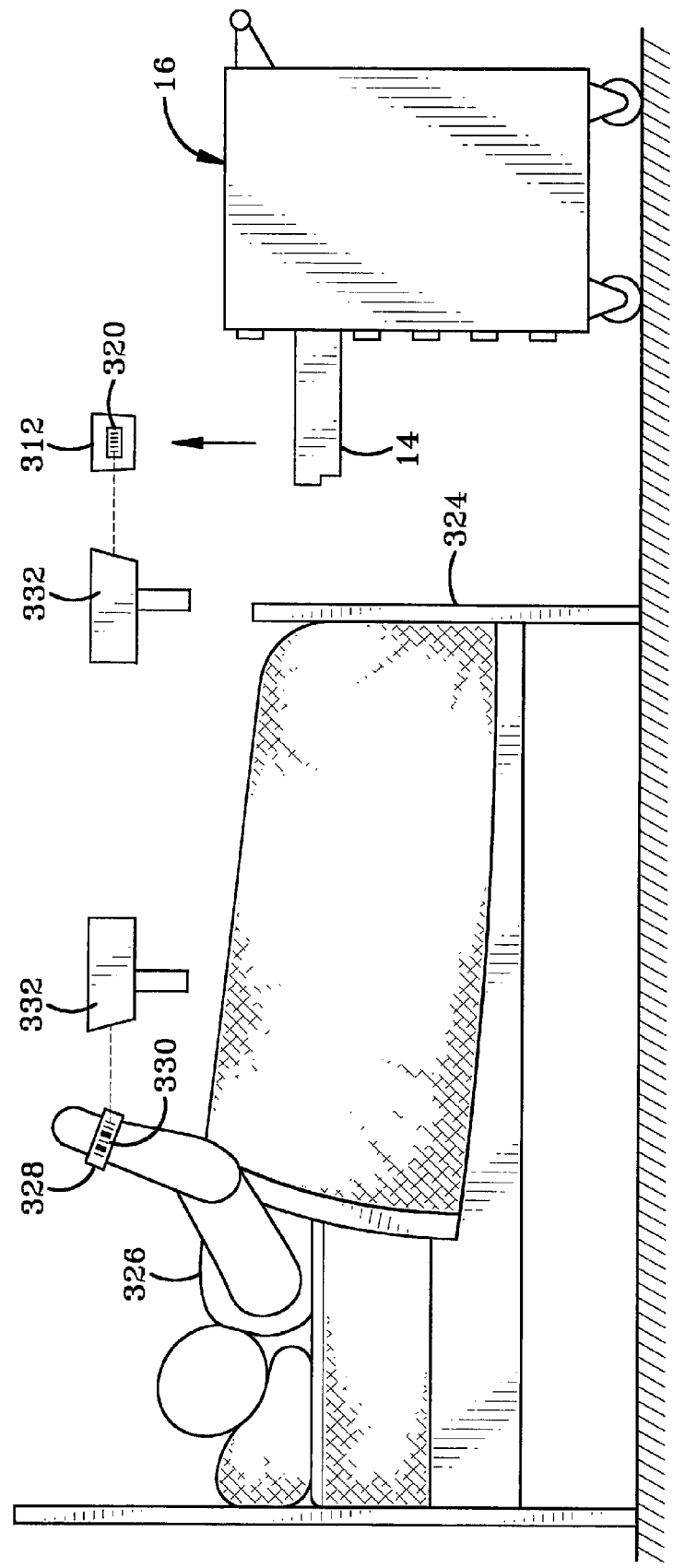
FIG. 28 is a diagrammic view of the hospital rolling cart with one patient drawer open and one of the patient specific containers removed therefrom, the on-board or portable scanner scanning the label on the removed container, and the scanner scanning the patient identification bracelet of the patient at a bedside location.

FIGS. 27 and 28 illustrate the operation of system 10 when using containers 312A-C (FIG. 18A). FIG. 27 illustrates one of containers 312 having been filled in various medications in a serial or sequential manner wherein said medications are indicated at 12D-G. The filling process using containers 312 is the same as previously described except that the medications enter containers 312 within compartments 50, 52 and 54 instead of simply entering said compartments. Where sub arrays 124, 126 and 128 (FIG. 3A) are used, they are respectively associated with sensing entry of medications or other objects into containers 312A-C. FIG. 28 illustrates the bedside dispensing and administration of medications in one of containers 312. More particularly, cart 16 is rolled from the pharmacy or other location into or adjacent the patient's room. FIG. 28 illustrates that the hospital room or the like contains a bed 324 for the patient 326, who is wearing a patient identification bracelet 328 which includes a machine readable patient identifier 330 such as a barcode or the like. System 10 may further include a portable scanner 332 which a nurse or other hospital professional may carry or which may be onboard cart 16. As shown in FIG. 28, the drawer 14 which is associated with patient 326 is opened and container 312 is removed therefrom so that scanner 322 can scan the time period label 320 thereon, which is associated with the patient as well as the specific time period during which the medications within container 312 are to be administered. Scanner 322 may also be used to scan patient identifier 330 so that the computer program can make a comparison to verify that patient 326 is indeed the patient who is to take the medications within container 312. If so, the nurse will administer the medications from container 312 to patient 326. If not, then said medications will not be administered and additional verification will be undertaken. This patient verification procedure is helpful in light of the fact that patients are often moved from one hospital room to another. In addition, the use of container 312 simplifies the administration of the medications associated with the associated time period because scanner 332 merely needs to read label 320 instead of independently reading each of the labels associated with each medication within container 312. Due to the fact that system 10 has already verified all of the medications within container 312 and associated them with label 320, the use of the time specific container 312 eliminates this additional scanning of individual medications at the point of or just prior to administering the medication to the patient.

As previously discussed, containers 312 may be formed of substantially rigid material or flexible materials and may be reused or disposed of after the medications have been dispensed therefrom for administration to the patient. The use of containers 312 in the form of paper cups is a convenient way of administering the medications such that the nurse can simply hand the paper cup to the patient so that the patient takes the medication therein so that the paper cup may be simply disposed of thereafter. When the containers 312 are formed as paper or plastic bags or the like, they may be sealed or generally closed in one manner or another such that the nurse or patient may simply open the bag or tear it open in order to access the medications therein just prior to administering the medication to the patient. Like the paper cups, these bags are easily disposable.

Figure 29:
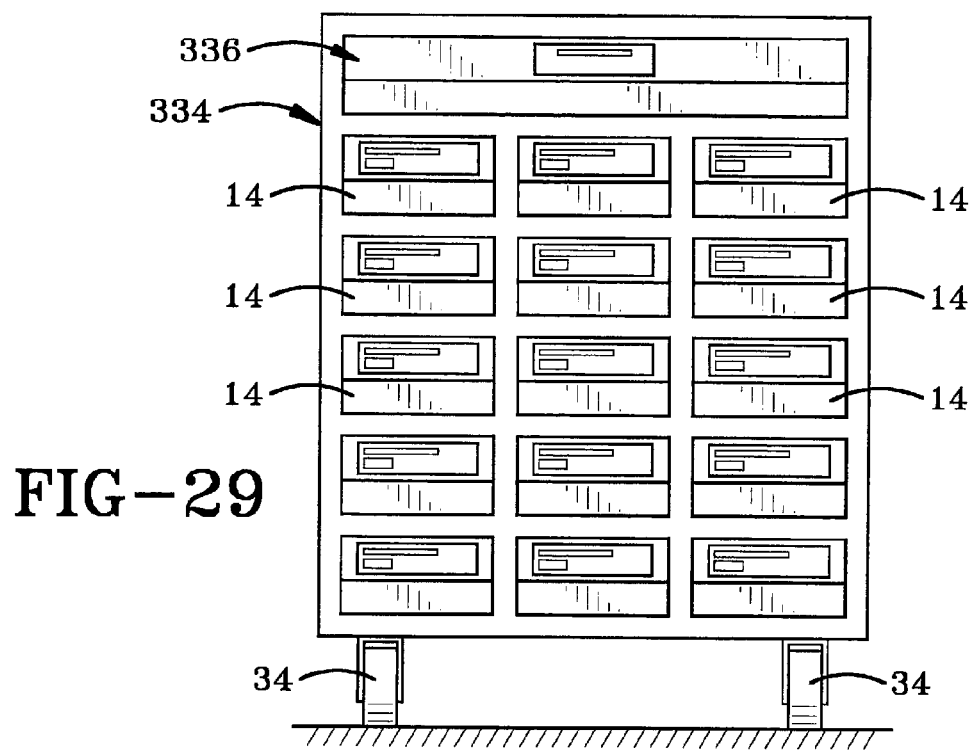
FIG. 29 is a front elevational view of a rolling cart which includes patient drawers and a bulk medicine drawer.
Figure 30:
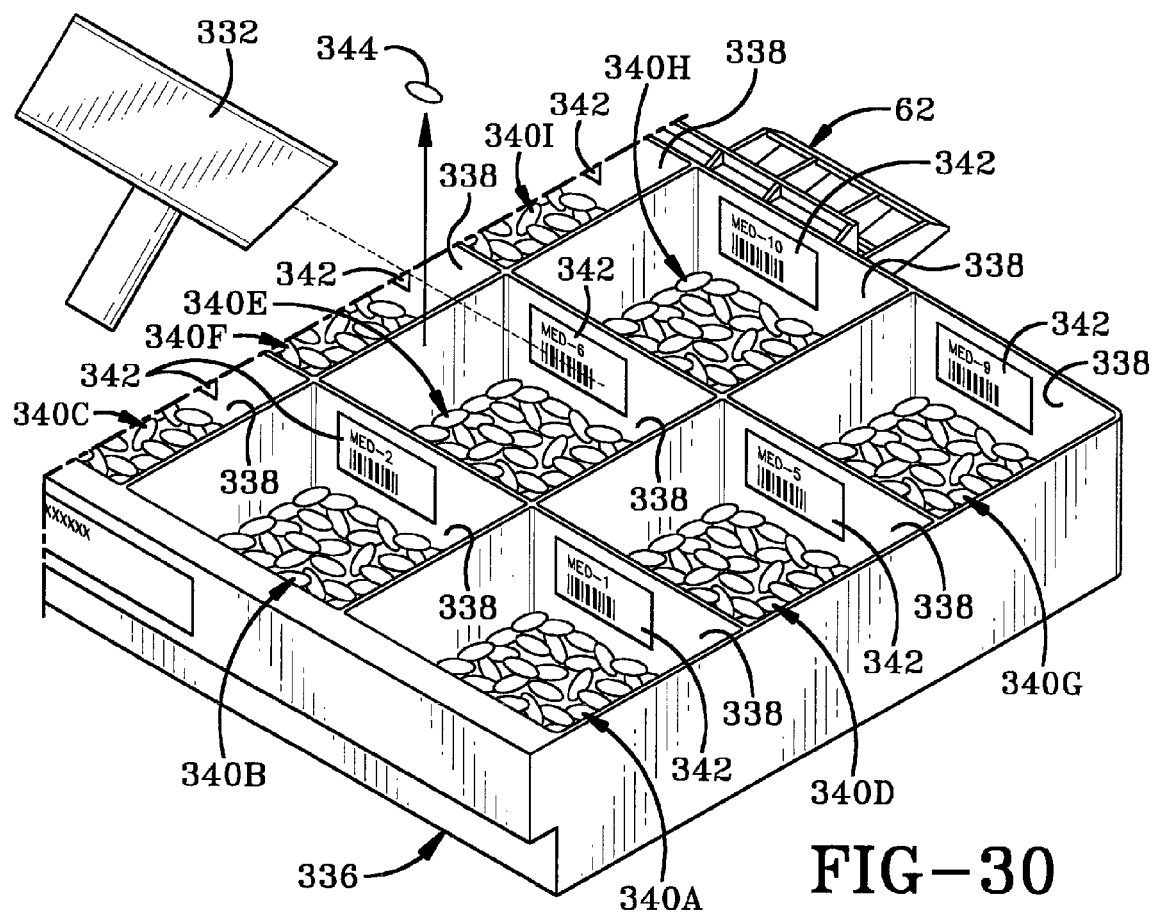
FIG. 30 is a perspective view showing a portion of the bulk medicine drawer with several of the bulk medicine compartments thereof with a scanner scanning one of the compartment labels and an associated medication being removed from the associated compartment.

FIGS. 29 and 30 illustrate an additional improvement in the administration of medications which is particularly useful within a hospital setting. FIG. 29 illustrates a wheeled or rolling cart 334 which is similar to cart 16 in that it includes wheels 34 and contains multiple patient drawers 14 such that cart 334 may be used in the same manner as cart 16 with respect to system 10 as previously described. In addition, cart 334 includes a bulk medication drawer 336 which is generally substantially larger than patient drawer 14 and includes multiple bulk medication bins or compartments 338. Drawer 336 may include lock engageable structure 62 or the like so that drawer may be selectively locked into cart 334. Each compartment 338 contains a specific medication in bulk (i.e., multiple unit doses such as pills, capsules, etc.) wherein each compartment 338 contains in bulk a different or distinct medication, as indicated at numbers 340A-I. These medications may be controlled or non-controlled, but are generally not scheduled controlled medications, which are high-risk medications. Each compartment 338 has its own medication label or identifier 342 which includes a human readable portion and a machine readable portion which corresponds to the specific medication 340A-I within respective compartment 338, as illustrated by the different medication references on each label, for example, "MED-1", "MED-2", etc.

In operation, cart 334 allows a nurse or other authorized individual to quickly access medications which may be dispensed on an as needed basis to the patient. The nurse can thus quickly access such over-the-counter medications from the nearby cart instead of having to return to a centralized location where these medications are conventionally stored in order to retrieve the same and bring them back to the patient. More particularly, the nurse can use a scanner 332 to scan (FIG. 30) a label 342 associated with the medications in the corresponding compartment 338 to indicate a pill 344 or the like of a specific one of the medications has been removed from the associated compartment 338 to be administered to the patient. The nurse will also have used scanner 332 to scan patient identifier 330 on the patient's bracelet 328 (FIG. 28) whereby the computer program makes the association between the given patient and the medication pulled from the medication compartment 338 having the label 342 which was scanned in order to track which medication the patient has taken as well as to automatically charge the patient's account for the medication.

Figure 31B:
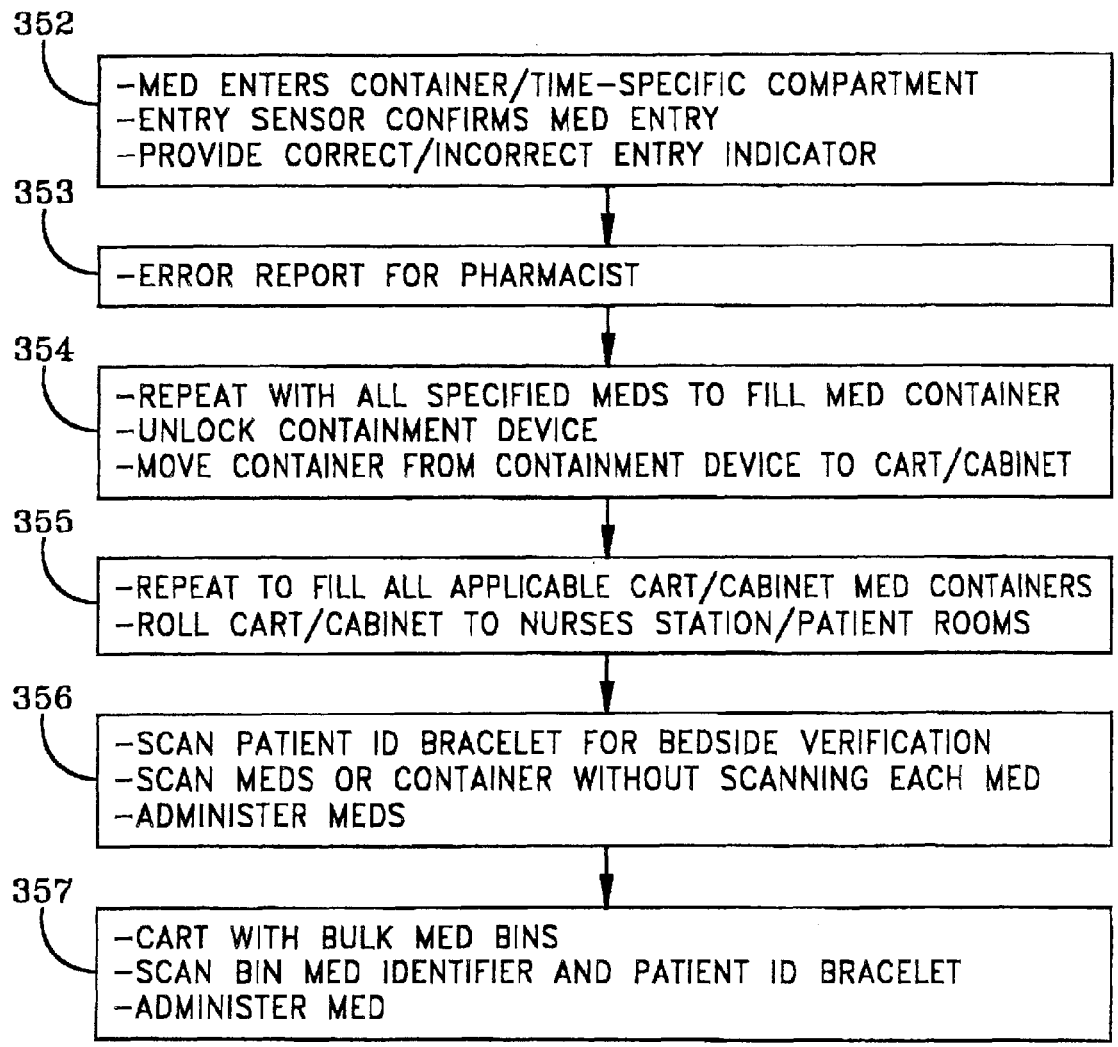
FIG. 31 shows the relationship between FIGS. 31A and 31B, which together provide a flow chart broadly illustrating the medication verification process.

FIG. 31 (FIG. 31A-31B) is a flow chart illustrating the overall process relating to the use of system 10. As noted at block 345, a patient is admitted to the hospital and the patient's pertinent information including his or her identification is entered into a computer database which is typically that of the hospital. Once examined by a doctor, the doctor may prescribe medications as indicated at block 346, after which the pharmacist or doctor inputs the prescription into a computer database which may be the hospital database or the database of verification system 10. If the prescription is input into the hospital database, system 10 can access said database via an appropriate interface. One or more doctors will prescribe medications for a variety of patients for which the pharmacist or doctor also inputs the various prescriptions. Especially in the setting of a hospital or similar healthcare facility, the prescriptions typically specify specific time periods during which the medications are to be taken, such as a specific 24-hour period which may include a portion of one or two calendar days, or a time period which is less than 24 hours. As shown in block 347, a technician will log onto the computer of system 10 to access the medication verification program. The technician or robot will then unlock and remove the patient drawer or other container from the rolling cart or cabinet and insert it into the containment device as noted at block 348. The drawer is automatically locked to the containment device in a secured fill position in which the drawer is ready to be filled with medications prescribed for the patient associated with the drawer or in accordance with a stocking order. Block 349 further indicates that the appropriate sensor reads the drawer label or pertinent identifier to establish the patient associated with the drawer and the pertinent patient-related information including medications. The computer program prompts the technician to perform an empty drawer check to make sure the drawer is empty and also to check the drop area to search for and remove any foreign objects which might get knocked into the drawer if not removed. The program then generates a medication profile for the given patient or stocking order and provides a storage location and dispensing time period for each medication. As indicated at block 350, the technician or robot then picks the indicated medication from its storage location in accordance with the profile or order. As noted at block 351, the computer program will verify the medication as the technician scans the medication with the appropriate medication ID sensor. In accordance with whether the medication is determined to be the correct or incorrect medication, the program is configured to provide a correct or incorrect indicator which communicates to the technician or robot whether the medication should be entered into the drawer or other container or compartment which may be time-specific and patient specific or medication specific. As noted at block 352, the technician or robot will then enter the medication into the drawer or other compartment or container, preferably only if it is the correct medication. The entry sensor confirms the entry of the medication and a correct or incorrect entry indicator is provided depending on whether the correct or incorrect medication entered the drawer. If there are pertinent errors, an error report will be generated by the program for review by the pharmacist, as indicated at block 353. As noted at block 354, the drawer fill is completed by repeating the previous steps in accordance with the computer program for all of the prescribed medications indicated in the patient profile. The containment device is then automatically unlocked so that the technician or robot can remove the containment device and reinsert it into the rolling cart. As noted in block 355, the entire procedure is repeated in order to fill all applicable containers in a cabinet or drawers in a cart or a first set of carts which are typically used for delivering and dispensing medications the following day since a second set of carts is being used during the day that the first set of carts is being filled. Although the process has been largely described with reference to hospital carts which are transported from the pharmacy to a nurses station or patient room, it is also noted that an individual medication container such as previously discussed containers 312 (FIG. 18a) may be transported individually by hand separate from a cart, which often occurs when a patient enters the hospital and needs an initial dose of medication prescribed after arrival. When the carts are rolled to or nearby a given patient room, a bedside verification process is carried out as indicated at block 356 by scanning the patient identification bracelet and checking for a match between the identified patient and a set of medications in the drawer/container to verify that the pertinent medications have been prescribed for the given patient. More particularly, the medication packages may be scanned individually or the container holding the medications can be scanned without the necessity of scanning each medication individually in order to ascertain whether the patient and the medications are a match. If so, the medications are administered to the patient, according to the time period on the time specific container. Block 357 illustrates the process of using system 10 for the dispensing of medications. More particularly, a cart with bulk medication bins may be used by scanning the bin medication identifier and the patient ID bracelet and administering the medication so that the medication can be easily tracked for various purposes and so that medications can be dispensed from the de-centralized rolling cart. The process discussed with reference to FIG. 31 is described in greater detail at various places throughout the present application.

Thus, the medication verification system of the present invention substantially decreases the amount of time that a pharmacist spends checking for the accuracy of the medications within patient drawers while also providing a high degree of accuracy for the filling procedure. This system is conveniently configured for use with standard patient drawers and thus does not require additional containers although as discussed above the system may also be used with containers other than patient drawers. The sensor assembly provides a mechanism for correctly identifying medications as well as a mechanism for determining whether the correct medication entered the drawer or other container. This system is also configured to eliminate or minimize inadvertent entry of stray objects or incorrect medications and provides reports indicating errors so that, amongst other things, the pharmacist may check any drawers that need verification. The computer program of the system is configured to interface with the host system computer program or computer programs of the hospital in order to provide communication between the system of the present invention and the host system with regard to tracking and updating all orders and patients concerned. In addition, the interface between the present system and the host system includes a billing interface to facilitate the automated billing process noted above.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A method comprising the steps of:
    determining with a medication identification sensor whether a first medication is a correct or incorrect medication;
    producing a correct or incorrect medication indicator respectively depending on whether the first medication is the correct or incorrect medication in accordance with the step of determining;
    causing entry of the first medication into a medication container after the step of producing;
    sensing the entry with an entry sensor to verify that the first medication has entered the container;
    further comprising, after the steps of determining, producing, causing and sensing, the steps of
    determining with a medication identification sensor whether a second medication is a correct or incorrect medication;
    producing a correct or incorrect medication indicator related to the second medication respectively depending on whether the second medication is the correct or incorrect medication in accordance with the step of determining whether the second medication is a correct or incorrect medication;
    causing entry of the second medication into the container after the step of producing the indicator related to the second medication; and
    sensing the entry of the second medication with an entry sensor to verify that the second medication has entered the container; and further comprising the steps of
    providing a containment device which defines a filling position, wherein the containment device includes a wall which has inner and outer surfaces and defines an access opening extending from the inner surface to the outer surface above the filling position, wherein the wall carries a cover which is movable relative to the wall between an open position in which medications may pass through the access opening into the container and a closed position in which medications may not pass through the access opening into the container;
    positioning the container at the filling position under the wall and access opening by moving the medication container relative to the wall to insert the medication container into the filling position so that the access opening is above the medication container in the filling position;
    opening the access opening by moving the cover from the closed position to the open position while the container remains at the filling position;
    dropping the first medication through the opened access opening into the container to effect the step of causing entry of the first medication;
    closing the access opening, after the step of dropping and before the step of determining whether the second medication is a correct or incorrect medication, by moving the cover from the open position to the closed position;
    reopening the closed access opening after the step of producing the indicator related to the second medication by moving the cover from the closed position to the open position while the container remains at the filling position;
    dropping the second medication through the reopened access opening into the container while the container remains at the filling position to effect the step of causing entry of the second medication into the container;
    removing the container with the first and second medications therein from the filling position by moving the container relative to the wall;
    wherein the step of determining whether the first medication is a correct or incorrect medication comprises determining whether the first medication is a correct or incorrect medication by reading a first machine readable identifier connected to the first medication with a medication identification sensor mounted adjacent the wall and the access opening;
    the step of dropping the first medication comprises dropping the first medication with the first identifier connected thereto through the opened access opening into the container;
    the step of determining whether the second medication is a correct or incorrect medication comprises determining whether the second medication is a correct or incorrect medication by reading a second machine readable identifier connected to the second medication with a medication identification sensor mounted adjacent the wall and the access opening; and
    the step of dropping the second medication comprises dropping the second medication with the second identifier connected thereto through the reopened access opening into the container.

2. The method of claim 1 wherein the step of dropping the first medication comprises releasing the first medication from one of a person's hands while the first medication is above the opened access opening; and
    the step of dropping the second medication comprises releasing the second medication from one of the hands while the second medication is above the reopened access opening.

3. The method of claim 1 wherein the medication identification sensor used to determine whether the first medication is a correct or incorrect medication faces toward a space above the access opening;
    the step of reading the first machine readable identifier occurs while the first medication is in the space above the access opening;
    the step of dropping the first medication comprises releasing the first medication while the first medication is in the space above the opened access opening;

the medication identification sensor used to determine whether the second medication is a correct or incorrect medication faces toward the space above the access opening;

the step of reading the second machine readable identifier occurs while the second medication is in the space above the access opening; and the step of dropping the second medication comprises releasing the second medication while the second medication is in the space above the reopened access opening.

4. The method of claim 3 wherein the step of reading the first machine readable identifier occurs while holding with one of a person's hands the first medication in the space above the access opening;

the step of releasing the first medication comprises releasing the first medication from one of the hands;

the step of reading the second machine readable identifier occurs while holding with one of the hands the second medication in the space above the access opening;

the step of releasing the second medication comprises releasing the second medication from one of the hands.

5. The method of claim 3 wherein the step of reading the first machine readable identifier occurs while holding with a robotic arm the first medication in the space above the access opening;

the step of releasing the first medication comprises releasing the first medication from the robotic arm;

the step of reading the second machine readable identifier occurs while holding with the robotic arm the second medication in the space above the access opening;

the step of releasing the second medication comprises releasing the second medication from the robotic arm.

6. The method of claim 1 wherein the first machine readable identifier is connected to a package containing a number of unit doses of the first medication, wherein the number represents a plurality of the unit doses;

after determining that the first medication is a correct medication, making an entry of the number of unit doses with a computer input mechanism so that the entry of the number is recognized by a computer program to indicate that the number of unit doses is associated with the package; and wherein the step of dropping the first medication comprises dropping the package containing the number of unit doses through the opened access opening into the container by releasing the package while the package is above the opened access opening.

7. The method of claim 1 wherein the second machine readable identifier is connected to a package containing a number of unit doses of the second medication, wherein the number represents a plurality of the unit doses;

after determining that the second medication is a correct medication, making an entry of the number of unit doses with a computer input mechanism so that the entry of the number is recognized by a computer program to indicate that the number of unit doses is associated with the package; and wherein the step of dropping the second medication comprises dropping the package containing the number of unit doses through the reopened access opening into the container by releasing the package while the package is above the reopened access opening.

8. The method of claim 1 further comprising:

providing a plurality of storage bins each containing a plurality of medications;

picking with a robotic arm or one of a person's hands the first medication from one of the storage bins;

while holding the picked first medication with the robotic arm or one of the hands, moving the robotic arm or one of the hands away from the one of the storage bins from which the first medication was picked to adjacent the access opening;

wherein the step of reading the first machine readable identifier comprises reading the first machine readable identifier while holding with the robotic arm or one of the hands the picked first medication adjacent the access opening;

after the step of reading the first machine readable identifier, dropping the first medication from the robotic arm or one of the hands while the robotic arm or one of the hands is above the access opening to effect the step of dropping the first medication through the opened access opening into the container;

after the step of dropping the first medication, moving the robotic arm or one of the hands away from the access opening to adjacent one of the storage bins in which the second medication is stored;

picking with the robotic arm or one of the hands the second medication from the one of the storage bins in which the second medication is stored;

while holding the picked second medication with the robotic arm or one of the hands, moving the robotic arm or one of the hands away from the one of the storage bins from which the second medication was picked to adjacent the access opening;

wherein the step of reading the second machine readable identifier comprises reading the second machine readable identifier while holding with the robotic arm or one of the hands the picked second medication adjacent the access opening;

after the step of reading the second machine readable identifier, dropping the second medication from the robotic arm or one of the hands while the robotic arm or one of the hands is above the access opening to effect the step of dropping the second medication through the reopened access opening into the container.

9. The method of claim 8 wherein the one of the storage bins from which the first medication was picked is different from the one of the storage bins from which the second medication was picked.

10. The method of claim 1 further comprising:

providing a box defining an interior chamber which extends over the wall;

picking the first medication with a robotic arm or one of a person's hands from a location outside the box;

while holding the first medication with the robotic arm or one of the hands, inserting the robotic arm or one of the hands into the box;

dropping the first medication from the inserted robotic arm or one of the hands to effect the step of dropping the first medication through the opened access opening into the container;

after dropping the first medication, withdrawing the robotic arm or one of the hands from the box;

picking the second medication with the withdrawn robotic arm or one of the hands from a location outside the box;

while holding the picked second medication in the robotic arm or one of the hands, reinserting the robotic arm or one of the hands into the box;

dropping the second medication from the reinserted robotic arm or one of the hands to effect the step of dropping the second medication through the reopened access opening into the container; and after dropping the second medication, withdrawing the robotic arm or one of the hands from the box.

11. The method of claim 10 wherein the location from which the first medication was picked is a first storage bin outside the box; and the location from which the second medication was picked is a second different storage bin outside the box.

12. A method comprising the steps of:
determining with a medication identification sensor whether a first medication is a correct or incorrect medication;
producing a correct or incorrect medication indicator respectively depending on whether the first medication is the correct or incorrect medication in accordance with the step of determining;
causing entry of the first medication into a medication container after the step of producing;
sensing the entry with an entry sensor to verify that the first medication has entered the container;
further comprising, after the steps of determining, producing, causing and sensing, the steps of
determining with a medication identification sensor whether a second medication is a correct or incorrect medication;
producing a correct or incorrect medication indicator related to the second medication respectively depending on whether the second medication is the correct or incorrect medication in accordance with the step of determining whether the second medication is a correct or incorrect medication;
causing entry of the second medication into the container after the step of producing the indicator related to the second medication; and
sensing the entry of the second medication with an entry sensor to verify that the second medication has entered the container; and further comprising the steps of
providing a containment device which defines a filling position, wherein the containment device includes a wall which has inner and outer surfaces and defines an access opening extending from the inner surface to the outer surface above the filling position, wherein the wall carries a cover which is movable relative to the wall between an open position in which medications may pass through the access opening into the container and a closed position in which medications may not pass through the access opening into the container;
positioning the container at the filling position under the wall and access opening by moving the medication container relative to the wall to insert the medication container into the filling position so that the access opening is above the medication container in the filling position;
opening the access opening by moving the cover from the closed position to the open position while the container remains at the filling position;
dropping the first medication through the opened access opening into the container to effect the step of causing entry of the first medication;
closing the access opening, after the step of dropping and before the step of determining whether the second medication is a correct or incorrect medication, by moving the cover from the open position to the closed position;
reopening the closed access opening after the step of producing the indicator related to the second medication by moving the cover from the closed position to the open position while the container remains at the filling position;
dropping the second medication through the reopened access opening into the container while the container remains at the filling position to effect the step of causing entry of the second medication into the container;
removing the container with the first and second medications therein from the filling position by moving the container relative to the wall;
providing a plurality of storage bins each containing a plurality of medications;
picking with a robotic arm or one of a person's hands the first medication from one of the storage bins;
before the step of dropping the first medication, moving the picked first medication with the robotic arm or one of the hands away from the one of the storage bins from which the first medication was picked to adjacent the access opening;
after the step of dropping the first medication, moving the robotic arm or one of the hands away from the access opening to adjacent one of the storage bins in which the second medication is stored;
picking with the robotic arm or one of the hands the second medication from the one of the storage bins in which the second medication is stored;
before the step of dropping the second medication, moving the picked second medication with the robotic arm or one of the hands away from the one of the storage bins from which the second medication was picked to adjacent the access opening;
after the step of dropping the second medication, moving the robotic arm or one of the hands away from the access opening;
providing a box defining an interior chamber which extends over the wall;
wherein the storage bin from which the first medication was picked is outside the box;
wherein the storage bin from which the second medication was picked is outside the box;
wherein the step of moving the picked first medication away from the one of the storage bins from which the first medication was picked to adjacent the access opening comprises inserting the robotic arm or one of the hands into the box through an opening formed in a wall of the box;
dropping the first medication from the inserted robotic arm or one of the hands to effect the step of dropping the first medication through the opened access opening into the container;
wherein the step of moving the robotic arm or one of the hands away from the access opening to adjacent the one of the storage bins in which the second medication is stored comprises withdrawing the inserted robotic arm or one of the hands from the box through the opening formed in the wall of the box;
wherein the step of moving the picked second medication away from the one of the storage bins from which the second medication was picked to adjacent the access opening comprises reinserting the robotic arm or one of the hands into the box through the opening formed in the wall of the box;
dropping the second medication from the reinserted robotic arm or one of the hands to effect the step of dropping the second medication through the reopened access opening into the container; and wherein the step of moving the robotic arm or one of the hands away from the access opening after the step of dropping the second medication comprises withdrawing the robotic arm or one of the hands from the box through the opening formed in the wall of the box.

13. The method of claim 12 wherein the step of dropping the first medication comprises releasing the first medication from one of the hands while the first medication is above the opened access opening; and the step of dropping the second medication comprises releasing the second medication from one of the hands while the second medication is above the reopened access opening.

14. The method of claim 12 wherein the step of moving the robotic arm or one of the hands while holding the picked first medication with the robotic arm or one of the hands comprises moving the robotic arm or one of the hands away from the one of the storage bins from which the first medication was picked to a space above the access opening;

the step of reading the first machine readable identifier comprises reading the first machine readable identifier while holding with the robotic arm or one of the hands the picked first medication in the space above the access opening;

the step of dropping the first medication comprises dropping the first medication from the robotic arm or one of the hands while the robotic arm or one of the hands is in the space above the access opening;

the step of moving the robotic arm or one of the hands after the step of dropping the first medication comprises moving the robotic arm or one of the hands away from the space above the access opening to adjacent the one of the storage bins in which the second medication is stored;

the step of moving the robotic arm or one of the hands while holding the picked second medication with the robotic arm or one of the hands comprises moving the robotic arm or one of the hands away from the one of the storage bins from which the second medication was picked to the space above the access opening;

the step of reading the second machine readable identifier comprises reading the second machine readable identifier while holding with the robotic arm or one of the hands the picked second medication in the space above the access opening;

the step of dropping the second medication comprises dropping the second medication from the robotic arm or one of the hands while the robotic arm or one of the hands is in the space above the access opening.

15. A method comprising the steps of:
determining with a medication identification sensor whether a first medication is a correct or incorrect medication;
producing a correct or incorrect medication indicator respectively depending on whether the first medication is the correct or incorrect medication in accordance with the step of determining;
causing entry of the first medication into a medication container after the step of producing;
sensing the entry with an entry sensor to verify that the first medication has entered the container;
further comprising, after the steps of determining, producing, causing and sensing, the steps of
determining with a medication identification sensor whether a second medication is a correct or incorrect medication;
producing a correct or incorrect medication indicator related to the second medication respectively depending on whether the second medication is the correct or incorrect medication in accordance with the step of determining whether the second medication is a correct or incorrect medication;
causing entry of the second medication into the container after the step of producing the indicator related to the second medication; and
sensing the entry of the second medication with an entry sensor to verify that the second medication has entered the container; and further comprising the steps of
providing a containment device which defines a filling position, wherein the containment device includes a wall which has inner and outer surfaces and defines an access opening extending from the inner surface to the outer surface above the filling position, wherein the wall carries a cover which is movable relative to the wall between an open position in which medications may pass through the access opening into the container and a closed position in which medications may not pass through the access opening into the container;
positioning the container at the filling position under the wall and access opening by moving the medication container relative to the wall to insert the medication container into the filling position so that the access opening is above the medication container in the filling position;
opening the access opening by moving the cover from the closed position to the open position while the container remains at the filling position;
dropping the first medication from one of a person's hands through the opened access opening into the container to effect the step of causing entry of the first medication;
closing the access opening, after the step of dropping and before the step of determining whether the second medication is a correct or incorrect medication, by moving the cover from the open position to the closed position;
reopening the closed access opening after the step of producing the indicator related to the second medication by moving the cover from the closed position to the open position while the container remains at the filling position;
dropping the second medication from one of the hands through the reopened access opening into the container while the container remains at the filling position to effect the step of causing entry of the second medication into the container;
removing the container with the first and second medications therein from the filling position by moving the container relative to the wall;
providing a box defining an interior chamber which extends over the wall;
picking the first medication with one of the hands from a location outside the box;
while holding the picked first medication in one of the hands, inserting the one of the hands holding the picked first medication into the box through an opening formed in a wall of the box;
dropping the first medication from the inserted one of the hands to effect the step of dropping the first medication through the opened access opening into the container;
after dropping the first medication, withdrawing the inserted one of the hands from the box through the opening formed in the wall of the box;

picking the second medication with one of the hands from a location outside the box;

while holding the picked second medication in one of the hands, inserting the one of the hands holding the picked second medication into the box through the opening formed in the wall of the box;

dropping the second medication from the inserted one of the hands holding the picked second medication to effect the step of dropping the second medication through the reopened access opening into the container; and after dropping the second medication, withdrawing from the box the one of the hands which dropped the second medication through the opening formed in the wall of the box.

16. The method of claim 15 further comprising:

providing a plurality of storage bins each containing a plurality of medications;

picking with one of the hands the first medication from one of the storage bins;

moving the picked first medication away from the one of the storage bins from which the first medication was picked to adjacent the access opening;

after the step of dropping the first medication, moving the one of the hands which dropped the first medication away from the access opening.

17. The method of claim 16 further comprising:

picking with one of the hands the second medication from one of the storage bins;

moving the picked second medication away from the one of the storage bins from which the second medication was picked to adjacent the access opening;

after the step of dropping the second medication, moving the one of the hands which dropped the second medication away from the access opening.

18. The method of claim 17 wherein the one of the storage bins from which the first medication was picked is different from the one of the storage bins from which the second medication was picked.

* * * * *